US009925299B2

(12) United States Patent
Kaplan et al.

(10) Patent No.: US 9,925,299 B2
(45) Date of Patent: Mar. 27, 2018

(54) SILK-BASED FABRICATION TECHNIQUES TO PREPARE HIGH STRENGTH CALCIUM PHOSPHATE CERAMIC SCAFFOLDS

(71) Applicant: TUFTS UNIVERSITY, Medford, MA (US)

(72) Inventors: David L. Kaplan, Concord, MA (US); Tim Jia-Ching Lo, Taoyuan (TW); Stephanie McNamara, North Attleboro, MA (US)

(73) Assignee: Tufts University, Medord, MA (US)

( * ) Notice: Subject to any disclaimer, the term of this patent is extended or adjusted under 35 U.S.C. 154(b) by 64 days.

(21) Appl. No.: 14/437,881

(22) PCT Filed: Oct. 28, 2013

(86) PCT No.: PCT/US2013/067047
§ 371 (c)(1),
(2) Date: Apr. 23, 2015

(87) PCT Pub. No.: WO2014/066884
PCT Pub. Date: May 1, 2014

(65) Prior Publication Data
US 2015/0283298 A1 Oct. 8, 2015

Related U.S. Application Data

(60) Provisional application No. 61/719,146, filed on Oct. 26, 2012, provisional application No. 61/809,535, filed on Apr. 8, 2013, provisional application No. 61/881,653, filed on Sep. 24, 2013.

(51) Int. Cl.
| | |
|---|---|
| *A61K 35/64* | (2015.01) |
| *A61L 27/54* | (2006.01) |
| *A61L 27/10* | (2006.01) |
| *A61L 27/12* | (2006.01) |
| *A61L 27/22* | (2006.01) |
| *A61L 27/46* | (2006.01) |
| *A61L 27/56* | (2006.01) |
| *A61L 27/38* | (2006.01) |

(52) U.S. Cl.
CPC ............ *A61L 27/227* (2013.01); *A61L 27/12* (2013.01); *A61L 27/3821* (2013.01); *A61L 27/46* (2013.01); *A61L 27/54* (2013.01); *A61L 27/56* (2013.01); *A61L 2300/412* (2013.01); *A61L 2430/02* (2013.01)

(58) Field of Classification Search
CPC .... A61L 27/46; A61L 27/12; A61L 2300/412; A61L 2430/02; A61L 27/227; A61L 27/3821; A61L 27/54; A61L 27/56; C08L 89/00
See application file for complete search history.

(56) References Cited

U.S. PATENT DOCUMENTS

| | | |
|---|---|---|
| 6,387,413 B1 | 5/2002 | Miyata et al. |
| 8,354,501 B2 | 1/2013 | Kaplan et al. |
| 2011/0172394 A1* | 7/2011 | Knight ............... A61L 27/3604 530/353 |
| 2015/0165092 A1* | 6/2015 | Kaplan ................ A61L 27/56 424/130.1 |
| 2015/0183841 A1* | 7/2015 | Lo ...................... A61L 27/56 424/402 |

OTHER PUBLICATIONS

U.S. Appl. No. 61/621,209, filed Apr. 6, 2012, Kaplan et al.
U.S. Appl. No. 61/883,732, filed Sep. 27, 2013, Kluge et al.
U.S. Appl. No. 61/883,933, filed Sep. 27, 2013, Omenetto et al.
Acharya, C. et al., Performance evaluation of a silk protein-based matrix for the enzymatic conversion of tyrosine to $_L$-DOPA, Biotechnol. J., 3:226-233 (2008).
Author Not Known, Coulson and Richardson's Chemical Engineering, Particle Technology and Separation Processes, vol. 2, 5th Edition, ed. Richardson, J.F. et al., Pergamon Press, p. 126 (1978).
Bayraktar, O. et al., Silk fibroin as a novel coating material for controlled release of theophylline, European Journal of Pharmaceutics and Biopharmaceutics, 60:373-381 (2005).
Demura, M. and Asakura, T., Immobilization of glucose oxidase with Bombyx mori silk fibroin by only stretching treatment and its application to glucose sensor, Biotechnol. Bioeng., 33(5):598-603 (1989).
Deville, S. et al., Freeze casting of hydroxyapatite scaffolds for bone tissue engineering, Biomaterials, 27(32):5480-9 (2006).
Fukui, A. et al., Isolation and Characterization of *Xenopus* Follistatin and Activins, Devel. Biol., 159:131-139 (1993).
Hofmann, S. et al., Silk fibroin as an organic polymer for controlled drug delivery, Journal of Controlled Release, 111:219-227 (2006).
Hu, X. et al., Regulation of Silk Material Structure by Temperature-Controlled Water Vapor Annealing, Biomacromolecules, 12:1686-1696 (2011).
Jin, I.J. et al., Water-Stable Silk Films with Reduced Beta-Sheet Content, Adv. Funct. Mater., 15:1241-1247 (2005).
Jones et al., Isolation of VGR-2, a Novel Member of the Transforming Growth Factor-beta-Related Gene Family, Mol. Endocrinol., 611961 (1992).
Li, M. et al., Study on Porous Silk Fibroin Materials. II. Preparation and Characteristics of Spongy Porous Silk Fibroin Materials, Journal of Applied Polymer Science, 79:2192-2199 (2001).
Lucas, F. et al., The silk fibroins, Advances in Protein Chemistry, 13:107-242 (1958).
Macchetta, A. et al., Fabrication of HA/TCP scaffolds with a graded and porous structure using a camphene-based freeze-casting method, Acta Biomater., 5(4):1319-27 (2009).
Mandal, B. et al., High-strength silk protein scaffolds for bone repair, Proceedings of the National Academy of Sciences USA, 109(20):7699-7704 (2012).

(Continued)

*Primary Examiner* — Chris R Tate
*Assistant Examiner* — Aaron J Kosar
(74) *Attorney, Agent, or Firm* — Choate, Hall & Stewart LLP

(57) ABSTRACT

The disclosure provides ceramic materials comprising calcium phosphate material and silk and processes and methods for preparing and uses thereof.

27 Claims, 26 Drawing Sheets

(56) References Cited

OTHER PUBLICATIONS

Min, S. et al., Preparation and Characterization of Crosslinked Porous Silk Fibroin Gel, Sen'l Gakkaishi, 54(2):85-92 (1997).

Miyairi, S. and Sugiura, M., Properties of β-Glucosidase Immobilized in Sericin Membrane, Journal of Fermentation Technology, 56(4):303-308 (1978).

Nazarov, R. et al., Porous 3-D scaffolds from regenerated silk fibroin, Biomacromolecules, 5(3):718-26 (2004).

Potoczek, M. et al., Manufacturing of highly porous calcium phosphate bioceramics via gel-casting using agarose, Ceramics International, 35(6):2249-54 (2009).

Soon, Y. et al., Compressive strength and processing of camphene-based freeze cast calcium phosphate scaffolds with aligned pores, Materials Letters, 63(17):1548-50 (2009).

Varma, H.K. et al., Polymeric precursor route for the preparation of calcium phosphate compounds, Ceramics International, 24(6):467-470 (1998).

Wang, Y. et al., A Large Family of Putative Transmembrane Receptors Homologous to the Product of the *Drosophila* Tissue Polarity Gene frizzled, The Journal of Biological Chemistry, 271(8):4468-76 (1996).

Wenk, et al., Silk Fibroin Spheres as a Platform for Controlled Drug Delivery, Journal of Controlled Release, 132(1):26-34 (2008).

Yang, T.Y. et al., Hydroxyapatite scaffolds processed using a TBA-based freeze-gel casting/polymer sponge technique, J. Mater. Sci. Mater. Med., 21(5):1495-502 (2010).

Zhang, Y. and Zhang M., Three-dimensional macroporous calcium phosphate bioceramics with nested chitosan sponges for load-bearing bone implants, J. Biomed. Mater. Res., 61(1):1-8 (2002).

Zhang, Y. and Zhang, M., Synthesis and characterization of macroporous chitosan/calcium phosphate composite scaffolds for tissue engineering, J. Biomed. Mater. Res., 55(3):304-12 (2001).

\* cited by examiner

SILK-BASED FABRICATION TECHNIQUES TO PREPARE HIGH STRENGTH CALCIUM PHOSPHATE CERAMIC SCAFFOLDS

CROSS-REFERENCE TO RELATED APPLICATIONS

This application claims benefit under 35 U.S.C. § 119(e) of the U.S. Provisional Application No. 61/719,146, filed Oct. 26, 2012; No. 61/809,535, filed Apr. 8, 2013; and No. 61/881,653, filed Sep. 24, 2013 the contents of all which are incorporated herein by reference in their entireties.

GOVERNMENT SUPPORT

This invention was made with government support under grant no. P41 EB002520 awarded by the National Institutes of Health. The government has certain rights in the invention.

TECHNICAL FIELD

The present disclosure relates generally to calcium phosphate materials, processes and methods for preparing and uses thereof.

BACKGROUND

Bone is a complex, hierarchical composite consisting of both inorganic and organic components. This includes about 40-50% calcium deficient ion-substituted hydroxyapatite in the form of elongated crystals, about 30-40% type I collagen fibers, and the remaining 10% of water and cellular components. Osseous tissue is highly vascularized, dynamic, and adapts to changes in mechanical loading. Bone exhibits anisotropic behavior in that its mechanical properties are directionally dependent, and it resists loading best in the axial direction. Human compact bone has a compressive strength of about 170-200 MPa, a tensile strength of about 100-120 MPa, and a shear strength of about 60-80 MPa. Although bone is rather brittle, it does exhibit a certain degree of elasticity conferred by the type I collagen fiber reinforcement.

Calcium phosphate (CaP) bioceramics have been used for bone tissue engineering for decades. Calcium phosphates consist of three major elements: calcium, phosphorus, and oxygen, all of which are highly abundant on earth. Many calcium phosphates also include hydrogen as an acidic orthophosphate (i.e. $H_2PO_4^-$) or as incorporated water (i.e. $CaHPO_4.H_2O$). Calcium phosphates are distinguished from each other by the type of phosphate anion in the complex and the oxidation state of the phosphorous. Calcium phosphates in particular contain the orthophosphate anion ($PO_4^{3-}$) and include HA (hydroxyapatite) ($Ca_{10}(PO_4)_6(OH)_2$), alpha and beta TCP (tri-calcium phosphate) ($Ca_3(PO_4)_2$), CDHA (calcium-deficient hydroxyapatite), MCPA (monocalcium phosphate anhydrous), MCPD (monocalcium phosphate dehydrate), DCPA (dicalcium phosphate anhydrous), DCPD (dicalcium phosphate dihydrate), TTCP (tetracalcium phosphate), and FA (fluoroapatite). Other materials that have been explored for their potential use as biomaterials for bone tissue engineering include bioglass and calcium silicate.

Although calcium phosphate ceramics are bioactive and biocompatible making them suitable for tissue engineering, there are several disadvantages of this material that prevent it from being used as an effective repair material for load-bearing bone defects. Specifically, while calcium phosphate ceramics exhibit high compressive strengths and can withstand large loading forces before fracture, they are extremely brittle. Brittle materials exhibit very low fracture toughness under loading, and have little to no impact resistance. Even though calcium phosphates, such as hydroxyapatite, closely mimic the chemical composition of the calcium phosphate material found in bone, CaP ceramics cannot match the fracture toughness of human bone (1.3 $kJm^{-3}$) due to the lack of a tough, ductile component like collagen. Therefore, most research on calcium phosphate scaffolds for bone tissue engineering has focused on the use of these ceramics for non-load-bearing bone repair. Furthermore, the design of CaP bioceramic scaffolds generally requires a balance between porosity and mechanical strength. In order to encourage native bone ingrowth and osteogenesis within these ceramics, the scaffolds must exhibit a minimum degree of porosity (about 60-70% total pore volume) with pore sizes in the range of 50 to 100 microns. However, increasing the scaffold porosity of calcium phosphate ceramics significantly decreases the mechanical strength of the overall structure. Moreover, CaP ceramics degrade very slowly by a process of ion dissolution mediated by acidic environments. Thus, difficulties often arise in matching resorption rate with the rate of bone ingrowth within these materials.

A number of methods are known in the art for preparing calcium phosphate ceramic scaffolds and are described, for example, in Sylvain D., E. Saiz, A. Tomsia. Freeze casting of hydroxyapatite scaffolds for bone tissue engineering. *Biomaterials*. 2006. 27:32. 5480-89; Zang, Y., M. Zang. Synthesis and characterization of macroporous chitosan/calcium phosphate scaffolds for tissue engineering. *Journal of Biomedical Research Materials*. 2001. 55:3. 304-312; Zang, Y., M. Zang. Three-dimensional macroporous calcium phosphate bioceramics with nested chitosan sponges for load-bearing bone implants. *Journal of Biomedical Research Materials*. 2002. 61:1. 1-8; Varma, H. K., S. N. Kalkura, R. Sivakumar. Polymeric precursor route for the preparation of calcium phosphate compounds. *Ceramics International*. 1998. 24:6. 467-470; Soon, Y., K. Shin, Y. Koh, J. Lee, H. Kim. Compressive strength and processing of camphene-based freeze cast calcium phosphate scaffolds with aligned pores. *Materials Letters*. 2009. 63:17. 1548-50; Maccetta, A., I. G. Turner, C. R. Bowen. Fabrication of HA/TCP scaffolds with a graded and porous structure using a camphene-based freeze casting method. *Acta Biomaterialia*. 2009. 5:4. 1319-27; Potoczek, M., A. Zima, Z. Paszkiewicz, A. Slosarczyk. Manufacturing of highly porous calcium phosphate bioceramics via gel-casting using agarose. *Ceramics International*. 2009. 35:6. 2249-54; and Yang, T. Y., J. M. Lee, S. Y. Yoon, H. C. Park. Hydroxyapatite scaffolds processed using a TBA-based freeze-gel casting/polymer sponge technique. *Journal of Materials Science: Materials in Medicine*. 2010. 21:5. 1495-1502. Exemplary methods from the art include, but are not limited to:

Freeze-Drying: Calcium phosphate powders are mixed with water to create a ceramic slurry that is frozen and subsequently lyophilized to generate a freeze-dried ceramic green body with varying degrees of porosity depending on the ratio of ceramic powder to water. The resultant green body is then sintered.

Gel Casting: In situ polymerization of organic monomers in a ceramic slurry leads to rapid solidification and formation of ceramic green bodies. The organic gelling agents in the green bodies later act as sacrificial polymers during the sintering process to create voids in the final scaffold, imparting porosity in the finished product.

Dry Pressing: Dry calcium phosphate powder is packed and pressed into a mold to create a structurally stable blank and sintered to create the finished ceramic.

Sacrificial Porogens: Various synthetic polymer powders and inorganic porogens (i.e. naphthalene particles, PVC/PS/PEG/PMMA beads, cellulose acetate, resins, $SiO_2$ particles, etc.) have been mixed with calcium phosphate ceramic paste to form green bodies. These porogens later act as sacrificial polymers by burning off during the sintering process thereby creating porosity in the finished scaffold. Other materials such as salts (NaCl, $BaSO_4$, $SrSO_4$) and liquids (camphene, oils) have also been used as porogens and binding agents for fabricating these calcium phosphate scaffolds.

Polyurethane Sponge Method: Porous polyurethane sponge is dipped into a calcium phosphate ceramic slurry and then sintered. The polyurethane sponge acts as a sacrificial polymer during the sintering process to create porosity in the finished ceramic scaffold.

Direct Foaming: Porous calcium phosphate ceramic materials are produced by introducing air bubbles into the CaP ceramic suspension. The resulting green state foams are subsequently sintered at high temperatures to obtain highly porous CaP ceramics.

However, the methods described above have several disadvantages that prevent them from generating CaP ceramics scaffolds that are sufficient for load-bearing orthopedic applications. First, these methods do not allow for the fabrication of highly stable calcium phosphate ceramic "green bodies", defined as ceramic bodies that have not yet been sintered or fired. This prevents the fabrication of complex geometric shapes, and limits scaffolding to simple geometries (cylinders, rectangles, etc.). The ability to generate CaP ceramic scaffolds of complex geometry would allow for patient-specific design of ceramic bone grafts to fit the particular defect geometry. In addition, the methods of CaP scaffold fabrication mentioned above do not allow for the creation of high strength CaP scaffolds that can match the mechanical properties of human cortical bone. This is mainly due a lack of control over the total porosity and pore size in the finished scaffold.

Thus, there is a need in the art for methods of fabrication of high strength, complex geometry calcium phosphate ceramic scaffolds formed from highly stable calcium phosphate ceramic green bodies. Additionally, there is a need in the art for methods of fabrication of high strength calcium phosphate ceramic scaffolds matching that of human cortical bone.

SUMMARY

Aspects of the invention disclosed herein are based on inventors' discovery that natural polymers such as silk fibroin can be used to create green body ceramics with mechanical properties ideal for orthopedic applications. This includes the use of silk fibroin as a sacrificial porogen, as a consolidation reagent to condense ceramic grains. To the inventors' knowledge, this is the first use of silk as a porogen. In one aspect, the present disclosure provides a method of preparing a calcium phosphate ceramic material. Generally, the method comprises preparing a composition comprising silk (e.g., silk fibroin) and calcium phosphate (CaP); forming a green body from the composition; and sintering the green body to form the porous ceramic material. The composition can be in the form of a solution, paste, slurry, suspension, colloid, mixture, dispersion, and the like. Generally, the silk fibroin and the calcium phosphate material are homogenously dispersed in the composition.

After sintering, the ceramic material can be processed into a desired shape. In some embodiments, the green body can be processed into a desired shape before sintering. It is noted that the sintering step can be omitted. For example, when a self-setting calcium phosphate material is used, the sintering step can be optional.

In some embodiments, the green body can be in the form of a ceramic blank. The ceramic blank can be sintered and modified by one or more post-processing methods to create the finished ceramic material of the desired ceramic shape. In some embodiments, the green body can be of a pre-defined shape, e.g., the desired ceramic shape, which can be sintered to provide the finished ceramic material of the desired ceramic shape.

In some embodiments, the green body can be stabilized before sintering. For example, the green body can be stabilized by subjecting the silk/CaP mixture to an elevated temperature. Alternatively, the green body can be stabilized by freeze-drying the silk/CaP mixture via freeze-drying, e.g., lyophilization. In some embodiments, the green body can be stabilized by applying pressure to the composition.

In another aspect, the disclosure provides a calcium phosphate ceramic material. The ceramic material can be prepared according to the method disclosed herein.

In another aspect, the disclosure provides an implant for the repair, augmentation, or replacement of substantially all or part of one or more bones, or as a substitute for bone grafts in orthopedic applications, the implant comprising a ceramic material as described herein. The implant can further comprise a bone anchor, screw, pin, rod, plate, or other support structure made from the ceramic material using the methods described herein for repair or stabilization of the damaged bone region (fracture, augmentation region, defect, etc.). The bone anchor, screw, or plate can comprise a plurality of threads or filaments of any material (Note: you can include silk fibers or particles in the finish ceramic IF the calcium phosphate does not need to be sintered e.g. reactive CaPs that can set on their own) embedded in the material. The implantable material as described herein can be used for the repair, augmentation, or replacement of substantially all or part of one or more bones, or as a substitute for bone grafts, or as a securing device in orthopedic applications. The implantable material can be resorable or non-resorable.

DETAILED DESCRIPTION

Figure 1:
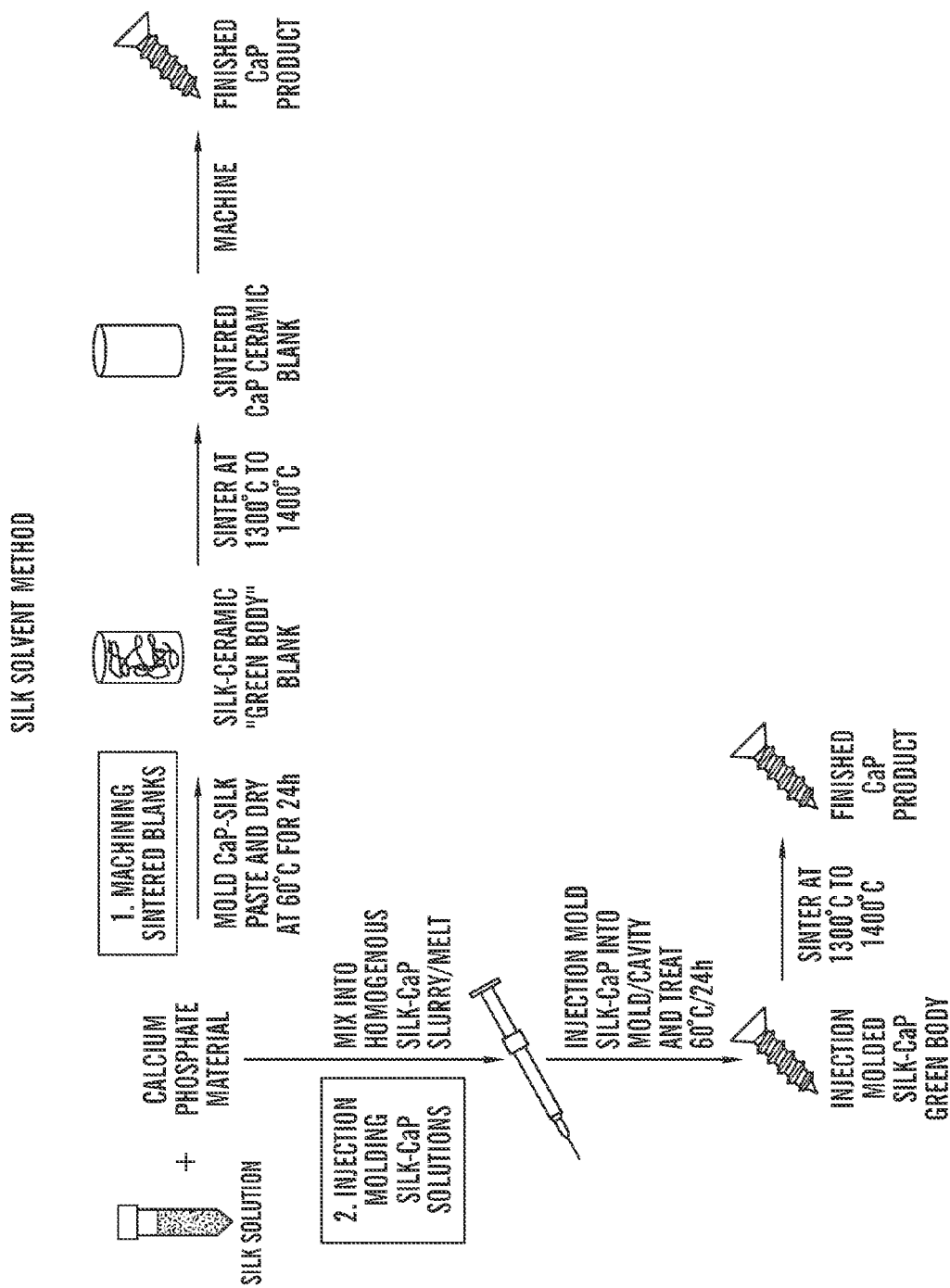
FIG. 1 is a schematic representation of the Silk Solvent Method (SSM), which is an exemplary embodiment of a method for preparing CaP ceramic scaffolds using silk via either machining of pre-formed sintered blanks, or injection molding of silk/CaP composites.

The invention is based in part upon the inventors' discovery that natural polymers such as silk can be used as a binding agent in the production of highly stable calcium phosphate ceramic green bodies, and later, as a sacrificial polymer during high temperature sintering for the preparation of porous, sintered calcium phosphate ceramics. It is believed that the use of silk as the sacrificial polymer during sintering of the green bodies is beneficial since silk fibroin protein is a biocompatible polymer. Thus, using a natural polymer, like silk, as a sacrificial porogen avoids inflammatory complications that could potentially arise after scaffold implantation due to the toxic residue left over by synthetic polymeric porogens after sintering. Further, the methods described herein simplify the process of creating calcium phosphate ceramic bone grafts because silk is easily obtainable, calcium phosphate powders dissolve easily into silk solution, silk can stabilize the ceramic green state prior to sintering by beta sheet formation, which can be induced via curing with mild heating conditions or by lyophilization into a sponge-like silk structure that encapsulates the ceramic particles. The methods described herein solve the problem of creating stable CaP ceramic green bodies of complex geometric shape by providing simple, reproducible methods for the fabrication of said complex, stable CaP ceramic green bodies. These green bodies can be formed by injection molding prior to sintering, or by machining ceramic blanks that have already been sintered into the desired shape. Further, the methods described herein can also solve the problem of generating a minimum degree of porosity in the finished sintered CaP scaffold by using silk in the green body as a sacrificial polymer/porogen during sintering.

Accordingly, in one aspect provided herein is a method for preparing ceramic material. The method generally comprising providing a green body prepared from a composition comprising silk fibroin and a calcium phosphate material and sintering the green body to form the calcium phosphate (CaP) ceramic material. Without limitations, the composition can be in the form of a solution, paste, slurry, suspension, colloid, mixture, dispersion, or any combinations thereof. In some embodiments, the composition for forming the green body can be substantially free of solvents, i.e., a dry mixture of silk fibroin and the calcium phosphate material.

It is to be noted that, while the methods and compositions disclosed herein are described with silk, other natural polymers can replace or supplement silk. Exemplary polymers that can replace or supplement silk in the aspects of the invention include, but are not limited to, collagen, alginate, cellulose, chitosan, agarose, elastin, fibrin, fibrinogen, hyaluronic acid, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), poly(phosphoesters), poly (L-lactide) (PLLA), poly(D,L-lactide) (PDLLA), polyglycolide (PGA), poly(lactide-co-glycolide) (PLGA), poly(L-lactide-co-D, L-lactide), poly(D,L-lactide-co-trimethylene carbonate), polyhydroxybutyrate (PHB), poly($\epsilon$-caprolactone), poly($\delta$-valerolactone), poly($\gamma$-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly (ethylene terephthalate)polyamide, and copolymers thereof. Preferred cohesiveness agents also include alginic acid, arabic gum, guar gum, xantham gum, gelatin, chitin, chitosan, chitosan acetate, chitosan lactate, chondroitin sulfate, N,O-carboxymethyl chitosan, a dextran (e.g., $\alpha$-cyclodextrin, $\beta$-cyclodextrin, $\gamma$-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and mixtures thereof. Without wishing to be bound by a theory, polymers can be used to replace or supplement silk in the methods and compositions disclosed herein since natural polymers will burn off during the sintering step. In some embodiments, the natural polymer excludes starch.

As used herein, the terms "green body" and "green structure" mean an unsintered three-dimensional body or structure comprising a plurality of discrete particles held together by one or more of inter-particle forces and a binder material. For ceramics, a "conventional binder material" is generally defined as a substance added to the ceramic material prior to sintering that acts as a medium to hold ceramic particles or grains together. These conventional binders are generally removed completely during sintering (sacrificial). Sometimes "pre-ceramic binders" can be used. A "pre-ceramic binder" is generally defined as a substance added to the ceramic material prior to sintering that, when sintered, converts into a fully-sintered phase of the finished ceramic itself. These pre-ceramic binders are therefore not removed from the ceramic during sintering. As used herein, binder material encompasses both the conventional binders and the pre-ceramic binders.

Without wishing to be bound by a theory, it is believed that the calcium phosphate material in the ceramic provides low porosity and high mechanical strength, and exhibits a slow degradation profile. In addition, the silk in the ceramic is biocompatible.

Generally, the silk/CaP material composition or the porous material prepared therefrom can comprise any ratio of silk/CaP. For example, the ratio of silk to calcium phosphate material in the composition or the porous material prepared therefrom can range from about 1000:1 to about 1:1000. The ratio can be based on weight or moles. In some embodiments, the ratio of silk to calcium phosphate material in the composition or the porous material prepared therefrom can range from about 500:1 to about 1:500 (w/w), from about 250:1 to about 1:250 (w/w), from about 50:1 to about 1:200 (w/w), from about 10:1 to about 1:150 (w/w) or from about 5:1 to about 1:100 (w/w). In some embodiments, ratio of silk to calcium phosphate material in the composition or the porous material prepared therefrom can be about 1:99 (w/w), about 1:4 (w/w), about 2:3 (w/w), about 1:1 (w/w) or about 4:1 (w/w). In some embodiments, the porous material comprises very little or essentially no silk. In some embodiments, the ratio of CaP to silk in the composition or the porous material prepared therefrom can be about 100/0 (i.e. no silk), 99/1, 90/10, 80/20, 70/30, 60/40, 50/50, 40/60, 30/70, 20/80, 10/90, 1/99, 0/100 (w/w) (i.e., no CaP). Without wishing to be bound by a theory, higher ratio of CaP to silk provides ceramic materials of higher strength but lower porosity. Thus, the ratio of CaP to silk can be optimized to provide ceramic materials of desired strength and/or porosity.

The disclosure also provides a composition comprising silk and a calcium phosphate material. In some embodiments, the composition comprises silk and a reactive calcium phosphate material. In some embodiments, the silk can be in the form of silk fibers, silk particles, silk gels and the like.

Generally the method comprises: (i) providing a composition comprising silk fibroin and a calcium phosphate material; (ii) forming a green body from said composition; and (iii) sintering the green body to form the porous CaP ceramic material.

In some embodiments, the method comprises: (i) preparing a solution comprising silk fibroin and a calcium phosphate material; (ii) forming a green body from said composition; and (iii) sintering the green body to form the porous CaP ceramic material.

When the composition comprising the silk and the calcium phosphate material is in the form of a solution, the solution can be prepared by any method available to one of skill in the art. For example, a silk fibroin solution can be prepared first using methods well known in the art, and the calcium phosphate material (either in dry form or in a solution) can be added to the silk solution. Alternatively, a solution comprising the calcium phosphate solution can be prepared and silk (either in dry form or in a solution) can be added to the calcium phosphate solution. In some embodiments, silk and the calcium phosphate material can be mixed in a dried state, e.g., powder form, and a liquid added to the mixture to prepare the solution.

Accordingly, in some embodiments, the aqueous solution comprising the silk and the calcium phosphate material is prepared by adding the calcium phosphate material as dry powder or as solution to an aqueous silk solution. It is to be understood that order of adding the silk and the calcium phosphate into the solution is not important for the methods described herein. Thus, in some embodiments, silk is added to a solution of calcium phosphate solution as a solid (e.g., powder) or as an aqueous solution. In some further embodiments of these, the method further comprises adding additional aqueous material (e.g., water) to obtain a solution having a paste (or paste-like) consistency.

In some embodiments, the silk and the calcium phosphate are mixed together in solid form (e.g., powders or resins) and a liquid carrier (e.g., water or an equivalent solvent) added to the mixture to obtain a solution comprising the silk fibroin and the calcium phosphate. The solid form is understood to include and be defined as materials with a consistency of: powders, particle, resins fibers, and the like. For example, solid form silk can be obtained using methods known in the art for producing silk particles or silk powder, including grinding, blending, ball milling, and the like. Silk fibers can be formed by alkaline hydrolysis of silk fibroin into micron-size fibers. Silk particles and fibers and calcium phosphate particles are described below.

In some embodiments, the solution comprising the silk and the calcium phosphate material has a paste (or paste-like) consistency. In some embodiments, paste (or paste-like) consistency means that the solution is malleable or moldable. Paste consistency can be stated in terms of the viscosity of the solution. In some embodiments, viscosity of the solution comprising the silk and the calcium phosphate material can range from about 0.1 to about 250 Pa·s, from about 0.2 to about 150 Pa·s, from about 0.3 to about 100 Pa·s, from about 0.4 to about 50 Pa·s, or from about 0.5 to about 25 Pa·s. Solutions with overly high viscosity can be difficult to spread, smooth, and shape, while those with excessively low viscosity can be difficult to handle for molding purposes. Without limitations, silk-calcium phosphate solutions of higher viscosity, e.g., 100 Pa·s or higher, can be used for preparing green bodies that can be machined into a desired shape post-sintering. In some embodiments, the higher viscosity silk-calcium phosphate solution has a viscosity of about 100 Pa·s to about 500 Pa·s, about 125 Pa·s to about 475 Pa·s, about 150 Pa·s to about 450 Pa·s, about 175 Pa·s to about 425 Pa·s, about 200 Pa·s to about 400 Pa·s, about 225 Pa·s to about 375 Pa·s, or about 250 Pa·s to about 350 Pa·s. Silk/CaP solutions of lower viscosity, e.g., 99 Pa·s, or lower, can be used for injection molding into molds of predetermined shape and structure for preparing the green body. In some embodiments, the lower viscosity calcium phosphate solution has a viscosity of about 0.1 Pa·s to about 80 Pa·s, about 0.5 Pa·s to about 75 Pa·s, about 0.75 Pa·s to about 65 Pa·s, or about 1 Pa·s to about 50 Pa·s. In some embodiments, viscosity of the solution comprising the silk and the calcium phosphate material can range from about 250 cP to 4,000 cP or about 500 cP to about 10,000 cP. In some embodiments, viscosity of the solution comprising the silk and the calcium phosphate material can range from about 1 cP to about 75 cP.

In some embodiments, the viscosity of the solution comprising the silk and the calcium phosphate material can range from about from about 50 cP to about 7000 cP. In some embodiments, the viscosity can range from about 10,000 cP to about 200,000 cP. Without wishing to be bound by a theory, one can pick a particular silk boil time, CaP/silk ratio, and P/L ratio to obtain the desired viscosity from as low as 20-50 cP (0.02-0.05 Pa·s) to as high as 200,000-300,000 cP (200-300 Pa·s).

Viscosity can be measured with various types of viscometers and rheometers. A rheometer is generally used for those fluids which cannot be defined by a single value of viscosity and therefore require more parameters to be set and measured than is the case for a viscometer. In some embodiments, viscosity can be determined at room temperature.

Generally, the solution can comprise any ratio of silk/CaP at any consistency/viscosity since any amount of water (or other aqueous solvent) can be added or removed from a mixture of silk and CaP to get the silk and CaP to dissolve/mix together. For example, the ratio of silk to calcium phosphate material in the solution can range from about 1000:1 to about 1:1000. The ratio can be based on weight or moles. In some embodiments, the ratio of silk to calcium phosphate material in the solution can range from about 500:1 to about 1:500 (w/w), from about 250:1 to about 1:250 (w/w), from about 50:1 to about 1:200 (w/w), from about 10:1 to about 1:150 (w/w) or from about 5:1 to about 1:100 (w/w). In some embodiments, ratio of silk to calcium phosphate material in the solution can be about 1:99 (w/w), about 1:4 (w/w), about 2:3 (w/w), about 1:1 (w/w) or about 4:1 (w/w). In some embodiments, CaP to silk ratio is 100/0, 99/1, 90/10, 80/20, 70/30, 60/40, 50/50, 40/60, 30/70, 20/80, 10/90, 1/99, or 0/100.

In some embodiments, the silk/CaP composition is substantially dry or substantially free of solvents. For example, the composition can be a dry mixture comprising silk and the calcium phosphate material. As used herein, the term "substantially free" means relatively little to no amount of any liquid content in the composition. In some embodiments, a composition substantially free of solvent has a solvent content of less than 5 wt %, less than 4.5 wt %, less than 4 wt %, less than 3.5 wt %, less than 3 wt %, less than 2.5 wt %, less than 2 wt %, less than 1.5 wt %, less than 1 wt %, less than 0.75 wt %, less than 0.5 wt %, less than 0.25 wt %, less than 0.125 wt %, or less than 0.1 wt %.

In some embodiments, the silk/CaP composition can comprise one or more (e.g., one, two, three, four, five or more) additives. Without limitations, presence of one or more additives in the silk/CaP composition used to prepare the ceramic material can alter the release kinetics of a biologically active agent to form a drug delivery compositions based on or comprising the ceramic material described herein. Without wishing to be bound by a theory, presence of additives in the drug delivery composition can provide a diffusion barrier to regulate the release of the therapeutic agent from the composition. The additive can be covalently or non-covalently linked with silk fibroin and can be integrated homogenously or heterogeneously within the ceramic material.

In some embodiments, the additive can be coated on a surface of the ceramic material or infused within the pores of the ceramic material. In some embodiments, the additive can be silk, e.g., silk fibroin. For example, the silk as an additive can be coated on the ceramic. The silk coating layer can comprise an active agent. This can be used for controlled release of the active agent and/or to provide further biocompatibility to the ceramic. Silk coating layers and methods of preparing the same are described, for example, in U.S. Pat. No. 8,354,501, content of which is incorporated herein by reference.

An additive can be selected from small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; glycogens or other sugars; immunogens; antigens; an extract made from biological materials such as bacteria, plants, fungi, or animal cells; animal tissues; naturally occurring or synthetic compositions; and any combinations thereof. Total amount of additives in the solution can be from about 0.1 wt % to about 70 wt %, from about 5 wt % to about 60 wt %, from about 10 wt % to about 50 wt %, from about 15 wt % to about 45 wt %, or from about 20 wt % to about 40 wt %, of the total silk fibroin in the solution.

In some embodiments, an additive is a biocompatible polymer. Exemplary biocompatible polymers include, but are not limited to, a poly-lactic acid (PLA), poly-glycolic acid (PGA), poly-lactide-co-glycolide (PLGA), polyesters, poly(ortho ester), poly(phosphazine), poly(phosphate ester), polycaprolactone, gelatin, collagen, fibronectin, keratin, polyaspartic acid, alginate, chitosan, chitin, hyaluronic acid, pectin, polyhydroxyalkanoates, dextrans, and polyanhydrides, polyethylene oxide (PEO), poly(ethylene glycol) (PEG), triblock copolymers, polylysine, alginate, polyaspartic acid, any derivatives thereof and any combinations thereof. Other exemplary biocompatible polymers amenable to use according to the present disclosure include those described for example in U.S. Pat. No. 6,302,848; U.S. Pat. No. 6,395,734; U.S. Pat. No. 6,127,143; U.S. Pat. No. 5,263,992; U.S. Pat. No. 6,379,690; U.S. Pat. No. 5,015,476; U.S. Pat. No. 4,806,355; U.S. Pat. No. 6,372,244; U.S. Pat. No. 6,310,188; U.S. Pat. No. 5,093,489; U.S. Pat. No. 387,413; U.S. Pat. No. 6,325,810; U.S. Pat. No. 6,337,198; U.S. Pat. No. 6,267,776; U.S. Pat. No. 5,576,881; U.S. Pat. No. 6,245,537; U.S. Pat. No. 5,902,800; and U.S. Pat. No. 5,270,419, content of all of which is incorporated herein by reference.

In some embodiments, the biocompatible polymer is PEG or PEO. As used herein, the term "polyethylene glycol" or "PEG" means an ethylene glycol polymer that contains about 20 to about 2000000 linked monomers, typically about 50-1000 linked monomers, usually about 100-300. PEG is also known as polyethylene oxide (PEO) or polyoxyethylene (POE), depending on its molecular weight. Generally PEG, PEO, and POE are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. Different forms of PEG are also available, depending on the initiator used for the polymerization process—the most common initiator is a monofunctional methyl ether PEG, or methoxypoly(ethylene glycol), abbreviated mPEG. Lower-molecular-weight PEGs are also available as purer oligomers, referred to as monodisperse, uniform, or discrete PEGs are also available with different geometries.

As used herein, the term PEG is intended to be inclusive and not exclusive. The term PEG includes poly(ethylene glycol) in any of its forms, including alkoxy PEG, difunctional PEG, multiarmed PEG, forked PEG, branched PEG, pendent PEG (i.e., PEG or related polymers having one or more functional groups pendent to the polymer backbone), or PEG With degradable linkages therein. Further, the PEG backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)m in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as biocompatible polymers.

Some exemplary PEGs include, but are not limited to, PEG20, PEG30, PEG40, PEG60, PEG80, PEG100, PEG115, PEG200, PEG 300, PEG400, PEG500, PEG600, PEG1000, PEG1500, PEG2000, PEG3350, PEG4000, PEG4600, PEG5000, PEG6000, PEG8000, PEG11000, PEG12000, PEG15000, PEG 20000, PEG250000, PEG500000, PEG100000, PEG2000000 and the like. In some embodiments, PEG is of MW 10,000 Dalton. In some embodiments, PEG is of MW 100,000, i.e. PEO of MW 100,000.

In some embodiments, the additive is a silk fiber. Methods for preparing silk fibroin fibers are well known in the art. In some embodiments, the silk fibers are microfibers or nanofibers. In some embodiments, the additive is micron-sized silk fiber (10-600 µm). Micron-sized silk fibers can be obtained by hydrolyzing the degummed silk fibroin or by increasing the boing time of the degumming process. Alkali hydrolysis of silk fibroin to obtain micron-sized silk fibers is described for example in Mandal et al., PNAS, 2012, doi: 10.1073/pnas.1119474109; U.S. Provisional Application No. 61/621,209, filed Apr. 6, 2012; and PCT application no. PCT/US13/35389, filed Apr. 5, 2013, content of all of which is incorporated herein by reference. Because regenerated silk fibers made from silk solutions are mechanically strong, the regenerated silk fibers can also be used as an additive. In some embodiments, the silk fiber can be prepared by electrospinning a silk solution, drawing a silk solution, and the like. Electrospun silk materials, such as fibers, and methods for preparing the same are described, for example in WO2011/008842, content of which is incorporated herein by reference in its entirety.

In some embodiments, the silk fiber is an unprocessed silk fiber, e.g., raw silk or raw silk fiber. The term "raw silk" or "raw silk fiber" refers to silk fiber that has not been treated to remove sericin, and thus encompasses, for example, silk fibers taken directly from a cocoon. The term "unprocessed silk fiber" refers to a silk fibroin fiber, obtained directly from raw silkworm cocoons or spider silk fibers. A regenerated or processed silk fiber on the other hand comprises silk fibroin fibers obtained from a reconstituted silk fibroin solution and have a substantial silk II or beta-sheet crystallinity only if post-process treated with to induce beta-sheet crystallinity in the silk fibroin. Exemplary methods of inducing beta-sheet crystallinity are described elsewhere in the disclosure.

In some embodiments, the additive is a silk microsphere or nanospheres. Various methods of producing silk microparticles or nanoparticles are known in the art and are described elsewhere in the disclosure.

For forming the green body, the silk/CaP composition can be present in a mold. As used herein, the term "mold" is intended to encompass any mold, container or substrate capable of shaping, holding or supporting the solution comprising the silk and the calcium phosphate. Thus, the mold in its simplest form could simply comprise a supporting surface. The mold can be any desired shape, and can be fabricated from any suitable material including polymers (such as polysulphone, polypropylene, polyethylene), metals (such as stainless steel, titanium, cobalt chrome), ceramics (such as alumina, zirconia), glass ceramics, and glasses (such as borosilicate glass). In some embodiments, the method comprises transferring the composition to the mold, e.g., for forming the green body.

The silk/CaP composition, e.g. in the mold, can be incubated at an elevated temperature and/or in mild heat conditions to produce the stabilized green body. Without wishing to be bound by a theory, when subjected to mild heat the silk-calcium phosphate paste hardens and resulting silk/CaP green body is stabilized by the cured silk. Further, the silk acts as a sacrificial polymer during sintering to generate porosity in the finished ceramic scaffold. Without limitations, the silk/CaP composition, e.g. in the mold, can be incubated at temperature higher than about 30° C. In some embodiments, the silk/CaP composition, e.g. in the mold, can be incubated at a temperature from about 30° C. to about 100° C., from about 35° C. to about 95° C., or from about 40° C. to about 85° C., from about 45° C. to about 75° C., from about 50° C. to about 70° C., or from about 55° C. to about 65° C. In some embodiments, the silk/CaP composition, e.g. in the mold, can be incubated at a temperature of about 60° C.

For forming the stabilized green body, the silk/CaP composition, e.g. in the mold, can be incubated for a period of about 1 hour or more (e.g., 1 hour, 2 hours, 3 hours, 4 hours, 5 hours, 6 hours, 7 hours, 8 hours, 9 hours, 10 hours, 11 hours, 12 hours, 18 hours, 24 hours, 2 days, 3 days, 4 days, 5 days, 7 days, 2 weeks, 3 weeks, 4 weeks, or more). In some embodiments, silk/CaP composition, e.g. in the mold, can be incubated for a period of about 24 hours.

In some embodiments, silk/CaP composition, e.g. in the mold, can be incubated at a temperature of about 60° C. for about 24 hours.

In some embodiments, a stabilized green body can be formed by freeze-drying the CaP-silk composition, i.e., the silk-CaP composition for preparing the green body, in the mold containing the composition. For example, the mold containing the CaP-silk composition can be cooled to a temperature below 0° C. for a period of time before removing the liquid carrier, e.g., water, from the composition. In some embodiments, the composition can be cooled to a temperature of about −5° C., about −10° C., about −15° C., about −20° C., about −25° C. or below for before removing the liquid carrier. Without limitations the composition can be cooled for any period. For example, the composition can be cooled for 1 hour, 2 hours, 4 hours, 6 hours, 12 hours, 18 hours, 24 hours, 30 hours, 36 hours, 42 hours, 48 hours, 54 hours, 60 hours, 66 hours, 72 hours or more. In some embodiments, the composition can be cooled to a temperature of about −20° C. for a period of about 24 hours.

After cooling, liquid carrier can be removed, at least partially, by sublimation, evaporation, and/or lyophilization. In some embodiments, the liquid carrier can be removed under reduced pressure. In some embodiments, the liquid carrier can be removed by lyophilization at a pressure of about 0.006 Torr to about 150 Torr, about 50 Torr to about 125 Torr, or about 95 Torr to about 105 Torr. In some embodiments, the liquid carrier can be removed by lyophilization at a pressure of about 0.006 to 100 Torr. In some embodiments, the liquid carrier can be removed by lyophilization at a pressure of about 100 Torr.

In some embodiments, the stabilized green body can be produced by compressing the silk/CaP composition by applying pressure to the composition. For example, a dry composition, e.g., a composition substantially free of solvent, can be compressed by applying pressure to the composition, e.g., uniaxial dry pressing. When the composition is compressed, its volume is reduced. Thus, additional silk/CaP composition can be added to the mold and pressure applied again. This process can be repeated as many times as needed to obtain a green body of desired size. In some embodiments, the addition and applying step can be repeated at least 1 time, e.g., 1, 2, 3, 4, 5, 6, 7, 8, 9, 10, 11, 12, 13, 14, 15, 16, 17, 18, 19, 20 or more times. The green bodies obtained by applying pressure to the silk/CaP compositions are also referred to as pressed green bodies herein.

Pressure to be applied can range from 500 psi and higher. For example, the pressure to be applied to the composition for forming the stabilized green body can be in the range from about 1,000 psi to about $10^6$ psi. In some embodiments, the pressure to be applied to the composition for forming the stabilized green body can be in the range from about 5,000 psi to about 500,000 psi. In some embodiments, the pressure to be applied to the composition for forming the stabilized green body can be in the range from about 7,500 psi to about 100,000 psi. In one embodiment, the pressure to be applied to the composition for forming the stabilized green body can be in the range from about 10,000 psi to about 20,000 psi.

Further, the pressure can be applied for seconds to hours. For example, the pressure can be applied for about 5 seconds to about 24 hours. In some embodiments, the pressure can be applied from about 5 seconds to about 12 hours, from about 5 seconds to about 6 hours, from about 5 seconds to about 2 hours, from about 5 seconds to about 1 hour, from about 5 seconds to about 45 minutes, from about 5 seconds to about 30 minutes, from about 5 seconds to about 15 minutes, from about 5 seconds to about 10 minutes, from about 5 seconds to about 5 minutes, from about 5 seconds to about 1 minute, from about 5 seconds to about 45 seconds. In some embodiments, the pressure can be applied for about 30 seconds.

The stabilized green body can also be produced using methods other than incubating the composition in the mold at an elevated temperature, in mild heat conditions, lyophilizing, and/or pressure molding. For example, the green body can be produced using one of the following methods:
  (i) Isostatic pressing—(both cold and hot). Powder compaction method that involves applying pressure to the ceramic material from all direction via a liquid or gaseous medium as a means of compacting that part to form a green body.
  (ii) Extrusion—(Direct or indirect). Uses a piston and mechanical force to push a ceramic paste through an orifice or opening to create the shaped green part.

(iii) Slip Casting—The ceramic slurry is poured into a mold made of a highly macroporous material that can absorb the solvent component leaving behind the consolidated green body part.

(iv) Tape Casting—A thin film of ceramic slurry is formed over a flat surface and the solvent is evaporated leaving behind a thin ceramic sheet in the green state.

(v) 3D Printing—While 3D printing of silk-CaP mixtures is known in the art, the art does not disclose sintering the 3D printed green body. Thus, the art does not disclose using silk as a porogen, i.e., no sintering of the silk to burn it off (vi) Extrusion molding.

Without wishing to be bound by a theory, it is believed that stabilizing the green body induces a conformational change in the silk fibroin present in the green body. The induced conformational change alters the crystallinity of the silk fibroin, e.g., silk II beta-sheet crystallinity. The conformational change can be induced by any methods known in the art, including, but not limited to, alcohol immersion (e.g., ethanol, methanol), water annealing, shear stress, ultrasound (e.g., by sonication), pH reduction (e.g., pH titration and/or exposure to an electric field) and any combinations thereof. For example, the conformational change can be induced by one or more methods, including but not limited to, controlled slow drying (Lu et al., Biomacromolecules 2009, 10, 1032); water annealing (Jin et al., 15 Adv. Funct. Mats. 2005, 15, 1241; Hu et al., Biomacromolecules 2011, 12, 1686); stretching (Demura & Asakura, Biotech & Bioengin. 1989, 33, 598); compressing; solvent immersion, including methanol (Hofmann et al., J Control Release. 2006, 111, 219), ethanol (Miyairi et al., J. Fermen. Tech. 1978, 56, 303), glutaraldehyde (Acharya et al., Biotechnol J. 2008, 3, 226), and 1-ethyl-3-(3-dimethyl aminopropyl) carbodiimide (EDC) (Bayraktar et al., Eur J Pharm Biopharm. 2005, 60, 373); pH adjustment, e.g., pH titration and/or exposure to an electric field (see, e.g., U.S. Patent App. No. US2011/0171239); heat treatment; shear stress (see, e.g., International App. No.: WO 2011/005381), ultrasound, e.g., sonication (see, e.g., U.S. Patent Application Publication No. U.S. 2010/0178304 and International App. No. WO2008/150861); and any combinations thereof. Content of all of the references listed above is incorporated herein by reference in their entirety.

In some embodiments, the conformation of the silk fibroin can be altered by water vapor annealing. Without wishing to be bound by a theory, it is believed that physical temperature-controlled water vapor annealing (TCWVA) provides a simple and effective method to obtain refined control of the molecular structure of silk biomaterials, e.g., green bodies disclosed herein. The silk materials can be prepared with control of crystallinity, from a low content using conditions at 4° C. (a helix dominated silk I structure), to highest content of ~60% crystallinity at 100° C. (β-sheet dominated silk II structure). This physical approach covers the range of structures previously reported to govern crystallization during the fabrication of silk materials, yet offers a simpler, green chemistry, approach with tight control of reproducibility. Temperature controlled water vapor annealing is described, for example, in Hu et al., Biomacromolecules, 2011, 12(5): 1686-1696, content of which is incorporated herein by reference in its entirety.

In some embodiments, the green body can be treated with an alcohol, e.g., methanol, ethanol, isopropanol, etc. The alcohol concentration can be at least 10%, at least 20%, at least 30%, at least 40%, at least 50%, at least 60%, at least 70%, at least 80%, at least 90% or 100%. In some embodiment, alcohol concentration is about 90%.

Alternatively, the alteration in the conformation of the silk fibroin in the green body can be induced by treating the CaP-silk composite with shear stress. The shear stress can be applied, for example, by passing the CaP-silk composite solution through a needle. Other methods of inducing conformational changes include contacting the CaP-silk composite solution with an electric field, salt or by applying pressure to the molded CaP-silk green body.

The treatment time for inducing the conformational change can be any period of time necessary to provide a desired silk II (beta-sheet crystallinity) content. In some embodiments, the treatment time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours.

When inducing the conformational change by solvent immersion, treatment time can range from minutes to hours to days. For example, immersion in the solvent can be for a period of at least about 15 minutes, at least about 30 minutes, at least about 1 hour, at least about 2 hours, at least 3 hours, at least about 6 hours, at least about 18 hours, at least about 12 hours, at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, immersion in the solvent can be for a period of about 12 hours to about seven days, about 1 day to about 6 days, about 2 to about 5 days, or about 3 to about 4 days.

Without limitations, the green body can comprise a silk II beta-sheet crystallinity content of at least about 5%, at least about 10%, at least about 20%, at least about 30%, at least about 40%, at least about 50%, at least about 60%, at least about 70%, at least about 80%, at least about 90%, or at least about 95% but not 100% (i.e., all the silk is present in a silk II beta-sheet conformation). In some embodiments, the silk in the green body is present completely in a silk II beta-sheet conformation, i.e., 100% silk II beta-sheet crystallinity.

The stabilized green body can be at least partially sintered to form the porous ceramic blanks having the desired final density. Without limitations, the green bodies can be stored (e.g., at room temperature) before sintering. Due to the stabilization of the silk component in the green body, the green bodies are also stable in aqueous solution for a period of several months without re-dissolution of the calcium phosphate component.

The term "sintering" as used herein means densification of a particulate component involving removal of at least a portion of the pores between the starting particles (accompanied by shrinkage) combined with coalescence and bonding between adjacent particles. As used herein, the term "fully sintered" means sintered to a desired final density, which can or cannot be fully dense. In other words, a fully sintered body can have some residual porosity therein.

The green body can be sintered in a furnace. The sintering can be conducted in an oxygen atmosphere or inert atmosphere. Without wishing to be bound by a theory, introduction of oxygen gas enables the resulting sintered body to be sufficiently dense. Generally, the sintering temperature can be in the range from about 1000° C. to about 1500° C. In some embodiments, the sintering temperature can range from about 1100° C. to about 1500° C., from about 1250° C. to about 1500° C., from about 1350° C. to about 1450° C., or from about 1300° C. to about 1400° C. Sintering can be done with pressure (also known as hot pressing) or without pressure. Without wishing to be bound by a theory, hot pressing can allow use of lower sintering temperatures. In some embodiments, sintering can be done under pressure and the sintering temperature can range from about 600° C. to about 1000° C. Without wishing to be bound by a theory, higher sintering temperature provides ceramic material of higher strength but lower porosity. Thus, the sintering temperature can be optimized to obtain ceramic material of desired strength and/or porosity.

In some embodiments, sintering can be selective laser sintering. Selective laser sintering uses a high power laser to fuse small particles of material together into a desired complex 3D shape. Without wishing to be bound by a theory, this could be used after any of the green body fabrication methods to sinter off only portion of the silk. This enables creating different gradients of porosity within the ceramic.

In some embodiments, sintering can be spark plasma sintering, also called pulsed electric current sintering. The microspark discharge that is emitted in the gaps between the adjacent ceramic grains of the green body is due to the applied current and caused thermal transition to occur which results in partial grain coalescence.

The sintering time can range from 1 hour or longer in order to obtain a sufficient densification effect. In some embodiments, the sintering time can range from about 1 hour to about 12 hours, from about 1 hour to about 6 hours, from about 1 hour to about 5 hours, from about 1 hour to about 4 hours, or from about 1 hour to about 3 hours. In some embodiments, the sintering time can range from about 2 hours to about 4 hours or from 2.5 hours to about 3.5 hours. In some embodiments, the sintering time can be about 3 hours.

As sintering involves densification and removal of porosity within a structure, the structure being sintered can shrink during a sintering process. As a result, dimensional shrinkage may need to be considered and accounted for when designing porous materials of desired geometry. During sintering, the green bodies being sintered can be supported on a support structure within a sintering furnace. As the green body is sintered, friction or "drag" between the abutting surfaces of the green bodies and the support structure can prevent regions of the green bodies proximate the abutting surfaces from shrinking in a manner consistent with the remainder of the green body. As a result, the fully sintered structure may not exhibit the desired geometry, and/or certain dimensions of the fully sintered structure may not be within acceptable tolerance ranges.

Methods for reducing the friction or drag between parts being sintered and the supporting structure are known in the art. For example, it is known to incorporate a sacrificial support surface as an integral part to the geometry of a green body. It is also known to spread powder material on the surface of the support structure, and allowing green parts to rest on the powder material over the surface of the support structure, such that the powder material allows the green parts to slide relative to the surface of the support structure as they shrink during sintering. U.S. Pat. No. 4,886,639 to Andrees et al. discloses methods for sintering components in which the components are suspended during sintering in an effort to ensure uniform shrinkage of the components and to reduce surface cracks. U.S. Pat. No. 7,108,827 to Hata et al. discloses a method of forming a ceramic sheet in which a green sheet is sintered on a spacer sheet that includes spherical ceramic particles having an average particle diameter of 0.1 to less than 5 microns. By using the spacer sheet to support the green sheet, the green sheet slides smoothly on the surface of the spacer sheet when the green sheet shrinks, and the friction resistance between the green sheet and the spacer sheet is lowered. U.S. Pat. No. 7,144,548 to Billiet et al. discloses processing green bodies in a dynamic pressurized supercritical fluid medium such that the bodies remain in a state of buoyancy or weightlessness throughout the sintering process.

In some embodiments, volume or mass of the green body is reduced when the green body is sintered. For example, the green body can reduce in volume or mass by about 50% to about 80% of the original volume or mass. In some embodiments, the green body can reduce in volume or mass by about 55% to about 75% or by about 60% to about 70% of the original volume or mass. The inventors have discovered that mass change is greater for lower calcium phosphate to silk ratios; however, volume change is similar for all calcium phosphate to silk ratios. Without wishing to be bound by a theory, it is believed that the silk component is removed during sintering, leaving behind a higher degree of porosity in green bodies that contain higher mass percentages of silk.

When the green body is processed into a desire shape before sintering, volume or mass of the processed green body is reduced when the green body is sintered. For example, the processed green body can reduce in volume or mass by about 5% to about 30% of the original volume or mass. In some embodiments, the processed green body can reduce in volume or mass by about 10% to about 20% of the original volume or mass.

In some embodiments, for forming complex geometry CaP scaffolds, a stable silk/CaP green body blank is formed and then sintered to generate a sintered ceramic blank that can then be machined into the desired complex geometry. For example, a silk/CaP solution of high viscosity (typically of low water, or other aqueous medium, content) can be packed into a mold of simple geometry, e.g., a silicone mold of simple geometry, using any method available to the practitioner. For example, the solution can be transferred to the mold by hand or any other method available to the practitioner. The mold containing the silk/CaP solution can be incubated in mild heat conditions for a period of time to produce the stabilized green body ceramic blank, which can then be sintered at high temperatures to form the CaP ceramic blank. Alternatively, the mold containing the silk/CaP solution can be freeze-dried to produce the stabilized green body ceramic blank, which can then be sintered at high temperatures to form the CaP ceramic blank.

In some embodiments, a silk/CaP solution of high viscosity (typically of low water, or other aqueous medium, content) can be molded into a simple geometry by hand or other mechanical means without transferring the solution to a mold. This shaped solution can be incubated in mild heat conditions for a period of time to produce the stabilized green body ceramic blank, which can then be sintered at high temperatures to form the CaP ceramic blank. Alternatively, the shaped solution can be freeze-dried to produce the stabilized green body ceramic blank, which can then be sintered at high temperatures to form the CaP ceramic blank After high temperature sintering of the ceramic green body blank, the sintered ceramic blank can then be machined into the desired shape. This can be accomplished using a lathe for cutting, sanding, drilling, facing, or turning the ceramic blank into a specific geometry. In higher technology systems, sintered ceramic blanks can be milled using a multi-axis computer numerical control (CNC) milling machine to create either symmetric or asymmetric, complex geometry scaffolds.

In some embodiments, for forming complex geometry CaP scaffolds, a stable silk/CaP green body of desired final shape is formed and then sintered to generate a sintered ceramic of the desired complex geometry. For example, a silk/CaP solution of low viscosity (typically of high water, or other aqueous medium, content) can be transferred into a mold of a pre-defined geometry. For example, the solution can be transferred to the mold by any other method available to the practitioner. In some embodiments, the solution can be transferred to the mold by injection, i.e., injection molding. Generally, the injection molding technique involves leveraging high pressure to fill a mold cavity with the silk/CaP composite solution. It is to be understood that molding techniques other than injection molding can also be used for forming the green body. For example, one can use blow molding, compaction plus sintering, compression molding, expandable bead molding, xxtrusion molding, foam molding, laminating, reaction injection molding, matched mold, matrix molding, pressure plug assist molding, rotational molding (or Rotomolding), transfer molding, thermoforming, vacuum forming (a simplified version of thermoforming), vacuum plug assist molding, and any combinations thereof.

The mold containing the silk/CaP solution can be incubated in mild heat conditions for a period of time to produce stabilized green bodies of complex shape, which can then be sintered at high temperatures to form the finish CaP ceramic bodies. Alternatively, the mold containing the silk/CaP solution can be freeze-dried to produce the stabilized green bodies of complex shape, which can then be sintered at high temperatures to form the finish CaP ceramic bodies.

In some embodiments, sintering of the green body is not needed or required. For example, when a reactive calcium phosphate material is used, the silk/CaP material can set and/or harden on its own, thereby forming the green body blank of sufficient mechanical strength for processing to a desired shape. In some embodiments, the composition comprising silk and the reactive calcium phosphate material can be used for injection molding.

Exemplary Embodiments of the Method to Create Complex Geometry CaP Scaffolds Via Machining of Sintered CaP Blanks:

In some embodiments, the method comprises:
(i) providing a composition comprising silk and a calcium phosphate material, wherein the composition is present in a simple geometry mold and wherein the composition has a high viscosity, e.g., paste or paste-like consistency;
(ii) forming a green body ceramic blank;
(iii) sintering the green body; and
(iv) processing the resultant sintered CaP ceramic blank into a desired complex geometry scaffold.

In some further embodiments of the above, forming the green body blank comprises incubating the mold from step (i) at about 60° C. for about 24 hours to produce a green body ceramic blank.

In some further embodiments of the above, forming the green body blank comprises freeze-drying the composition in the mold from step (i). For example, by freezing the composition in the mold from step (i) at about −20° C. for about 24 hours and lyophilizing the frozen composition at about 0.006-100 Torr for about 24-48 hours to produce the green body ceramic blank.

In some further embodiments of the above, sintering the green body blank is at a temperature of about 1300° C.-1400° C. for about 2-3 hours.

In some embodiments, the method comprises:
(i) preparing a composition comprising silk and a calcium phosphate material, wherein the composition has a high viscosity, e.g., paste or paste-like consistency;
(ii) transferring the composition of step (i) into a simple geometry mold;
(iii) incubating the mold from step (ii) at about 60° C. for about 24 hours to produce a green body ceramic blank;
(iv) optionally storing the green body ceramic blank, e.g., at room temperature;
(v) sintering the green body blank at a temperature of about 1300° C.-1400° C. for about 2-3 hours, e.g., with a linear ramp heating rate of about 8° C./minute; and.
(vi) processing, e.g., machining the resultant sintered CaP ceramic blank into a desired complex geometry scaffold.

In some other embodiments, the method comprises:
(i) preparing a composition comprising silk and a calcium phosphate material, wherein the composition has a high viscosity, e.g., paste or paste-like consistency;
(ii) transferring the composition of step (i) into a simple geometry mold;
(iii) freeze-drying the solution in the mold from step (ii), e.g., by freezing the composition in the mold from step (iii) at about −20° C. for about 24 hours and lyophilizing the frozen composition at about 0.006-100 Torr for about 24-48 hours to produce a green body ceramic blank;
(iv) optionally storing the green body blank, e.g., at room temperature;
(v) sintering the green body blank at a temperature of about 1300° C.-1400° C. for about 2-3 hours, e.g., with a linear ramp heating rate of about 8° C./minute; and
(vi) processing, e.g., machining the resultant sintered CaP ceramic blank into the desired complex geometry scaffold.

In some embodiments, the method comprises:
(i) forming a composition comprising silk and a silk phosphate material into a desired shape for processing, wherein the composition has a high viscosity, e.g., paste or paste-like consistency;
(ii) forming a green body ceramic blank;
(iii) sintering the green body; and
(iv) processing the resultant sintered CaP ceramic blank into a desired complex geometry scaffold In some further embodiments of the above, forming the green body blank comprises incubating the shaped composition from step (i) at about 60° C. for about 24 hours to produce a green body ceramic blank.

In some further embodiments of the above, forming the green body blank comprises freeze-drying the shaped composition from step (i). For example, by freezing the at about −20° C. for about 24 hours and lyophilizing the frozen composition at about 0.006-100 Torr for about 24-48 hours to produce the green body ceramic blank.

In some further embodiments of the above, sintering the green body blank is at a temperature of about 1300° C.-1400° C. for about 2-3 hours.

In some embodiments, the method comprises:
(i) preparing a composition comprising silk and a calcium phosphate material, wherein the composition has a high viscosity, e.g., paste or paste-like consistency;
(ii) forming the composition to a desired shape for processing;

(iii) incubating the composition from step (ii) at about 60° C. for about 24 hours to produce a green body ceramic blank;
(iv) optionally storing the green body ceramic blank, e.g., at room temperature;
(v) sintering the green body blank at a temperature of about 1300° C.-1400° C. for about 2-3 hours, e.g., with a linear ramp heating rate of about 8° C./minute; and.
(vi) processing, e.g., machining the resultant sintered CaP ceramic blank into a desired complex geometry scaffold.

In some other embodiments, the method comprises:
(i) preparing a composition comprising silk and a calcium phosphate material, wherein the composition has a high viscosity, e.g., paste or paste-like consistency;
(ii) forming the composition into a desired shape for processing;
(iii) freeze-drying the composition from step (ii), e.g., by freezing the composition in the mold from step (iii) at about −20° C. for about 24 hours and lyophilizing the frozen composition at about 0.006-100 Torr for about 24-48 hours to produce a green body ceramic blank;
(iv) optionally storing the green body blank, e.g., at room temperature;
(v) sintering the green body blank at a temperature of about 1300° C.-1400° C. for about 2-3 hours, e.g., with a linear ramp heating rate of about 8° C./minute; and
(vi) machining the resultant sintered CaP ceramic blank into the desired complex geometry scaffold.

In some embodiments, the green body can be removed from the mold before storing.

In some embodiments, preparing the composition having a high viscosity, e.g., paste or paste-like consistency comprising: (i) mixing a calcium phosphate material in solid form (e.g., powder or particulate) with an aqueous silk solution; and (ii) optionally adding one or more aliquots of a carrier liquid (e.g., water) to form the composition having a high viscosity, e.g., paste or paste-like consistency.

In some embodiments, preparing the composition having a high viscosity, e.g., paste or paste-like consistency comprising: (i) mixing together a calcium phosphate material and silk, wherein the calcium phosphate material and the silk are both in solid form (e.g., powder or particulate); and (ii) adding one or more aliquots of a carrier liquid (e.g., water) to form a composition having a high viscosity, e.g., paste or paste-like consistency.

In some embodiments, processing sintered CaP ceramic blank into the desired complex geometry scaffold comprises machining, turning (lathe), rolling, thread rolling, drilling, milling, sanding, punching, die cutting, blanking, broaching, or any combinations thereof Exemplary Embodiments of the Method to Create Complex Geometry CaP Scaffolds Via Injection Molding of Silk/CaP Composite Solutions:

In some embodiments, the method comprises:
(i) providing a composition comprising silk and a calcium phosphate material, wherein the composition is in a mold or cavity of pre-defined complex shape and wherein the composition has a low viscosity, e.g., slurry or slurry-like consistency;
(ii) forming a green body ceramic blank; and
(iii) sintering the green body.

In some further embodiments of the above, forming the green body blank comprises incubating the composition from step (i) at about 60° C. for about 24 hours to produce a green body ceramic blank.

In some further embodiments of the above, forming the green body blank comprises freeze-drying the composition from step (i). For example, by freezing the at about −20° C. for about 24 hours and lyophilizing the frozen composition at about 0.006-100 Torr for about 24-48 hours to produce the green body ceramic blank.

In some further embodiments of the above, sintering the green body blank is at a temperature of about 1300° C.-1400° C. for about 2-3 hours.

In some embodiments, the method comprises:
(i) preparing a solution comprising silk and a calcium phosphate material, wherein the solution has a low viscosity, e.g., slurry or slurry-like consistency;
(ii) transferring the solution of step (i) into a mold or cavity of pre-defined complex shape, e.g., via injection using high pressure;
(iii) incubating the solution in the mold from step (ii) at about 60° C. for about 24 hours to produce a green body;
(iv) optionally storing the green body, e.g., at room temperature; and
(v) sintering the green body at a temperature of about 1300° C.-1400° C. for about 2-3 hours, e.g., with a linear ramp heating rate of about 8° C./minute.

In some other embodiments, the method comprises:
(i) preparing a solution comprising silk and a calcium phosphate material, wherein the solution has a low viscosity, e.g., slurry or slurry-like consistency;
(ii) transferring the solution of step (i) into a mold or cavity of pre-defined complex shape, e.g., via injection using high pressure;
(iii) freeze-drying the solution in the mold from step (ii), e.g., by freezing the composition in the mold from step (iii) at about −20° C. for about 24 hours and lyophilizing the frozen composition at about 0.006-100 Torr for about 24-48 hours to produce a green body;
(iv) optionally storing the green body, e.g., at room temperature; and
(v) sintering the green body at a temperature of about 1300° C.-1400° C. for about 2-3 hours, e.g., with a linear ramp heating rate of about 8° C./minute.

In some embodiments, the green body can be removed from the mold before storing.

In some embodiments, preparing the composition having a low viscosity, e.g., slurry or slurry-like consistency comprising: (i) mixing a calcium phosphate material in solid form (e.g., powder or particulate) with an aqueous silk solution; and (ii) optionally adding one or more aliquots of a carrier liquid (e.g., water) to form the composition having a low viscosity, e.g., paste or paste-like consistency.

In some embodiments, preparing the composition having a low viscosity, e.g., paste or paste-like consistency comprising: (i) mixing together a calcium phosphate material and silk, wherein the calcium phosphate material and the silk are both in solid form (e.g., powder or particulate); and (ii) adding one or more aliquots of a carrier liquid (e.g., water) to form a composition having a low viscosity, e.g., paste or paste-like consistency.

Exemplary Embodiments of the Method to Create Complex Geometry CaP Scaffolds Via Dry Silk/CaP Powder Pressing:

In some embodiments, the method comprises:
(i) providing a composition comprising silk and a calcium phosphate material, wherein the composition is in a mold and wherein the composition is substantially dry or free of solvents;
(ii) forming a green body ceramic blank; and
(iii) sintering the green body.

In some further embodiments of the above, forming the green body blank comprises applying pressure to the composition in the mold to reduce the volume of the composition. The method optionally comprises adding additional composition comprising silk and CaP material to the mold after the volume has been reduce and applying pressure to reduce the volume again. Adding the composition and applying the pressure steps can be repeated until the green body ceramic blank of a desired size is obtained.

In some further embodiments of the above, the green body blank can be processed into a desired final shape before sintering.

In some further embodiments of the above, sintering the green body blank is at a temperature of about 1300° C.-1400° C. for about 2-3 hours.

In some embodiments, the method comprises:
(i) preparing a composition comprising silk and a calcium phosphate material, wherein the composition is dry or substantially free of solvents;
(ii) transferring the composition of step (i) into a mold;
(iii) applying pressure to the composition in the mold, thereby reducing the volume of the composition in the mold;
(iv) optionally adding additional composition comprising silk and the calcium phosphate material to the mold and applying pressure;
(v) repeating step (iv) until a green body ceramic blank of a desires size has been produced;
(vii) optionally storing the green body ceramic blank, e.g., at room temperature;
(viii) optionally processing the green body ceramic blank to a desired shape;
(ix) optionally storing the processed green body blank, e.g., at room temperature; and
(x) sintering the green body blank at a temperature of about 1300° C.-1400° C. for about 2-3 hours, e.g., with a linear ramp heating rate of about 8° C./minute; and.

Silk Powder/Particulate

In some embodiments, the method further comprises preparing a silk powder or particulate, e.g., for preparing the solution comprising the silk and the CaP material. In some embodiments, the method of preparing the silk powder of particulates comprises: (i) freeze-drying a solution of silk to produce a lyophilized silk material, e.g., a sponge or a foam; and (ii) reducing the lyophilized silk material from (i) into a powder or particulates.

Figure 24:
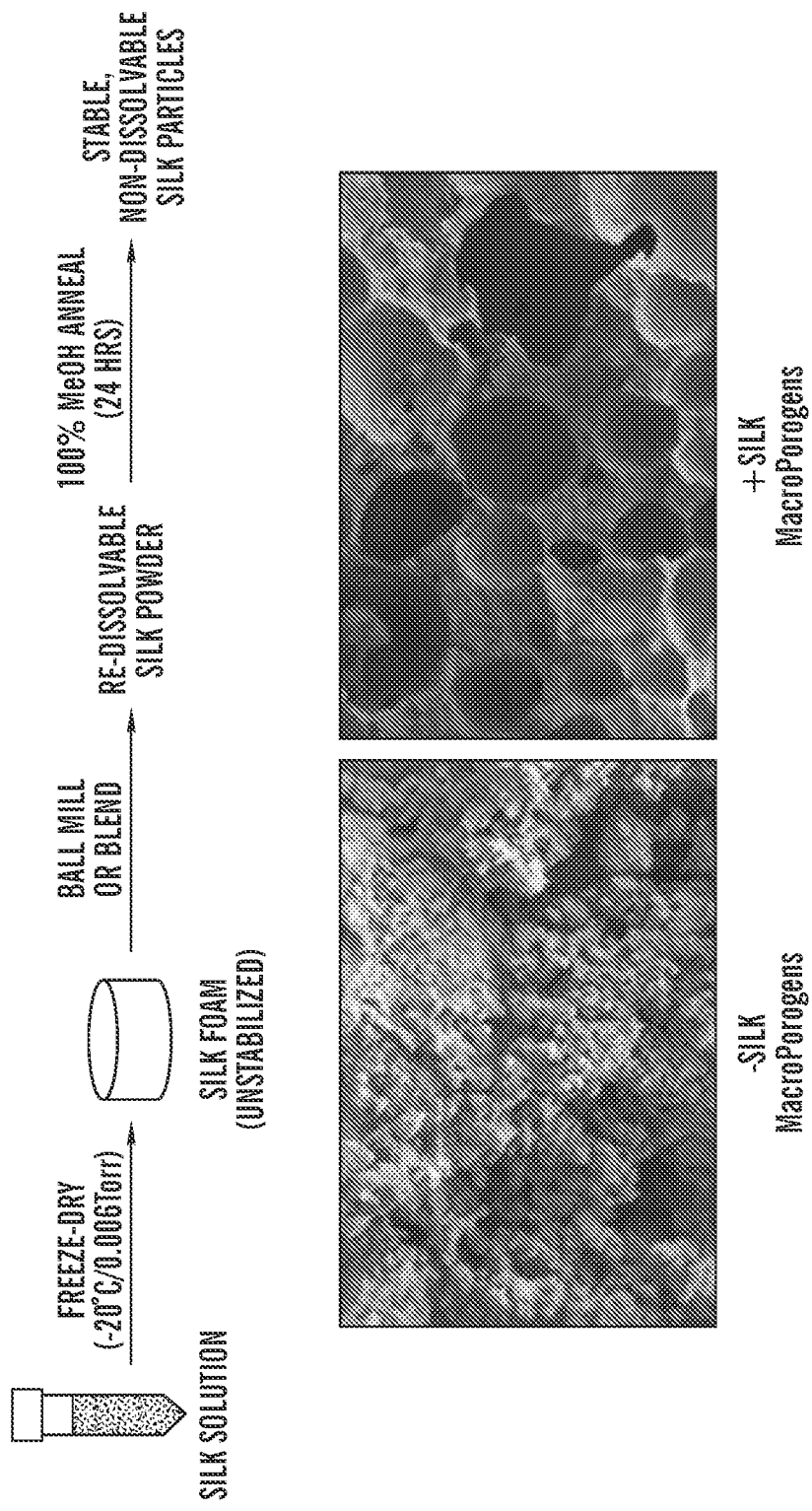
FIG. 24 shows a schematic representation of an embodiment for fabrication of silk macroporogens (top) and SEM imaging of sintered CaP scaffolds prepared according to embodiments of the Silk Solvent Method with the inclusion of silk macroporogens in the green body.

In one embodiment of the method for producing silk powder or particulates, the method comprises: (i) freezing a solution of silk at about −20° C. for about 24 hours; (ii) transferring the frozen silk solution to a temperature of about −80° C. for about 2-3 hours; (iii) lyophilizing the frozen silk solution at a pressures of about 0.006-100 Torr for about 24-48 hours, or until the silk is completely lyophilized; and (iv) reducing the lyophilized silk to silk powder by: (a) blending the lyophilized silk material for 2-3 minutes to generate large particles, or (b) ball milling the lyophilized silk at about 200-350 rpm for about 2-3 hours to generate a fine silk powder. The silk powder or particulate can be stored at room temperature under low humidity conditions. An exemplary embodiment for preparing silk particles is shown schematically in FIG. 24.

Ceramic Material

The disclosure also provides a ceramic material prepared by the method described herein. The ceramic material prepared according the method described herein is biocompatible and/or bioresorbable. The ceramic material can be used as structural bone implants and carrier devices to delivery biomolecules and cells to critical bone defects.

As used herein, the term "biocompatible" refers to a material that does not elicit a substantial immune response in the host.

By "bioresorbable" is meant the ability of a material to be resorbed or remodeled in vivo. The resorption process involves degradation and elimination of the original implant material through the action of body fluids, enzymes or cells in conjunction with the re-integration of host tissue. The resorbed materials can be used by the host in the formation of new tissue, or it can be otherwise re-utilized by the host, or it can be excreted. The ceramic material described herein can have a resorption half-life of approximately 6 months to approximately 12 months. In some embodiments, the material has a resorption half-life of approximately 9 months. The material can be completely resorbed in approximately 12 months to approximately 24 months. In some embodiments the material is completely resorbed in approximately 12 months. Resorbable ceramics are also referred to as "bioceramics".

In some embodiments, the ceramic material is porous. As used herein, the term "porosity" means the fractional volume (dimension-less) of the composition that is composed of open space, e.g., pores or other openings. Thus, porosity measures void spaces in a material and is a fraction of volume of voids over the total volume, as a percentage between 0 and 100% (or between 0 and 1). See for example, Coulson J. M., et al., *Chemical Engineering,* 1978, volume 2, $3^{rd}$ Edition, Pergamon Press, 1978, page 126). The porosity can be optimized by, for example, changing the ratio of silk to the calcium phosphate material in the solution. For example, lower amounts of silk lead to porous materials with low porosity and higher amount of silk can lead to porous materials with high porosity. Determination of matrix porosity is well known to a skilled artisan, e.g., using standardized techniques, such as mercury porosimetry and gas adsorption, e.g., nitrogen adsorption. Generally, porosity of the ceramic material can range from about 0.35 to about 0.85, from about 0.4 to about 0.80, from about 0.45 to about 0.75, or from about 0.5 to about 0.60. In some embodiments, porosity of the ceramic material is less than about 0.7. In some embodiments, porosity of the ceramic material is about 1% to about 25%, about 2% to about 20%, about 1% to about 40%, about 2.5% to about 10%, about 1% to about 7%, about 20% to about 50%, about 15% to about 50%, or about 10% to about 25%. In the exemplary ceramics prepared according to the method disclosed herein, the total porosity range for the Silk Solvent Method was from about 4% to 40%, for the Silk Powder Method about 2% to 15%, for Silk Freeze-Drying from about 20% to 50%, and for Silk Macroporogens from about 50-65%.

The term porous as used herein means that the material can contain macropores and/or micropores. Macroporosity typically refers to features associated with pores on the scale of greater than approximately 10 microns. Microporosity typically refers to features associated with pores on the scale of less than approximately 10 microns. It will be appreciated that there can be any combination of open and closed cells within the material. For example, the material will generally contain both macropores and micropores. The macroporosity is generally open-celled, although there may be a closed cell component. To the inventors' knowledge, this work is the first example of using silk fibroin as a porogen The porous material can have any pore size, e.g., macropore size. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. The pore size range (pore diameter) in the porous material is typically from about 1 to about 1200 microns. For example, from about 10 to about 1000 microns, from about 100 to 800 microns, from about 200 to about 750 microns, from about 300 to 600 microns, or from about 400 to about 500 microns. In some embodiments, the pore size is from about 25 microns to about 250 microns. In some embodiments, the pore size is at least 50 microns, 75 microns, 100 microns, 125 microns, 150 microns, 175 microns, 200 microns, 225 microns, 250 microns, 275 microns, 300 microns or more. In some embodiments, the pore size is less than 1000 microns, 900 microns, 800 micros, 750 microns, 700 microns, 650 microns, 600 microns, 550 microns, 500 microns, 450 microns, 400 microns or less.

In some embodiments, the ceramic material has a pore size of about 20 μm to about 80 μm, about 25 μm to about 40 μm, about 35 μm to about 55 μm, about 60 μm to about 75 μm, about 65 μm to about 70 μm, about 1 μm to about 6 μm, about 1 μm to about 2 μm, about 2 μm to about 4 μm, about 5 μm to about 6 μm, about 1 μm to about 8 μm, about 1.5 μm to about 2.5 μm, about 2 μm to about 3 μm, about 3.5 μm to about 7.5 μm, about 25 μm to about 80 μm, about 20 μm to about 75 μm, about 40 μm to about 200 μm, or about 2.5 μm to about 10 μm. In the exemplary ceramics prepared herein, pore size for the Silk Solvent Method macropores ranged from about 25 to 65 microns and for micropores about 1 to 6 microns. For the Silk Powder Method macropores ranged from about 30 to 100 microns and for micropores about 1 to 9 microns. For the Silk Freeze-Drying macropores ranged from about 50 to 130 microns and for micropores about 3 to 15 microns. For Silk Macroporogens macropore size ranges from about 100 to 300 microns.

Without wishing to be bound by a theory, it is believed that microporosity is established in the ceramics as result of sintering. The sizes of these micropores can range from about 2 to 20 microns. However, other methods can be implemented to achieve pore sizes in the range of 10 to 300 microns, which include mixing salt crystals, sucrose, polymer particles, or even large silk particles or fibers into the silk/CaP solution before molding and sintering.

It will be understood by one of ordinary skill in the art that pores can exhibit a distribution of sizes around the indicated "size." Unless otherwise stated, the term "size" as used herein refers to the mode of a size distribution of pores, i.e., the value that occurs most frequently in the size distribution. The pore size distribution (the standard deviation of the mean pore diameter) in the porous material is generally from about 1 to about 800 microns. In some embodiments, the pore size distribution is from about 5 to about 700 microns, from about 10 to about 600 microns, from about 20 to about 500 microns, from about 30 to about 400 microns, from about 40 to about 300 microns, or from about 50 to about 200 microns. In some embodiments, the pore size distribution is from about 10 to about 200 microns, from about 20 to about 100 microns, or from about 5 to about 75 microns. In some embodiments, the pore size distribution in the porous material is from about 2 microns to about 20 microns, from about 10 microns to about 300 microns, or from about 10 microns to about 400 microns.

The mean aspect ratio range in the porous material is typically from about 1 to about 50. In some embodiments, the mean aspect ratio range in the porous material is typically from about 1 to about 25, from about 1 to about 15, from about 1 to about 5, from about 1 to 2.5, or from about 1 to about 1.5. In some embodiments, the mean aspect ratio range in the porous material is about 1.

In some embodiments, the pores can be intercommunicating pores. The percentage of open-cell porosity (measured as a percentage of the total number of pores both open- and closed-cell, e.g., number of open cells/(number of open cells+number of closed cells)) in the porous material is from about 1 to 100%, from about 20 to 100%, or from about 90 to 100%.

The ceramic materials can uptake water or other liquids without swelling. For example, the ceramic materials can uptake water or other liquid without undergoing substantial change in volume. In some embodiments, the ceramic material has volume swell ratio of 1.5%, 1.25%, 1%, 0.75%, 0.5%, 0.25%, 0.2%, 0.15%, 0.1%, 0.05% or lower. Volume swell ratio can be calculated based on the formula: (Swell volume–dry volume)/dry volume. In some embodiments, the volume swell ratio can range from about 0.5% to about 20%.

In some embodiments, the ceramic materials can uptake about 0.5 wt % to about 25 wt % of water or other liquid without undergoing any significant swelling. For example, the ceramic materials can uptake 0.5 wt % to about 25 wt % with a swell ratio of 1.5% or lower, e.g., 1.25%, 1%, 0.75%, 0.5%, 0.25%, 0.2%, 0.15%, 0.1%, 0.05% or lower. In some embodiments, the ceramic material can uptake about 0.5 wt % to about 20 wt % of water or other fluid/liquid The ceramic materials can have any desired density. For example, the ceramic materials can have a density ranging from about 0.0010 g/cm$^3$ to about 0.0030 g/cm$^3$, from about 0.0015 g/cm$^3$ to about 0.0020 g/cm$^3$, or from about 0.0025 g/cm$^3$ to about 0.0030 g/cm$^3$. Generally, the Silk Freeze-Drying produces much less dense samples than Silk Solvent Method and Silk Powder Methods.

In some embodiments, the ceramic material described herein has compressive strength, compressive toughness and compressive elastic modulus values approximate to those of healthy human bone and enables immediate load bearing. Without wishing to be bound by a theory, load-bearing properties can also prevent unwanted resorption of adjacent bone resulting from high local stress concentration or stress-shielding.

Compressive toughness is the capacity of a material to resist fracture when subjected to axially directed pushing forces. By definition, the compressive toughness of a material is the ability to absorb mechanical (or kinetic) energy up to the point of failure. Toughness is measured in units of joules per cubic meter (Jm$^{-3}$) and can be measured as the area under a stress-strain curve. In some embodiments, the ceramic material described herein has a compressive toughness of about 1 kJm$^{-3}$ to about 20 kJm$^{-3}$ or about 1 kJm$^{-3}$ to approximately 5 kJm$^{-3}$ at 6% strain as measured by the J-integral method. In one embodiment, the ceramic material has a compressive toughness of about 1.3 kJm$^{-3}$, which is the approximate compressive toughness of healthy bone.

Compressive strength is the capacity of a material to withstand axially directed pushing forces. By definition, the compressive strength of a material is that value of uniaxial compressive stress reached when the material fails completely. A stress-strain curve is a graphical representation of the relationship between stress derived from measuring the load applied on the sample (measured in MPa) and strain derived from measuring the displacement as a result of compression of the sample. The ultimate compressive strength of the material can depend upon the target site of implantation. For example, if the material is for placement next to osteoporotic cancellous bone, to avoid high stress accumulation and stress shielding, the ceramic material can comprise a compressive strength (stress to yield point) of approximately 0.1 MPa to approximately 2 MPa. If the ceramic material is intended for placement next to healthy cancellous bone, the material can comprise an ultimate compressive strength (stress to yield point) of approximately 5 MPa. Alternatively, if the material is intended for placement next to cortical bone, the material may comprise an ultimate compressive strength (stress to yield point) of at least 40 MPa.

Generally, the ceramic material described herein comprises an ultimate compressive strength (stress to yield point) of about 5 MPa to about 150 MPa. For example, the ceramic material described herein comprises an ultimate compressive strength of about 20 MPa to approximately 130 MPa, from about 60 MPa to about 130 MPa, or from about 30 to about 50 MPa. In some embodiments, the ceramic material has an ultimate compressive strength of about 5 MPa to about 30 MPa. In some embodiments, the ceramic material described herein comprises an ultimate compressive strength of at least 40 MPa. In one embodiment, the ceramic material described herein comprises an ultimate compressive strength (stress to yield point) of approximately 100 MPa. In some embodiments, the ceramic material described herein has a compressive strength of from about 20 MPa to about 130 MPa at 5% strain. In some embodiments, the ceramic material has a compressive strength of about 5 MPa to about 30 MPa, about 7.5 MPa to about 25 MPa, about 2.5 MPa to about 30 MPa, about 25 MPa to about 150 MPa, about 50 MPa to about 150 MPa. In some embodiments, the ceramic material has a compressive strength similar to the ultimate compression strength of human cortical bone in load bearing bones (e.g. femur, tibia), which is approximately 170-200 MPa. The ceramics materials disclosed herein are suitable and ideal for load-bearing. As you increase the % silk in the green body the resultant sintered ceramic strength decreases down to 50-60 MPa for the Silk Solvent and Silk Powder Methods. The Silk Freeze-Dried scaffolds have a high-end compressive strength of about 40 MPa and a low-end strength of 5 MPa (for the higher % silk scaffolds).

Without wishing to be bound by a theory, ceramics prepared by the method comprising stabilizing the green body by incubating at an elevated temperature have a higher compressive strength than those prepared by the method comprising stabilizing the green body by freeze-drying.

Compressive elastic modulus is the mathematical description of the tendency of a material to be deformed elastically (i.e. non-permanently) when a force is applied to it. The Young's modulus (E) describes tensile elasticity, or the tendency of a material to deform along an axis when opposing forces are applied along that axis; it is defined as the ratio of tensile stress to tensile strain (measured in MPa) and is otherwise known as a measure of stiffness of the material. The elastic modulus of an object is defined as the slope of the stress-strain curve in the elastic deformation region. The ceramic material described herein can comprise a compressive elastic modulus of between approximately 1 GPa and approximately 5 GPa at 5% strain. In some embodiments, the ceramic material described herein comprises a compressive elastic modulus of approximately 3 GPa at 5% strain. In some embodiments, the ceramic material described herein has a mean compressive elastic modulus of between about 2 GPa and about 4 GPa at 5% strain.

In some embodiments, the ceramic material described herein comprises a compressive modulus of about 0.25 GPa to about 2 GPa, about 0.25 GPa to about 1.5 GPa, about 0.25 GPa to about 1.25 GPa, about 0.25 GPa to about 1 GPa, about 2.5 GPa to about 10 GPa, about 4 GPa to about 9 GPa, about 4 GPa to about 8 GPa, about 0.25 GPa to about 1.5 GPa, or about 2.5 GPa to about 10 GPa, about 8 GPa to about 10 GPa.

In some embodiments, f can contain a biological cell. For example, cells can be encapsulated in the finished ceramic material via standard cell seeding techniques. For example, if a reactive, self-setting CaP is mixed with the silk solution and allowed to harden at room temperature, then cells can be encapsulated either into the final CaP-silk solution prior to setting, or in the silk solution prior to mixing with CaP. Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above.

In some embodiments, the ceramic material can contain bone cells. As used herein, a bone cell is any cell that is found in bone. Bone cells include osteoblasts, osteocytes, osteoclasts, osteoprogenitors and bone lining cells. Osteoblasts are commonly called bone-forming cells. They secrete osteoid, which forms the bone matrix. They also begin mineralization. Osteocytes are mature osteoblasts, which no longer secrete matrix, yet are surrounded by it. Osteocytes maintain metabolism, and participate in nutrient/waste exchange via blood. Osteoclasts function in resorption and degradation of existing bone, the opposite of osteoblasts. Osteoprogenitors are immature cells, which differentiate to make osteoblasts. Bone lining cells are quiescent osteoblasts covering the bone. The cell can be added to the ceramic material after formation by immersing the ceramic material in a solution comprising the biological cell or a cell culture.

In some embodiments, the ceramic material described herein is osteoconductive. Generally osteoinductivity relates more to how well the scaffolds can entice the cells to migrate into the scaffold, proliferate, and differentiate. The porosity of a material affects the osteoconductivity of that material. Osteoconductivity can be a function of porosity and/or surface roughness. The CaP scaffolds created using the method disclosed herein are osteoconductive, meaning that they can physically support cells on the material surface.

In some embodiments, the ceramic material described herein is osteoinductive. Osteoinductivity is generally defined as the ability to induce non-differentiated stem cells or osteoprogenitor cells (osteoblasts), which is a component of osseous (bone) tissue, to differentiate into osteoblasts. The simplest test of osteoinductivity is the ability to induce the formation of bone in tissue locations such as muscle, which do not normally form bone (ectopic bone growth). It is generally understood that ceramic materials described herein can be made osteoinductive by adding growth factors such as rhBMP-2 (recombinant human bone morphogenic protein-2) to them. The mineralization and the addition of growth factors can affect the osteoinductivity of a material.

In some embodiments, the ceramic material described herein is osteogenic and shows new bone formation after implantation in vivo. Osteogenesis is the process of laying down new bone material using osteoblasts. Osteoblasts build bone by producing osteoid to form an osteoid matrix, which is composed mainly of type I collagen. Osseous tissue comprises the osteoid matrix and minerals (mostly with calcium phosphate) that form the chemical arrangement termed calcium hydroxyapatite. Osteoblasts are typically responsible for mineralization of the osteoid matrix to form osseous tissue. Without wishing to be bound by a theory, the osteoconductivity and osteoinductivity of the material has an impact on osteogenesis. The material can show new bone formation within 6 months of implantation in vivo. In some embodiments, the material shows new bone formation within 8 weeks of implantation in vivo.

Generally, ceramics can be divided into two broad categories: resorbable and non-resorbable. Non-resorbable ceramics are generally metal oxides (alumina (aluminum oxide), zirconia, titanium oxide, etc), silicates, and nitrides. The non-resorbable ceramics do not dissolve in the body and are inert. They are used mostly as insulators and therefore they do not need to have any porosity (whereas bioceramics do need to have some degree of porosity to support cell ingrowth and nutrient mass transport once they are implanted in the body). Since non-resorbable ceramics are fully dense (essentially 0% porosity) they are very easy to machine, and can be machined into whatever shape you need for a given insulator. However, bioceramics are not so easy to machine due to their porosity. Bioceramics can be made machinable, however, by pressing the material—e.g. uniaxial dry pressing, isostatic pressing, etc. . . . . These processes result in a fully dense part due to such high pressures being applied to the ceramic powder. As a result one obtains a dense bioceramic blank that can be machined. However, the porosity is scarified since the bioceramic is dry pressed and is now fully dense). This is a problem bioceramic pressing faces.

However, in the method disclosed herein the silk acts as an exceptionally good binder for making ceramic green bodies that are very dense, such that, when they are sintered, the silk burns off to leave behind macropores but the ceramic material itself (in between these macropores) is super dense thanks to the consolidation effects of the silk. As a result of this high density, the finished sintered ceramics (that no longer have silk in them) are actually machinable even though they have quite a bit of macroporosity. Inventors discovered that using different embodiments of the method (Silk Solvent, Silk Powder and Silk Freeze-Drying) created ceramics that were machinable (even though they have up to 50-60% total porosity with pore sizes up to 100-150 microns). One can also take CaP and silk powder (in whatever ratio desired) and uniaxially press the dry mixture to create fully dense compacted blank comprised of CaP and silk powder, which can be processed to a desired shape directly (with the silk powder still inside). Further, if one desires more porosity in the material, one can sintered the processed part to remove the silk powder component leaving behind just the calcium phosphate.

Thus, the methods and ceramics disclosed herein is particularly useful for orthopedics. For example, the method and ceramics disclosed herein can be used for making patient specific implants or orthopedics. By way of an example only, a patient comes into the operating room with a certain size defect in a given bone and the surgeon takes the MRI scan (or other imaging analysis) of the defect. The MRI (or other imaging analysis) can be used to create a 3D model of the defect. The 3D model then can be used to create the implant by machining a big block of: either sintered CaP-silk material of a certain porosity (which can be determine by initial silk content and easily prepared using the method disclosed herein) or by machining a block of dry pressed CaP-silk material (with the silk still in it and easily prepared using the method disclosed herein) into the shape dictated by the 3D model for the patient. Machining can be by a multi-axis CNC machine.

In some other embodiments, a patient specific implant or orthopedic can be made by using a composition comprising silk and a reactive calcium phosphate material. The composition can be administered to the defect site. Since the reactive calcium phosphate material can self-set or harden, the defect will be filled with the hardened material.

In some embodiments, the ceramic material described herein can comprise one or more supplementary material. The supplementary material is selected based upon its compatibility with calcium phosphate and the other components and its ability to impart properties (biological, chemical, physical, or mechanical) to the composite, which are desirable for a particular therapeutic purpose or for post-sterilization stability. For example, the supplementary material can be selected to improve tensile strength and hardness, increase fracture toughness, and provide imaging capability of the paste after implantation, hydration, and hardening. The supplementary materials are desirably biocompatible.

The supplementary material can be added to the ceramic material in varying amounts and in a variety of physical forms, dependent upon the anticipated therapeutic use. For example, the supplementary material can be in the form of solid structures, such as sponges, meshes, films, fibers, gels, filaments or particles, including microparticles and nanoparticles. The supplementary material itself can be a composite. The supplementary material can be a particulate or liquid additive or doping agent, which is intimately mixed with the ceramic material.

In many instances, it is desirable that the supplementary material be bioresorbable. Bioresorbable material for use as supplementary material include, without limitation, polysaccharides, nucleic acids, carbohydrates, proteins, polypeptides, poly($\alpha$-hydroxy acids), poly(lactones), poly(amino acids), poly(anhydrides), poly(orthoesters), poly(anhydride-co-imides), poly(orthocarbonates), poly($\alpha$-hydroxy alkanoates), poly(dioxanones), and poly(phosphoesters). Preferably, the bioresorbable polymer is a naturally occurring polymer, such as collagen, glycogen, chitin, starch, keratins, silk, demineralized bone matrix, and hyaluronic acid; or a synthetic polymer, such as poly(L-lactide) (PLLA), poly(D, L-lactide) (PDLLA), polyglycolide (PGA), poly(lactide-co-glycolide) (PLGA), poly(L-lactide-co-D, L-lactide), poly(D, L-lactide co-trimethylene carbonate), polyhydroxybutyrate (PHB), poly($\epsilon$-caprolactone), poly($\gamma$-valerolactone), poly($\gamma$-butyrolactone), poly(caprolactone), or copolymers thereof. Such polymers are known to bioerode and are suitable for use in the ceramic materials described herein for bone grafts and the like. In addition, bioresorbable inorganic supplementary materials, such as compositions including $SiO_2$, $Na_2O$, $CaO$, $P_2O_5$, $Al_2O_3$ and/or $CaF_2$, can be used, as well as salts, e.g., NaCl, and sugars, e.g., mannitol, and combinations thereof.

Supplementary materials can also be selected from non-resorbable or poorly resorbable materials. Suitable non-resorbable or poorly resorbable materials include, without limitation, dextrans, cellulose and derivatives thereof (e.g., methylcellulose, carboxy methylcellulose, hydroxypropyl methylcellulose, and hydroxyethyl cellulose), polyethylene, polymethylmethacrylate (PMMA), carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly (ethylene terephthalate)polyamide, and lubricants, such as polymer waxes, lipids and fatty acids.

The ceramic material described herein is also useful the useful for the preparation of delivery vehicles for biologically active agents. In general, the only requirement is that the substance remain active within material during fabrication or be capable of being subsequently activated or re-activated, or that the biologically active agent be added to the material after at the time of implantation of into a host or following fabrication of the vehicle.

Biologically active agents that can be incorporated into the ceramic material described herein include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the ceramic material described herein include, without limitation, anticancer agents, antibiotics, analgesics, anti-inflammatory agents, immunosuppressants, enzyme inhibitors, antihistamines, anti-convulsants, hormones, muscle relaxants, antispasmodics, ophthalmic agents, prostaglandins, anti-depressants, anti-psychotic substances, trophic factors, osteoinductive proteins, growth factors, and vaccines.

Generally, any therapeutic agent can be encapsulated in the drug delivery vehicle or composition comprising the ceramic material described herein. As used herein, the term "therapeutic agent" means a molecule, group of molecules, complex or substance administered to an organism for diagnostic, therapeutic, preventative medical, or veterinary purposes. As used herein, the term "therapeutic agent" includes a "drug" or a "vaccine." This term include externally and internally administered topical, localized and systemic human and animal pharmaceuticals, treatments, remedies, nutraceuticals, cosmeceuticals, biologicals, devices, diagnostics and contraceptives, including preparations useful in clinical and veterinary screening, prevention, prophylaxis, healing, wellness, detection, imaging, diagnosis, therapy, surgery, monitoring, cosmetics, prosthetics, forensics and the like. This term can also be used in reference to agriceutical, workplace, military, industrial and environmental therapeutics or remedies comprising selected molecules or selected nucleic acid sequences capable of recognizing cellular receptors, membrane receptors, hormone receptors, therapeutic receptors, microbes, viruses or selected targets comprising or capable of contacting plants, animals and/or humans. This term can also specifically include nucleic acids and compounds comprising nucleic acids that produce a therapeutic effect, for example deoxyribonucleic acid (DNA), ribonucleic acid (RNA), or mixtures or combinations thereof, including, for example, DNA nanoplexes, siRNA, shRNA, aptamers, ribozymes, decoy nucleic acids, antisense nucleic acids, RNA activators, and the like.

The term "therapeutic agent" also includes an agent that is capable of providing a local or systemic biological, physiological, or therapeutic effect in the biological system to which it is applied. For example, the therapeutic agent can act to control infection or inflammation, enhance cell growth and tissue regeneration, control tumor growth, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism. Additionally, a silk-based drug delivery composition can contain combinations of two or more therapeutic agents.

A therapeutic agent can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the therapeutic agent is a small molecule.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kDa), preferably less than 3 kDa, still more preferably less than 2 kDa, and most preferably less than 1 kDa. In some cases it is preferred that a small molecule have a molecular weight equal to or less than 700 Daltons.

Exemplary therapeutic agents include, but are not limited to, those found in *Harrison's Principles of Internal Medicine*, $13^{th}$ Edition, Eds. T. R. Harrison et al. McGraw-Hill N.Y., NY; Physicians' Desk Reference, $50^{th}$ Edition, 1997, Oradell N.J., Medical Economics Co.; Pharmacological Basis of Therapeutics, $8^{th}$ Edition, Goodman and Gilman, 1990; United States Pharmacopeia, The National Formulary, USP XII NF XVII, 1990, the complete contents of all of which are incorporated herein by reference.

Therapeutic agents include the herein disclosed categories and specific examples. It is not intended that the category be limited by the specific examples. Those of ordinary skill in the art will recognize also numerous other compounds that fall within the categories and that are useful according to the present disclosure. Examples include a radiosensitizer, a steroid, a xanthine, a beta-2-agonist bronchodilator, an anti-inflammatory agent, an analgesic agent, a calcium antagonist, an angiotensin-converting enzyme inhibitors, a beta-blocker, a centrally active alpha-agonist, an alpha-1-antagonist, an anticholinergic/antispasmodic agent, a vasopressin analogue, an antiarrhythmic agent, an antiparkinsonian agent, an antiangina/antihypertensive agent, an anticoagulant agent, an antiplatelet agent, a sedative, an ansiolytic agent, a peptidic agent, a biopolymeric agent, an antineoplastic agent, a laxative, an antidiarrheal agent, an antimicrobial agent, an antifingal agent, a vaccine, a protein, or a nucleic acid. In a further aspect, the pharmaceutically active agent can be coumarin, albumin, steroids such as betamethasone, dexamethasone, methylprednisolone, prednisolone, prednisone, triamcinolone, budesonide, hydrocortisone, and pharmaceutically acceptable hydrocortisone derivatives; xanthines such as theophylline and doxophylline; beta-2-agonist bronchodilators such as salbutamol, fenterol, clenbuterol, bambuterol, salmeterol, fenoterol; antiinflammatory agents, including antiasthmatic anti-inflammatory agents, antiarthritic antiinflammatory agents, and non-steroidal antiinflammatory agents, examples of which include but are not limited to sulfides, mesalamine, budesonide, salazopyrin, diclofenac, pharmaceutically acceptable diclofenac salts, nimesulide, naproxene, acetaminophen, ibuprofen, ketoprofen and piroxicam; analgesic agents such as salicylates; calcium channel blockers such as nifedipine, amlodipine, and nicardipine; angiotensin-converting enzyme inhibitors such as captopril, benazepril hydrochloride, fosinopril sodium, trandolapril, ramipril, lisinopril, enalapril, quinapril hydrochloride, and moexipril hydrochloride; beta-blockers (i.e., beta adrenergic blocking agents) such as sotalol hydrochloride, timolol maleate, esmolol hydrochloride, carteolol, propanolol hydrochloride, betaxolol hydrochloride, penbutolol sulfate, metoprolol tartrate, metoprolol succinate, acebutolol hydrochloride, atenolol, pindolol, and bisoprolol fumarate; centrally active alpha-2-agonists such as clonidine; alpha-1-antagonists such as doxazosin and prazosin; anticholinergic/antispasmodic agents such as dicyclomine hydrochloride, scopolamine hydrobromide, glycopyrrolate, clidinium bromide, flavoxate, and oxybutynin; vasopressin analogues such as vasopressin and desmopressin; antiarrhythmic agents such as quinidine, lidocaine, tocainide hydrochloride, mexiletine hydrochloride, digoxin, verapamil hydrochloride, propafenone hydrochloride, flecainide acetate, procainamide hydrochloride, moricizine hydrochloride, and disopyramide phosphate; antiparkinsonian agents, such as dopamine, L-Dopa/Carbidopa, selegiline, dihydroergocryptine, pergolide, lisuride, apomorphine, and bromocryptine; anti-angina agents and antihypertensive agents such as isosorbide mononitrate, isosorbide dinitrate, propranolol, atenolol and verapamil; anticoagulant and antiplatelet agents such as Coumadin, warfarin, acetylsalicylic acid, and ticlopidine; sedatives such as benzodiazapines and barbiturates; ansiolytic agents such as lorazepam, bromazepam, and diazepam; peptidic and biopolymeric agents such as calcitonin, leuprolide and other LHRH agonists, hirudin, cyclosporin, insulin, somatostatin, protirelin, interferon, desmopressin, somatotropin, thymopentin, pidotimod, erythropoietin, interleukins, melatonin, granulocyte/macrophage-CSF, and heparin; antineoplastic agents such as etoposide, etoposide phosphate, cyclophosphamide, methotrexate, 5-fluorouracil, vincristine, doxorubicin, cisplatin, hydroxyurea, leucovorin calcium, tamoxifen, flutamide, asparaginase, altretamine, mitotane, and procarbazine hydrochloride; laxatives such as senna concentrate, casanthranol, bisacodyl, and sodium picosulphate; antidiarrheal agents such as difenoxine hydrochloride, loperamide hydrochloride, furazolidone, diphenoxylate hdyrochloride, and microorganisms; vaccines such as bacterial and viral vaccines; antimicrobial agents such as penicillins, cephalosporins, and macrolides, antifungal agents such as imidazolic and triazolic derivatives; and nucleic acids such as DNA sequences encoding for biological proteins, and antisense oligonucleotides.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelinA receptor antagonists, retinoic acid receptor agonists, immuno-modulators, hormonal and antihormonal agents, photodynamic agents, and tyrosine kinase inhibitors.

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillinV, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramiisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^o$-monomethyl-Larginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-amino glutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenybutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlomaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Trophic factors are factors whose continued presence improves the viability or longevity of a cell. Trophic factors include, Without limitation, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, bone growth/cartilage-inducing factor (alpha and beta), bone morphogenetic proteins, interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, and transforming growth factors (beta), including beta-1, beta-2, beta-3, inhibin, and activin.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g, testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The biologically active agent can be an osteogenic protein. Accordingly, in some embodiments, the biologically active agent is desirably selected from the family of proteins known as the transforming growth factors beta (TGF-β) superfamily of proteins, which includes the activins, inhibins and bone morphogenetic proteins (BMPs). Most preferably, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins, which can be used include Vgr-2, Jones et al., Mol. Endocrinol. 611961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention can be BIP, disclosed in WO94/01557; HP00269, disclosed in JP Publication number: 7-250688; and BMP-14 (also known as MP52, CDMP1, and GDF5), disclosed in PCT application WO93/16099. The disclosures of all of the above applications are incorporated herein by reference. Subsets of BMPs which can be used include BMP-2, BMP-3, BMP-3b, BMP-4, BMP-5, BMP-6, BMP-7, BMP-8, BMP-9, BMP-10, BMP-11, BMP-12, BMP-13, BMP-14, BMP-15, BMP-16, BMP-17, and BMP18. Other osteogenic agents known in the art can also be used, such as teriparatide (FORTEO™), CHRYSALIN®, prostaglandin E2, or LIM protein, among others.

The biologically active agent can be recombinantly produced, or purified from a protein composition. The active agent, if a TGF-β such as a BMP, or other dimeric protein, can be homodimeric, or can be heterodimeric with other BMPs (e. g., a heterodimer composed of one monomer each of BMP-2 and BMP-6) or With other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the content of which is incorporated herein by reference.

The active agent can further include additional agents such as the Hedgehog, Frazzled, Chordin, Noggin, Cerberus and Follistatin proteins. These families of proteins are generally described in Sasai et al., Cell 791779-790 (1994) (Chordin); PCT Patent Publication WO94/05800 (Noggin); and Fukui et al., Devel. Biol. 159: 1 31 (1993) (Follistatin). Hedgehog proteins are described in WO96/16668; WO96/17924; and WO95/18856. The Frazzled family of proteins is a recently discovered family of proteins With high homology to the extracellular binding domain of the receptor protein family known as Frizzled. The Frizzled family of genes and proteins is described in Wang et al., .1. Biol. Chem. 271:44684476 (1996). The active agent can also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are hereby incorporated by reference herein.

The amount of osteogenic protein effective to stimulate increased osteogenic activity of present or infiltrating progenitor or other cells will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Biologically active agents can be introduced into the ceramic material during or after its formation. Agents can conveniently be mixed into the starting solution prior to fabrication of the ceramic material. Alternatively, the ceramic material can be fabricated, optionally shaped into a desired shape, and then exposed to the biologically active agent in solution. This particular approach is particularly well suited for proteins, which are known to have an affinity for apatitic materials. A buffer solution containing the biologically active agent can be employed, instead of water, as the aqueous solution in which the ceramic material is, for example, irrigated prior to implantation. Buffers can be used in any pH range, but most often will be used in the range of 5.0 to 8.0 in preferred embodiments the pH will be compatible with prolonged stability and efficacy of the desired biologically active agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for its biocompatibility with the host tissues and its compatibility with the biologically active agent. For most applications of nucleic acids, peptides or antibiotics a simple phosphate buffered saline can suffice.

Standard protocols and regimens for delivery of the above listed agents are known in the art. Typically, these protocols are based on oral or intravenous delivery. Biologically active agents are introduced into the vehicle in amounts that allow delivery of an appropriate dosage of the agent to the implant site. In most cases, dosages are determined using guidelines known to practitioners and applicable to the particular agent in question. The exemplary amount of biologically active agent to be included in the ceramic material or a vehicle comprising the ceramic material is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent Generally, any amount of the supplementary material, such as a biocompatible polymer, biologically active agent, and therapeutic agent can be loaded into the ceramic material. For example, from about 0.1 ng to about 1000 mg of the therapeutic agent can be loaded in the ceramic material. In some embodiment, amount of the supplementary in the ceramic material is selected from the range about from 0.001% (w/w) up to 95% (w/w), preferably, from about 5% (w/w) to about 75% (w/w), and most preferably from about 10% (w/w) to about 60% (w/w) of the total composition. In some embodiments, amount of amount of the supplementary in the ceramic material is from about 0.01% to about 95% (w/v), from about 0.1% to about 90% (w/w), from about 1% to about 85% (w/w), from about 5% to about 75% (w/w), from about 10% to about 65% (w/w), or from about 10% to about 50% (w/w), of the total composition.

In some embodiments, amount of the supplementary in the ceramic material is from about 1% to about 99% (w/w), from about 0.05% to about 99% (w/w), from about 0.1% to about 90% (w/w), from about 0.5% to about 85% (w/w), from about 5% to about 80% (w/w), from about 10% to about 60% (w/w) of the total composition. In some embodiments, amount of the supplementary in the ceramic material is from about 0.1% to about 99% (w/w), from about 1% to about 90% (w/w), from about 2% to about 80% (w/w), from about 5% to about 75% (w/w), from about 5% to about 50% (w/w), from about 0.055% to about 0.1% (w/w) of the total composition.

After preparation, the ceramic material described herein can be sterilized using conventional sterilization process such as radiation-based sterilization (i.e. gamma-ray), chemical based sterilization (ethylene oxide), autoclaving, or other appropriate procedures. In some embodiments, sterilization process can be with ethylene oxide at a temperature between from about 52° C. to about 55° C. for a time of 8 or less hours. The ceramic material described herein can also be processed aseptically. Sterile drug delivery compositions can be packaged in an appropriate sterilize moisture resistant package for shipment.

Without wishing to be bound by a theory, the ceramic material described herein provides a number of advantages. The material can withstand physiological loading forces; can initiate new bone formation and stimulate healing through direct bone-silk interface; can promote osteogenesis by local delivery of bone morphogenic growth factors; and can achieve complete graft resorption and non-union closure.

Silk

As used herein, the term "silk fibroin" or "fibroin" includes silkworm silk and insect or spider silk protein. See e.g., Lucas et al., Adv. Protein Chem. 1958, 13, 107-242. Any type of silk fibroin can be used according to aspects of the present invention. There are many different types of silk produced by a wide variety of species, including, without limitation: *Antheraea mylitta; Antheraea pernyi; Antheraea yamamai; Galleria mellonella; Bombyx mori; Bombyx mandarina; Galleria mellonella; Nephila clavipes; Nephila senegalensis; Gasteracantha mammosa; Argiope aurantia; Araneus diadematus; Latrodectus geometricus; Araneus bicentenarius; Tetragnatha versicolor; Araneus ventricosus; Dolomedes tenebrosus; Euagrus chisoseus; Plectreurys tristis; Argiope trifasciata*; and *Nephila madagascariensis*. Other silks include transgenic silks, genetically engineered silks (recombinant silk), such as silks from bacteria, yeast, mammalian cells, transgenic animals, or transgenic plants, and variants thereof. See for example, WO 97/08315 and U.S. Pat. No. 5,245,012, content of both of which is incorporated herein by reference in its entirety. In some embodiments, silk fibroin can be derived from other sources such as spiders, other silkworms, bees, synthesized silk-like peptides, and bioengineered variants thereof. In some embodiments, silk fibroin can be extracted from a gland of silkworm or transgenic silkworms. See for example, WO2007/098951, content of which is incorporated herein by reference in its entirety.

In some embodiments, the composition comprises low molecular weight silk fibroin fragments, i.e., the composition comprises a population of silk fibroin fragments having a range of molecular weights, characterized in that: no more than 15% of total weight of the silk fibroin fragments in the population has a molecular weight exceeding 200 kDa, and at least 50% of the total weight of the silk fibroin fragments in the population has a molecular weight within a specified range, wherein the specified range is between about 3.5 kDa and about 120 kDa. Without limitations, the molecular weight can be the peak average molecular weight (Mp), the number average molecular weight (Mn), or the weight average molecular weight (Mw)

As used herein, the phrase "silk fibroin fragments" refers to polypeptides having an amino acid sequence corresponding to fragments derived from silk fibroin protein, or variants thereof. In the context of the present disclosure, silk fibroin fragments generally refer to silk fibroin polypeptides that are smaller than the naturally occurring full length silk fibroin counterpart, such that one or more of the silk fibroin fragments within a population or composition are less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, etc. In some embodiments, "a composition comprising silk fibroin fragments" encompasses a composition comprising non-fragmented (i.e., full-length) silk fibroin polypeptide, in additional to shorter fragments of silk fibroin polypeptides. Silk fibroin fragments described herein can be produced as recombinant proteins, or derived or isolated (e.g., purified) from a native silk fibroin protein or silk cocoons. In some embodiments, the silk fibroin fragments can be derived by degumming silk cocoons under a specified condition selected to produce the silk fibroin fragments having the desired range of molecular weights. Low molecular weight silk fibroin compositions are described in U.S. Provisional Application Ser. No. 61/883,732, filed on Sep. 27, 2013, content of which is incorporated herein by reference in its entirety.

In some embodiments, the silk fibroin is substantially depleted of its native sericin content (e.g., 5% (w/w) or less residual sericin in the final extracted silk). Alternatively, higher concentrations of residual sericin can be left on the silk following extraction or the extraction step canbe omitted. In some embodiments, the sericin-depleted silk fibroin has, e.g., about 1% (w/w) residual sericin, about 2% (w/w) residual sericin, about 3% (w/w) residual sericin, about 4% (w/w), or about 5% (w/w) residual sericin. In some embodiments, the sericin-depleted silk fibroin has, e.g., at most 1% (w/w) residual sericin, at most 2% (w/w) residual sericin, at most 3% (w/w) residual sericin, at most 4% (w/w), or at most 5% (w/w) residual sericin. In some other embodiments, the sericin-depleted silk fibroin has, e.g., about 1% (w/w) to about 2% (w/w) residual sericin, about 1% (w/w) to about 3% (w/w) residual sericin, about 1% (w/w) to about 4% (w/w), or about 1% (w/w) to about 5% (w/w) residual sericin. In some embodiments, the silk fibroin is entirely free of its native sericin content. As used herein, the term "entirely free" (i.e. "consisting of" terminology) means that within the detection range of the instrument or process being used, the substance cannot be detected or its presence cannot be confirmed. In some embodiments, the silk fibroin is essentially free of its native sericin content. As used herein, the term "essentially free" (or "consisting essentially of") means that only trace amounts of the substance can be detected.

Degummed silk can be prepared by any conventional method known to one skilled in the art. For example, *B. mori* cocoons are boiled for about up to 90 minutes, generally about 10 to 60 minutes, in an aqueous solution. In one embodiment, the aqueous solution is about 0.02M $Na_2CO_3$. The cocoons are rinsed, for example, with water to extract the sericin proteins. The degummed silk can be dried and used for preparing silk powder. Alternatively, the extracted silk can dissolved in an aqueous salt solution. Salts useful for this purpose include lithium bromide, lithium thiocyanate, calcium nitrate or other chemicals capable of solubilizing silk. In some embodiments, the extracted silk can be dissolved in about 8M-12 M LiBr solution. The salt is consequently removed using, for example, dialysis. The degummed silk is also referred to as regenerated silk herein.

If necessary, the solution can then be concentrated using, for example, dialysis against a hygroscopic polymer, for example, PEG, a polyethylene oxide, amylose or sericin. In some embodiments, the PEG is of a molecular weight of 8,000-10,000 g/mol and has a concentration of about 10% to about 50% (w/v). A slide-a-lyzer dialysis cassette (Pierce, MW CO 3500) can be used. However, any dialysis system can be used. The dialysis can be performed for a time period sufficient to result in a final concentration of aqueous silk solution between about 10% to about 30%. In most cases dialysis for 2-12 hours can be sufficient. See, for example, International Patent Application Publication No. WO 2005/012606, the content of which is incorporated herein by reference in its entirety. Another method to generate a concentrated silk solution comprises drying a dilute silk solution (e.g., through evaporation or lyophilization). The dilute solution can be dried partially to reduce the volume thereby increasing the silk concentration. The dilute solution can be dried completely and then dissolving the dried silk fibroin in a smaller volume of solvent compared to that of the dilute silk solution.

In some embodiments, the silk fibroin solution can be produced using organic solvents. Such methods have been described, for example, in Li, M., et al., *J. Appl. Poly Sci.* 2001, 79, 2192-2199; Min, S., et al. *Sen'I Gakkaishi* 1997, 54, 85-92; Nazarov, R. et al., *Biomacromolecules* 2004 5,718-26, content of all which is incorporated herein by reference in their entirety. An exemplary organic solvent that can be used to produce a silk solution includes, but is not limited to, hexafluoroisopropanol (HFIP). See, for example, International Application No. WO2004/000915, content of which is incorporated herein by reference in its entirety. In some embodiments, the silk solution is entirely free or essentially free of organic solvents, i.e., solvents other than water.

In some embodiments, the solution comprising the silk and CaP comprises an organic solvent, e.g., HFIP. In some other embodiments, the solution comprising the silk and CaP is free or essentially free of organic solvents.

Generally, any amount of silk can be present in the composition or the porous material prepared therefrom. For example, amount of silk in the composition or the porous material prepared therefrom can be from about 1 wt % to about 50 wt % of silk, e.g., silk fibroin. In some embodiments, the amount of silk in the composition or the porous material prepared therefrom can be from about 1 wt % to about 35 wt %, from about 1 wt % to about 30 wt %, from about 1 wt % to about 25 wt %, from about 1 wt % to about 20 wt %, from about 1 wt % to about 15 wt %, from about 1 wt % to about 10 wt %, from about 5 wt % to about 25 wt %, from about 5 wt % to about 20 wt %, from about 5 wt % to about 15 wt %. In some embodiments, the amount of silk in the solution or the porous material prepared therefrom can be about 4 wt %, about 8 wt %, about 14 wt % or about 24 wt %.

Exact amount of silk in the silk solution before addition of the calcium phosphate material can be determined by drying a known amount of the silk solution and measuring the mass of the residue to calculate the solution concentration.

In some embodiments, silk for forming the silk/CaP composition can be in the form of a particle. Various methods of producing silk microparticles or nanoparticles are known in the art. In some embodiments, the silk microparticles or nanoparticles can be produced by a polyvinyl alcohol (PVA) phase separation method as described in, e.g., International App. No. WO 2011/041395, the content of which is incorporated herein by reference in its entirety. Other methods for producing silk microparticles or nanoparticles are described in, for example, U.S. App. No. U.S. 2010/0028451 and International App. No.: WO 2008/118133 (using lipid as a template for making silk microspheres or nanospheres); and in Wenk et al. J Control Release 2008; 132: 26-34 (using spraying method to produce silk microspheres or nanospheres), contents of all which are incorporated herein by reference in their entireties. Certain embodiments of micro- to nano-scale silk fibroin particles and related technology are also provided in U.S. Provisional Application Ser. No. 61/883,933, filed Sep. 27, 2013, titled "SYNTHESIS OF SILK FIBROIN MICRO- AND SUBMICRON SPHERES USING A CO-FLOW METHOD," content of which is incorporated herein by reference in its entirety.

Generally, silk particles or powder can be obtained by inducing gelation in a silk solution and reducing the resulting silk gel into particles, e.g., by grinding, cutting, crushing, sieving, sifting, and/or filtering. Silk gels can be produced by sonicating a silk solution, by applying a shear stress to the silk solution; modulating the salt content of the silk solution; by modulating the pH of the silk solution; or by application of electrical current (electrogelation). The pH of the silk solution can be altered by subjecting the silk solution to an electric field and/or reducing the pH of the silk solution with an acid. Methods for producing silk gels using sonication are described for example in U.S. Pat. App. Pub No. U.S. 2010/0178304 and Int. Pat. App. Pub. No. WO 2008/150861, contents of both which are incorporated herein by reference in their entirety. Methods for producing silk gels using shear stress are described, for example, in International Patent App. Pub. No.: WO 2011/005381, the content of which is incorporated herein by reference in its entirety. Methods for producing silk gels by modulating the pH of the silk solution are described, for example, in U.S. Pat. App. Pub. No.: US 2011/0171239, the content of which is incorporated herein by reference in its entirety.

In some embodiments, silk particles can be produced using a method as described in the Examples section. As shown schematically in FIG. 24, a silk foam can be produced by freeze-drying a silk solution. The foam then can be reduced to particles. For example, a silk solution can be cooled to a temperature at which the liquid carrier transforms into a plurality of solid crystals or particles and removing at least some of the plurality of solid crystals or particles to leave a porous silk material (e.g., silk foam). The silk solution can be cooled to a temperature below 0° C. For example, the silk solution can be cooled to a temperature of about −5° C., about −10° C., about −15° C., about −20° C., about −25° C. or below for a period time (e.g., 1 hour, 2 hours, 4 hours, 6 hours, 12 hours, 18 hours, 24 hours, 30 hours, 36 hours, 42 hours, 48 hours, 54 hours, 60 hours, 66 hours, 72 hours or more). In some embodiments, the silk solution can be further cooled to a lower temperature after cooling at a first temperature. For example, the silk solution can be cooled to a temperature about −40° C., about −45° C., about −50° C., about −55° C., about −60° C., about −65° C., about −70° C., about −75° C., or about −80° C. or below for a period of time (e.g., about 30 minutes to about 72 hours, about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or more) after the silk solution has been cooled at temperature of about 0° C. to about 30° C. for a period of time. In some embodiments, the silk solution can be cooled to a temperature of about −20° C. for a period of about 24 hours followed by cooling to about −80° C. for a period of about 2-3 hours.

After cooling, liquid carrier can be removed, at least partially, by sublimation, evaporation, and/or lyophilization. In some embodiments, the liquid carrier can be removed under reduced pressure. In some embodiments, the liquid carrier can be removed by lyophilization at a pressure of about 0.006 Torr.

Optionally, the conformation of the silk in the silk foam or particles formed therefrom can be altered. In some embodiments, the conformation of the silk is altered before reducing the foam to the particles. In some embodiments, the conformation of the silk is altered after reducing the foam to the particles. Without wishing to be bound by a theory, the induced conformational change can alter the crystallinity of the silk fibroin in the silk particles. Silk II beta-sheet crystallinity. This can alter dissolvability of the particles in water. The conformational change can be induced by any methods known in the art, including, but not limited to, alcohol immersion (e.g., ethanol, methanol), water annealing, heating annealing, shear stress (e.g., by vortexing), ultrasound (e.g., by sonication), pH reduction (e.g., pH titration), and/or exposing the silk particles to an electric field and any combinations thereof. In some embodiments, the conformation change in silk is induced by 100% MeOH, e.g., 0% water content.

In some embodiments, no conformational change in the silk fibroin is induced, i.e., crystallinity of the silk fibroin in the silk foam is not altered or changed before subjecting the foam to particle formation. If no conformational change in the silk fibroin is induced in the foam before subjecting the foam to particle formation, conformational change in silk can be induced in the formed silk particles.

After formation, the silk foam can be subjected to grinding, cutting, crushing, or any combinations thereof to form silk particles. For example, the silk foam can be blended in a conventional blender or milled in a ball mill to form silk particles of desired size. In some embodiments, the silk particles of a desired size can be selected, e.g., by filtering through molecular sieves. This can allow a population of particles of homogenous size.

Without limitations, the silk particles can be of any desired size. In some embodiments, the particles can have a size ranging from about 0.01 µm to about 1000 µm, about 0.05 µm to about 500 µm, about 0.1 µm to about 250 µm, about 0.25 µm to about 200 µm, or about 0.5 µm to about 100 µm. Further, the silk particle can be of any shape or form, e.g., spherical, rod, elliptical, cylindrical, capsule, or disc.

Figure 28:
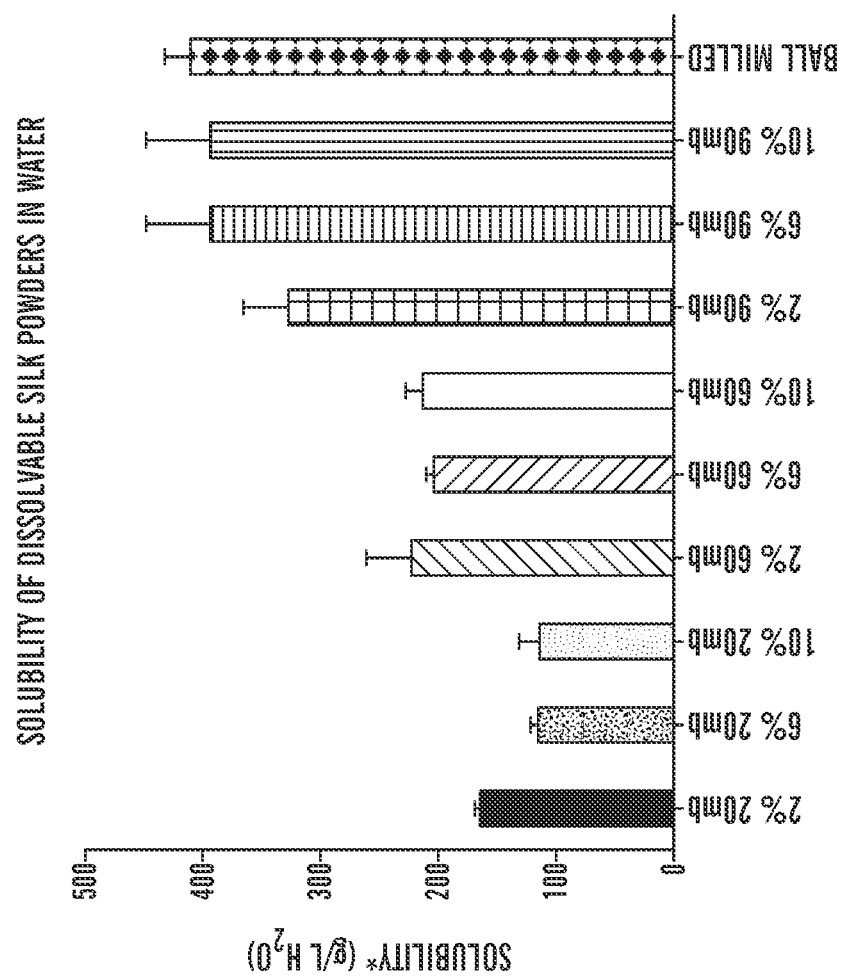
FIG. 28 shows solubility data for silk powders formed by conventional blending of unstabilized, lyophilized silk foams. As can be seen, higher weight per volume silk concentration foams generally produce powder with higher solubility, and longer boil time silk produces powder with higher solubility. Solubility measurements were determined at ambient conditions for 1 g powder in water (appx. 20° C.), N=4. Control is 350 rpm/3 hour ball-milled silk fibers.

In some embodiments, the silk particle is a microparticle or a nanoparticle. In some embodiments, the silk particle has a particle size of about 0.01 µm to about 1000 µm, about 0.05 µm to about 750 µm, about 0.1 µm to about 500 µm, about 0.25 µm to about 250 µm, or about 0.5 µm to about 100 µm. In some embodiments, the silk particle has a particle size of about 0.1 nm to about 1000 nm, about 0.5 nm to about 500 nm, about 1 nm to about 250 nm, about 10 nm to about 150 nm, or about 15 nm to about 100 nm. In some embodiments, the silk particle has a particle size of about 200 nm to about 325 nm, about As shown in Table 1, the particle size can be adjusted using silk fibroin of different lengths. Previous work from some of the inventors had shown that increasing the degumming time of cocoons for producing silk fibroin led to silk fibroin of lower molecular weights. As seen in Table 1, using silk solution of same concentrations led to silk particles of smaller size when silk was with low molecular weight silk (e.g., longer cocoons boiling time) relative to when the silk was of higher molecular weight (e.g., shorter boiling time). This is seen when 20 minute boiling time is compared to 60 minute or 90 minute boiling time and 60 minute boiling time is compared to 90 minute boiling time at each of the different silk solution concentrations. Further, silk powder created from silk with higher boil times generally demonstrates better solubility (FIG. 28).

Accordingly, in some embodiments, the silk particles are soluble in water. This can allow homogenous mixing with calcium phosphate once water (or other solvent) is added added. Without wishing to be bound by a theory, ball-milling or grinding tends to create a lot of friction that degrades the silk and lowers its overall solubility as a powder. However, blending the silk under milder conditions, e.g., with a conventional (kitchen top) blender can reduce or inhibit degradation of the silk. Thus increasing solubility of the silk particles. This doesn't mean that ball-milling can't be used. Silk powders made via ball milling and grinding that have some solubility are also known.

TABLE 1

| Silk Boil Time (minutes) | Silk Concentration (% w/v) | Median Particle Size (μm) | Standard Deviation (μm) |
|---|---|---|---|
| 20 | 2 | 265.205 | 129.404 |
| 20 | 6 | 247.667 | 134.812 |
| 20 | 10 | 308.568 | 130.750 |
| 60 | 2 | 236.722 | 124.857 |
| 60 | 6 | 230.558 | 129.178 |
| 60 | 10 | 236.397 | 131.511 |
| 90 | 2 | 225.274 | 122.279 |
| 90 | 6 | 233.361 | 130.742 |
| 90 | 10 | 285.074 | 126.981 |

Calcium Phosphate Material

As used herein, the term "calcium phosphate material" refers to any material composed of calcium and phosphate ions. The term "calcium phosphate material" is intended to include naturally occurring and synthetic materials composed of calcium and phosphate ions. The ratio of calcium to phosphate ions in the calcium phosphate materials is preferably selected such that the resulting material is able to perform its intended function. For convenience, the calcium to phosphate ion ratio is abbreviated as the "Ca/P ratio." In some embodiments, the Ca/P ratio can range from about 1:1 to about 1.67 to 1. In some embodiments, the calcium phosphate material can be calcium deficient. By "calcium deficient" is meant a calcium phosphate material with a calcium to phosphate ratio of less than about 1.6 as compared to the ideal stoichiometric value of approximately 1.67 for hydroxyapatite The calcium phosphate material can be selected, for example, from one or more of brushite, octacalcium phosphate, tricalcium phosphate (also referred to as tricalcic phosphate and calcium orthophosphate), calcium hydrogen phosphate, calcium dihydrogen phosphate, apatite, and/or hydroxyapatite. Further, tricalcium phosphate (TCP) can be in the alpha or the beta crystal form. In some embodiments, the calcium phosphate material is beta-tricalcium phosphate or hydroxyapatite (HA).

In some embodiments, calcium phosphate material can be selected, for example, from the group consisting of amorphous calcium phosphate, poorly crystalline calcium phosphate, hydroxyapatite, carbonated apatite (calcium-deficient hydroxyapatite), monocalcium phosphate, calcium metaphosphate, heptacalcium phosphate, dicalcium phosphate dihydrate, tetracalcium phosphate, octacalcium phosphate, calcium pyrophosphate, and tricalcium phosphate, or mixtures thereof In some embodiments, the calcium phosphate material is a reactive calcium phosphate material. By "reactive calcium phosphate material" material is meant a calcium phosphate material that can self-set or harden. In some embodiments, the reactive phosphate calcium phosphate material can harden at 37° C. In some embodiments, the reactive phosphate calcium phosphate material can harden at body temperature. In some embodiments, the reactive phosphate calcium phosphate material can harden less than 12 hours (e.g., 6 hours, 5 hours, 4 hours, 3 hours, 2 hours, 1 hour, 45 minutes, 30 minutes, 15 minutes or less) after application or use. Exemplary reactive calcium phosphate materials that can self-set or harden are described in U.S. Pat. No. 8,454, 988; U.S. Pat. No. 8,507,008; and U.S. Pat. No. 8,545,858 contents of all of which are incorporated herein by reference in their entireties.

The amount of the calcium phosphate material in the solution can also range from about 1% to about 99% (w/v). In some embodiments, the amount the calcium phosphate material in the solution can be from about 5% to about 95% (w/v), from about 10% to about 90% (w/v), from about 15% to about 80% (w/v), from about 20% to about 75% (w/v), from about 25% to about 60% (w/v), or from about 30% to about 50% (w/v).

The calcium phosphate material can be in the form of particles. Without limitations, the calcium phosphate material particles can be of any desired size. In some embodiments, the calcium phosphate material particles can have a size ranging from about 0.01 μm to about 1000 nm, about 0.05 μm to about 500 μm, about 0.1 μm to about 250 μm, about 0.25 μm to about 200 μm, or about 0.5 μm to about 100 μm. Further, the calcium phosphate material particle can be of any shape or form, e.g., spherical, rod, elliptical, cylindrical, capsule, or disc.

In some embodiments, the calcium phosphate material particle is a microparticle or a nanoparticle. In some embodiments, the calcium phosphate material particle has a particle size of about 0.01 μm to about 1000 μm, about 0.05 μm to about 750 μm, about 0.1 μm to about 500 μm, about 0.25 μm to about 250 μm, or about 0.5 μm to about 100 μm. In some embodiments, the silk particle has a particle size of about 0.1 nm to about 1000 nm, about 0.5 nm to about 500 nm, about 1 nm to about 250 nm, about 10 nm to about 150 nm, or about 15 nm to about 100 nm. In some embodiments, the calcium phosphate material particle has a particle size of about 2.5 μm to about 12.5 μm. In some embodiments, the calcium phosphate material particle has a particle size of about 3.5 μm. In some embodiments, the calcium phosphate material particle has a particle size of about 10.5 μm.

In some embodiments, the silk and the calcium phosphate material are both microparticle. In some embodiments, when the silk and the calcium phosphate material are both microparticles, the particle size of the silk particle is larger than the particle size of the calcium phosphate material. For example, the silk particle size can be at least 1.1×, 1.25×, 1.25×, 1.5×, 1.75×, 2×, 2.25×, 2.5×, 2.75×, 3×, 4×, 5×, 6×, 7×, 8×, 10×, 15×, 20× or larger than the calcium phosphate particle size. In some embodiments, the silk particles and the calcium phosphate particles are of substantially similar sizes, e.g., within 7.5%, 7%, 6.5%, 6%, 5.5%, 5%, 4.5%, 4%, 3.5%, 3%, 2.5%, 2%, 1.5%, 1%, 0.5% or less of each other.

Exemplary embodiments of the invention can be described by one or more of the following numbered paragraphs:

1. A method of preparing a calcium phosphate ceramic material, the method comprising: (i) providing a green body prepared from a composition comprising silk and calcium phosphate material; and (ii) sintering the green body to form the ceramic material.
2. The method of paragraph 1, wherein said composition is in the form of a solution, paste, slurry, suspension, colloid, mixture, or dispersion.
3. The method of paragraph 1 or 2, wherein the calcium phosphate material is selected from the group consisting of brushite, octacalcium phosphate, tricalcium phosphate (also referred to as tricalcic phosphate and calcium orthophosphate), calcium hydrogen phosphate, calcium dihydrogen phosphate, apatite, hydroxyapatite, and any combinations thereof 4. The method of any of paragraphs 1-3, wherein said providing the green body comprises forming the green body from the composition comprising the silk and calcium phosphate material.
5. The method of any of paragraphs 1-4, wherein said forming the green body further comprises preparing the composition comprising the silk and calcium phosphate material.
6. The method of any of paragraphs 1-5, further comprising preparing a solution comprising the composition.
7. The method of any of paragraphs 1-6, wherein the solution has a low viscosity.
8. The method of any of paragraphs 1-7 wherein the composition has a high viscosity.
9. The method of any of paragraphs 1-8, wherein said preparing the solution comprises: (i) adding a calcium phosphate material powder/particles to an aqueous silk solution comprising silk fibroin; (ii) adding an aqueous silk solution comprising silk fibroin; (iii) adding water to mixture of a calcium phosphate material powder/particles and a silk powder/particles; (iv) adding a mixture of mixture of a calcium phosphate material powder/particles and a silk powder/particles to water; (v) adding a silk powder/particles to a solution of the calcium phosphate material; or (vi) adding a solution of the calcium phosphate material to silk powder/particles.
10. The method of any of paragraphs 1-9, further comprising preparing the silk powder/particles.
11. The method of any of paragraphs 1-10, wherein said preparing the silk powder/particles comprises: (i) freeze-drying a solution comprising the silk fibroin to produce a silk material; and (ii) reducing the silk material from (i) into a powder or particulates.
12. The method of any of paragraphs 1-11, wherein said preparing the silk powder/particles comprises: (i) freezing a solution comprising silk fibroin at about −20° C. for about 24 hours; (ii) transferring the frozen solution to a temperature of about −80° C. for about 2-3 hours; (iii) lyophilizing the frozen solution at a pressure of about 0.006-100 Torr for about 24-48 hours, or until the silk is completely lyophilized; and (iv) blending the lyophilized solution for 2-3 minutes to produce large particles, or ball milling the lyophilized solution at about 200-350 rpm for about 2-3 hours to produce a silk powder.
13. The method of any of paragraphs 1-12, wherein the composition is in a mold.
14. The method of any of paragraphs 1-13, wherein the mold is of simple geometry or of a pre-defined complex geometry.
15. The method of any of paragraphs 1-14, wherein said forming the green body comprises transferring at least a part of the composition to a mold or forming the composition into a desired shape.
16. The method of any of paragraphs 1-15, wherein said transferring is by hand or high pressure injection.
17. The method of any of paragraphs 1-16, wherein said forming the green body comprises incubating the composition comprising the silk and calcium phosphate material at an elevated temperature.
18. The method of any of paragraphs 1-17, wherein said elevated temperature is from about 30° C. to about 95° C.
19. The method of any of paragraphs 1-18, wherein said elevated temperature is about 60° C.
20. The method of any of paragraphs 1-19, wherein said incubation at the elevated temperature is for about 2 hours to about 72 hours.
21. The method of any of paragraphs 1-20, wherein said incubation at the elevated temperature is for about 6 hours to about 24 hours.
22. The method of any of paragraphs 1-21, wherein said forming the green body comprises freeze-drying the composition comprising the silk and calcium phosphate material.
23. The method of any of paragraphs 1-22, wherein freeze-drying comprises freezing the composition at about −20° C. for about 24 hours and lyophilizing the frozen solution at about 0.006-100 Torr for about 24-28 hours.
24. The method of any of paragraphs 1-23, wherein said forming the green body comprises applying pressure to the composition.
25. The method of any of paragraphs 1-24, wherein said pressure is from about 500 psi to about $10^5$ psi.
26. The method of any of paragraphs 1-25, wherein said pressure if from about 10,000 psi to about 20,000 psi.
27. The method of any of paragraphs 1-26, wherein the pressure is applied for about 5 seconds to about 24 hours.
28. The method of any of paragraphs 1-27, wherein the method comprises: (i) providing a mold comprising silk and the calcium phosphate material; (ii) applying pressure to the composition; (iii) optionally adding additional mixture of silk and the calcium phosphate material to the mold, and applying pressure to the composition; and (v) repeating step (iii) until the green body of desired size has been obtained.
29. The method of any of paragraphs 1-28, further comprising processing the green body to a desired shape before sintering.
30. The method of any of paragraphs 1-29, wherein said processing is selected from the group consisting of machining, turning (lathe), rolling, thread rolling, drilling, milling, sanding, punching, die cutting, blanking, broaching, and any combinations thereof
31. The method any of paragraphs 1-30, wherein said sintering comprises heating the green body to a temperature of about 1200° C.-1500° C.
32. The method of any of paragraphs 1-31, wherein said sintering comprises heating the green body at a temperature of 1300° C.-1400° C.
33. The method of any of paragraphs 1-32, wherein said sintering comprises a linear ramp heating rate of about 5° C./min to about 25° C./min.
34. The method of any of paragraphs 1-33, wherein said sintering comprises a linear ramp heating rate of about 8° C./min.
35. The method of any of paragraphs 1-34, wherein said sintering comprises heating the green body for a period of about 1 hour to about 12 hours.
36. The method of any of paragraphs 1-35, wherein said sintering comprises heating the green body for a period of about 2-3 hours.
37. The method of any of paragraphs 1-36, wherein said sintering comprises heating the green body at a temperature of 1300° C.-1400° C. for 2-3 hours with a linear ramp heating rate of 8° C./minute.
38. The method of any of paragraphs 1-37, further comprising processing the ceramic material of step (ii) to a desired shape.
39. The method of any of paragraphs 1-38, wherein said processing is selected from the group consisting of machining, turning (lathe), rolling, thread rolling, drilling, milling, sanding, punching, die cutting, blanking, broaching, and any combinations thereof.

40. The method of any of paragraphs 1-39, comprising:
   (i) providing in a simple geometry mold the composition comprising the silk and the calcium phosphate material, wherein the composition has a high viscosity;
   (ii) incubating the mold from step (i) at about 60° C. for about 24 hours to produce a green body ceramic blank;
   (iii) optionally storing the green body ceramic blank;
   (iv) sintering the green body blank at a temperature of about 1300° C.-1400° C. for about 2-3 hours; and
   (v) processing the resultant sintered CaP ceramic blank into a desired shape.

41. The method of any of paragraphs 1-40, comprising:
   (i) providing in a simple geometry mold the composition comprising the silk and the calcium phosphate material, wherein the composition has a high viscosity;
   (ii) freeze-drying the composition in the mold from step (i) to produce a green body ceramic blank;
   (iii) optionally storing the green body blank;
   (iv) sintering the green body blank at a temperature of about 1300° C.-1400° C. for about 2-3 hours; and
   (v) processing the resultant sintered CaP ceramic blank into a desired shape.

42. The method of any of paragraphs 1-41, comprising:
   (i) forming the composition comprising the silk and the calcium phosphate material into a shape for processing, wherein the composition has a high viscosity;
   (ii) incubating the shaped composition from step (i) at about 60° C. for about 24 hours to produce a green body ceramic blank;
   (iii) optionally storing the green body ceramic blank;
   (iv) sintering the green body blank at a temperature of about 1300° C.-1400° C. for about 2-3 hours; and.
   (v) processing the resultant sintered CaP ceramic blank into a desired shape.

43. The method of any of paragraphs 1-42, comprising:
   (i) forming the composition comprising the silk and the calcium phosphate material into a shape for processing, wherein the composition has a high viscosity;
   (ii) freeze-drying the shaped composition from step (i) to produce a green body ceramic blank;
   (iii) optionally storing the green body blank;
   (iv) sintering the green body blank at a temperature of about 1300° C.-1400° C. for about 2-3 hours; and
   (v) processing the resultant sintered CaP ceramic blank into a desired shape.

44. The method of any of paragraphs 1-43, comprising:
   (i) providing in a mold or cavity of a pre-defined complex shape the composition comprising the silk and the calcium phosphate material, wherein the composition has a low viscosity;
   (ii) incubating the mold from step (i) at about 60° C. for about 24 hours to produce a green body;
   (iii) optionally storing the green body; and
   (iv) sintering the green body at a temperature of about 1300° C.-1400° C. for about 2-3 hours.

45. The method of any of paragraphs 1-44, comprising:
   (i) providing in a mold or cavity of a pre-defined complex shape the composition comprising the silk and the calcium phosphate material, wherein the composition has a low viscosity;
   (ii) freeze-drying the composition in the mold from step (i) to produce a green body;
   (iii) optionally storing the green body; and
   (iv) sintering the green body at a temperature of about 1300° C.-1400° C. for about 2-3 hours.

46. The method of any of paragraphs 1-45, comprising:
   (i) providing in a mold the composition comprising the silk and the calcium phosphate material, where in the composition is substantially free of solvents;
   (ii) applying pressure to the composition in the mold, thereby reducing volume of the composition in the mold;
   (iii) optionally adding additional composition comprising silk and calcium phosphate material to the mold and applying pressure to the mold;
   (iv) repeating step (iii) to produce a green body of desired size;
   (v) optionally processing the green body to a desired shape; and
   (vi) sintering the green body at a temperature of about 1300° C.-1400° C. for about 2-3 hours.

47. A ceramic material comprising silk and a calcium phosphate material.

48. The ceramic material of paragraph 47, wherein the ceramic material has a density of from about 0.0010 g/cm$^3$ to about 0.0030 g/cm$^3$.

49. The ceramic material of paragraph 47 or 48, wherein the ceramic material has a volume swell ratio of 1.5% or less.

50. The ceramic material of any of paragraphs 47-48, wherein the ceramic material has a compressive toughness of about 1 kJ m$^{-3}$ to about 20 kJm$^{-3}$.

51. The ceramic material of any of paragraphs 47-50, wherein the ceramic material has a compressive strength of about 5 MPa to about 150 MPa.

52. The ceramic material of any of paragraphs 47-51, wherein the ceramic material has a compressive modulus of about 0.25 GPa to about 10 GPa.

53. The ceramic material of any of paragraphs 47-52, wherein the ceramic material has a porosity of less than about 0.7.

54. The ceramic material of any of paragraphs 47-53, wherein the ceramic material comprises pores of size from about 1 to about 1200 microns.

55. The ceramic material of any of paragraphs 47-54, wherein the ceramic material comprises open-cell porosity from about 1% to about 100%.

56. The ceramic material of any of paragraphs 47-55, wherein the ceramic material absorbs upto about 25 wt % of a liquid with a volume swell ratio of about 1.5% or less.

57. The ceramic material of any of paragraphs 47-56, wherein the ceramic material is bioresorbable, biocompatible, osteoconductive, osteogenic, or osteoinductive.

58. The ceramic material of any of paragraphs 47-57, further comprising a bone cell.

59. The ceramic material of any of paragraphs 47-58, wherein the ceramic material is obtained by a method according to any of paragraphs 1-46.

60. A tissue-engineered construct comprising a ceramic material of any of paragraphs 47-59.

61. An implant for the repair, augmentation, or replacement of substantially all or part of one or more bones, or as a substitute for bone grafts in orthopedic applications, the implant comprising a ceramic material of any of paragraphs 47-59.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean ±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "blank" as used herein means an unfinished part of simple geometry that can later be modified by various machining methods to create the desired ceramic shape.

As used herein, the term "simple geometry" means a shape or form characterized by curves or surfaces that that generate a symmetric shape of the rectangular, cylindrical, triangular, or circular variety.

As used herein, the term "complex geometry" means a shape or form characterized by irregular curves or surfaces that generate either a symmetric 3-D shape not of the simple rectangular, cylindrical, triangular, or circular variety (i.e. star, heart), or a completely asymmetric 3-D shape.

As used herein, the term "processing" with reference to a sintered green body should be understood to include any method or process applied to the sintered green body to provide the final shape of the ceramic material. Without limitation, such processing can include, but is not limited to, mechanical and chemical means. For example, processing can be selected from the group consisting of machining, turning (lathe), rolling, thread rolling, drilling, milling, sanding, punching, die cutting, blanking, broaching, and any combinations thereof.

As used herein, the term "machining" should be understood to include all types of machining operations including, but not limited to, cutting, milling, turning, drilling, shaping, planing, broaching, sawing, burnishing, grinding, and the like.

The term 'bone repair' refers to any procedure for repairing bone, including those which use a material as a substitute for bone grafts.

The term 'bone augmentation' refers to the use of any procedure for adding or building bone.

The term 'bone replacement' refers to the use of any procedure for replacing existing bone.

As used herein, the term "microparticle" refers to a particle having a particle size of about 0.01 μm to about 1000 μm.

As used herein, the term "nanoparticle" refers to particle having a particle size of about 0.1 nm to about 1000 nm.

It will be understood by one of ordinary skill in the art that particles usually exhibit a distribution of particle sizes around the indicated "size." Unless otherwise stated, the term "particle size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particles can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30, less than or equal to about 1.25, less than or equal to about 1.20, less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

Geometric Standard Deviation (GSD) can also be used to indicate the narrow size distribution. GSD calculations involved determining the effective cutoff diameter (ECD) at the cumulative less than percentages of 15.9% and 84.1%. GSD is equal to the square root of the ratio of the ECD less than 84.17% to ECD less than 15.9%. The GSD has a narrow size distribution when GSD<2.5. In some embodiments, GSD is less than 2, less than 1.75, or less than 1.5. In one embodiment, GSD is less than 1.8.

The disclosure is further illustrated by the following examples, which should not be construed as limiting. The examples are illustrative only, and are not intended to limit, in any manner, any of the aspects described herein. The following examples do not in any way limit the invention.

EXAMPLES

Calcium Phosphate Ceramic Scaffold Fabrication Process

The process used to generate high strength, complex geometry calcium phosphate (CaP) ceramic scaffolds using silk as a binding agent can be divided into two methods which are: (1) fabrication of complex geometry calcium phosphate scaffolds via machining of sintered calcium phosphte ceramic blanks, and (2) fabrication of complex geometry calcium phosphate scaffolds via injection molding of silk/CaP solutions into molds or cavities of pre-defined shape. Each of these two methods can be further divided into four sections: (A) preparation of concentrated silk solution or silk powder from degummed silk fibers, (B) fabrication of molds or cavities of pre-defined shape for CaP green body casting, (C) preparation of ceramic green bodies using one of the three novel silk processing methods, and (D) high temperature sintering of ceramic green bodies to generate sintered ceramic scaffolds. These are novel calcium phosphate ceramics processing methods that uses silk as a binding agent to create stable calcium phosphate ceramic green bodies, and later the silk acts as a sacrificial polymer during sintering to induce porosity in the finished ceramic scaffold. In addition, the injection molding of a silk/CaP composite material to form stable green bodies of complex shape is a novel concept, as well as the machining of pre-formed CaP scaffolds using silk as a binding agent.

A. Preparation of Concentrated Silk Solution from Degummed Fibers.

A concentrated silk solution from degummed fibers was prepared as follow:

1. Cut dry *B. mori* silkworm cocoons into small pieces with scissors (final weight of one batch of chopped silk cocoon is approximately 5 grams).
2. Prepare separate beakers each with 2 L of distilled water for each batch of chopped silk cocoon and heat water until boiling.
3. Weigh appropriate amount of sodium carbonate to make 0.02M solutions in each 2 L volume of boiling water.
4. Dissolve the sodium carbonate in the boiling water.
5. Add silk cocoon pieces to the 0.02M boiling sodium carbonate solution.
6. Boil the silk cocoons for 20 minutes (maintain a rolling boil).
7. After boiling, transfer the degummed silk fibroin to 2 L of cold, distilled water.
8. Perform three 20-minute washes of the degummed silk fibroin in cold, distilled water to remove all sodium carbonate residue.
9. After the third wash, remove the silk fibroin and squeeze out excess water with hands.
10. Dry the silk fibroin for 24 hours at room temperature.
11. After 24 hours, mass the dried silk fibroin.
12. Prepare 9.3M lithium bromide solution according to the calculation below:
   a. (mass of silk fibroin)×4=total volume of 9.3M LiBr solution.
   b. 86.85 g/mol LiBr*9.3 mol/L*(volume from part a)*1 L/1000 mL=grams of LiBr required.
   c. (volume from part a)*0.8=(volume of water to dissolve LiBr).
13. Incubate the degummed silk fibroin in 9.3M LiBr solution for 4-6 hours at 60° C.
14. After 4-6 hours, remove the dissolved silk fibroin from the 60° C. oven and dialyze the silk solution against distilled water in dialysis cassettes (3,500 molecular weight cut-off) over three days while replacing the water two times per day.
15. After dialysis is complete, remove the silk solution from the dialysis cassettes and centrifuge the solution three times at 8,700 rpm for 20 minutes at 4° C.
16. After centrifuging, inject the silk solution into dialysis cassette (3,500 molecular weight cut-off) and place the cassettes in the 60° C. oven for 5-8 hours to dehydrate the silk solution in order to concentrate it.
17. Continuously remove 0.250 mL samples of the silk solution and dry these samples at 60° C. to determine the weight/volume concentration of the silk.
18. Continue concentrating the silk until a 12-15% w/v silk solution is achieved.

19. Concentrated silk solution can be stored up to one week at 4° C.

B. Fabrication of Silicone Molds for Calcium Phosphate Green Body Casting:

Silicone molds for casting the green bodies were prepares as follow:

1. Use Solidworks 3-D CAD software to generate models of rectangular plates with extruded cylinders of desired height/diameter dimensions to use in making silicone rubber molds.
2. Generate .STL files of the Solidworks models to print the plates via rapid prototyping.
3. Mix Smooth-On DRAGON SKIN0 High-Performance Fast Setting Silicone Rubber part A and part B and cast a negative silicone mold from the plastic plate.
4. De-gas the mixture and cure the silicone mold at 60° C. for 24 hours prior to using it for ceramic casting.

C. Preparation of Calcium Phosphate Ceramic Green Bodies Using Silk.

Green bodies were prepared using one of the following three methods.

Silk Solvent Method:

1. Concentrated silk solution was prepared according to part (A) above.
2. Determine the exact silk concentration by drying 0.250 mL of silk solution in the 60° C. oven for 1-2 hours and massing the resulting silk residue to calculate the weight/volume solution concentration.
3. Prepare CaP ceramic pastes using the concentrated silk solution as a solvent for dissolving the CaP powder as follows:
   a. Obtain a calcium phosphate powder.
   b. To generate 10 grams of ceramic paste with a CaP mass to silk mass ratio of 99/1, mass out 9.9 grams of CaP powder, and calculate necessary volume of silk solution needed to obtain 0.1 gram of silk.
   c. Combine the pre-measured silk solution with the pre-massed CaP powder in a weigh boat and stir gently.
   d. Slowly add small amounts of water to the mixture and continuing stirring until a high viscosity paste consistency is achieved for casting machinable blanks, or a low viscosity slurry consistency for injection molding of silk/CaP solutions.
   e. For method 1 (machinable CaP blanks), pack the paste into silicone molds by hand to create (fabricated according to part (B) above).
   f. For method 2 (injectable silk/CaP solutions), inject the silk/CaP composite into the mold to fill the cavity voids, ensuring that no air bubbles get trapped within the mold.
   g. For both methods, incubate the ceramic-filled molds at 60° C. for 24 hours.
   h. For both methods, after 24 hours carefully remove the ceramic green bodies from the molds and store them at room temperature until sintering.
   i. Steps a-g above can be repeated to generate ceramic green bodies of any mass ratio of CaP to silk.
   j. For method 2, remove the complex geometry part from the injection molding cast and sinter the part at 1300-1400° C. for approximately 3 hours to obtain the finished ceramic part.
   k. For method 1 (machinable CaP blanks), remove the stable green body blank from the silicone mold and sinter at 1300-1400° C. for approximately 3 hours to obtain the sintered ceramic blanks. Machine this blank using a lathe, or other cutting or milling tools, to obtain the desired geometry.

FIG. 1 shows a schematic representation of the silk solvent method used to generate CaP ceramic scaffolds via both method 1 (machinable CaP blanks) or method 2 (injection molding of silk/CaP composites).

Silk Powder Method:

1. Concentrated silk solution was prepared according to part (A) above.
2. Silk powder is generated from the silk solution as follow:
   a. Freeze the silk solution at −20° C. for 24 hours.
   b. After 24 hours, transfer the frozen silk to −80° C. for 2-3 hours to further decrease the temperature before lyophilization.
   c. After 2-3 hours at −80° C., lyophilize the frozen silk at a pressure of 0.006-100 Torr for 24-48 hours or until the silk is completely lyophilized into a sponge/foam.
   d. Remove the silk foams from the lyophilizer but DO NOT stabilize the silk foams using beta-sheet induction methods (i.e. autoclave, water anneal, alcohol anneal).
   e. Blend the silk foams in a conventional kitchen blender on high for 2-3 minutes to generate large silk particles, or ball mill the silk particles at 350 rpm for 2-3 hours to generate a fine silk powder.
3. Prepare CaP ceramic pastes using the silk particles/powder as follows:
   a. Obtain a calcium phosphate powder.
   b. To generate 10 grams of ceramic paste with a CaP mass to silk mass ratio of 99/1, mass out 9.9 grams of CaP and 0.1 grams of silk particles/powder.
   c. Combine the CaP powder with the silk powder in a weigh boat and mix gently.
   l. Slowly add small amounts of water to the mixture and continue stirring until a high viscosity paste consistency is achieved for casting machinable blanks, or a low viscosity slurry consistency for injection molding of silk/CaP solutions.
   d. For method 1 (machinable CaP blanks), pack the paste into silicone molds by hand (fabricated according to part (B) above).
   m. For method 2 (injectable silk/CaP solutions), inject the silk/CaP composite into the mold to fill the cavity voids, ensuring that no air bubbles get trapped within the mold.
   e. For both methods, incubate the ceramic-packed molds at 60° C. for 24 hours.
   f. For both methods, after 24 hours, carefully remove the ceramic green bodies from the molds and store them at room temperature until sintering.
   g. Steps a-g above can be repeated to generate ceramic green bodies of any mass ratio of CaP to silk.
   h. For method 2 (injectable silk/CaP solutions), remove the complex geometry part from the injection molding cast and sinter the part at 1300-1400° C. for approximately 3 hours to obtain the finished ceramic part.
   i. For method 1 (machinable CaP blanks), remove the stable green body blank from the silicone mold and sinter at 1300-1400° C. for approximately 3 hours to obtain the sintered ceramic blanks. Machine this blank using a lathe, or other cutting or milling tools, to obtain the desired geometry.

Figure 2:
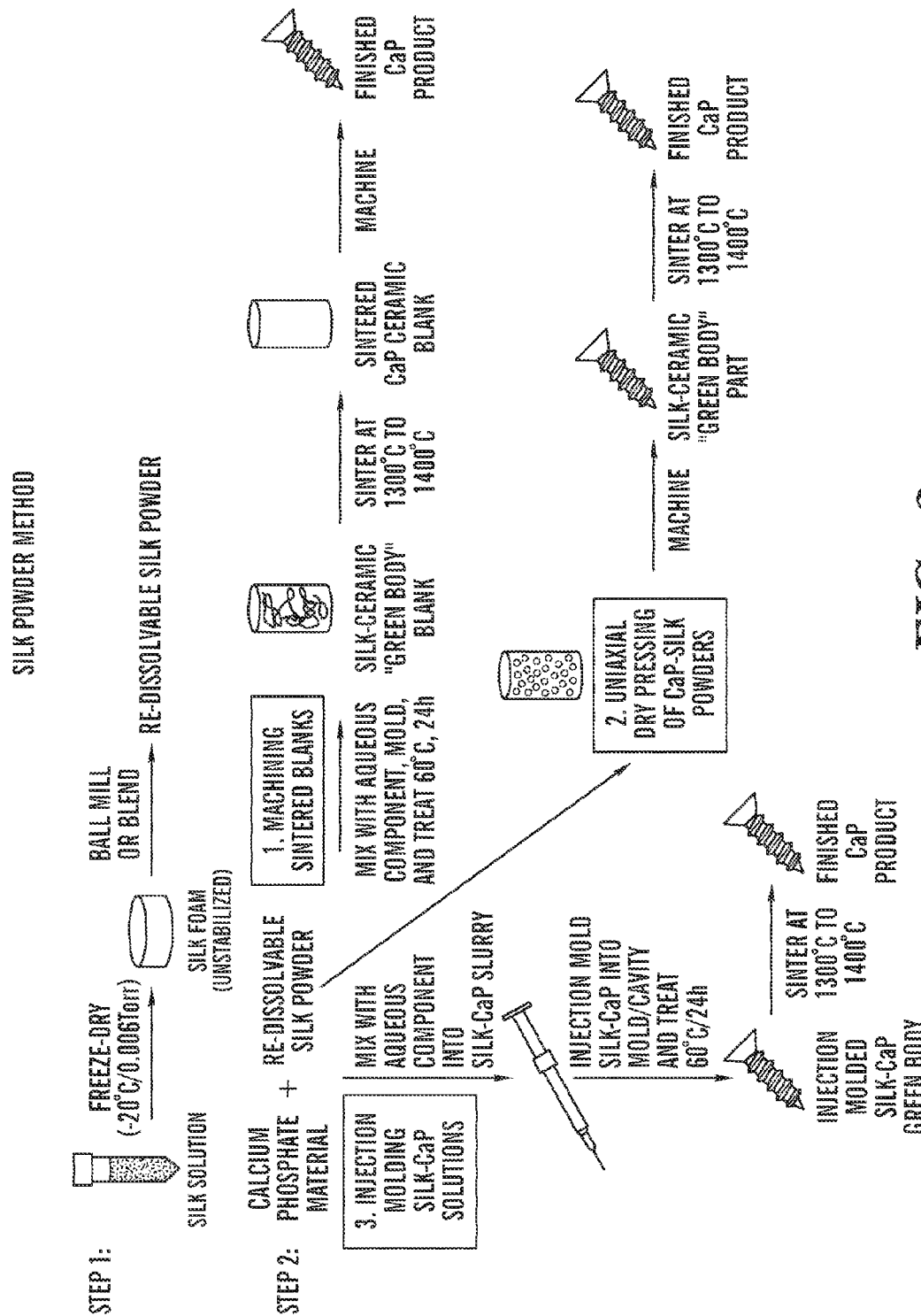
FIG. 2 is a schematic representation of the Silk Powder Method (SPM), which is an exemplary embodiment of a method for preparing CaP ceramic scaffolds using silk via either machining of pre-formed sintered blanks, injection molding of silk/CaP composites, or uniaxial dry pressing of silk-CaP powder mixtures.

FIG. 2 shows a schematic representation of the silk powder method used to generate CaP ceramic scaffolds via both method 1 (machinable CaP blanks) or method 2 (injection molding of silk/CaP composites).

Silk Freeze-Drying Method:
1. Concentrated silk solution was prepared according to part (A) above.
2. Determine the exact concentration of the silk solution by drying 0.250 mL of silk solution in 60° C. oven for 1-2 hours and massing the resulting silk residue to calculate the weight/volume solution concentration.
3. Prepare CaP ceramic pastes using the concentrated silk solution as a solvent for dissolving the CaP powder as follows:
   a. Obtain a calcium phosphate powder.
   b. To generate 10 grams of ceramic paste with a CaP mass to silk mass ratio of 99/1, mass out 9.9 grams of CaP powder, and calculate necessary volume of silk solution needed to obtain 0.1 gram of silk.
   c. Combine the pre-measured silk solution with the pre-massed CaP powder in a weigh boat and stir gently.
   d. Slowly add small amounts of water to the mixture and continuing stirring until a high viscosity paste consistency is achieved for casting machinable blanks, or a low viscosity slurry consistency for injection molding of silk/CaP solutions.
   e. For method 1 (machinable CaP blanks), pack the paste into silicone molds by hand (fabricated according to part (B) above).
   f. For method 2 (injectable silk/CaP solutions), inject the silk/CaP composite into the mold to fill the cavity voids, ensuring that no air bubbles get trapped within the mold.
   g. For both methods, freeze the ceramic-packed silicone molds at −20° C. for at least 24 hours.
   h. For both methods, after 24 hours at −20° C., transfer the molds to the lyophilizer and freeze-dry the ceramic casts at 0.006-100 Torr for 24-48 hours.
   i. For both methods, after 24-48 hours, carefully remove the ceramic green bodies from the molds and store them at room temperature until sintering.
   j. Steps a-h above can be repeated to generate ceramic green bodies of any mass ratio of CaP to silk.
   j. For method 2 (injectable silk/CaP solutions), remove the complex geometry part from the injection molding cast and sinter the part at 1300-1400° C. for approximately 3 hours to obtain the finished ceramic part.
   k. For method 1 (machinable CaP blanks), remove the stable green body blank from the silicone mold and sinter at 1300-1400° C. for approximately 3 hours to obtain the sintered ceramic blanks. Machine this blank using a lathe, or other cutting or milling tools, to obtain the desired geometry.

Figure 3:
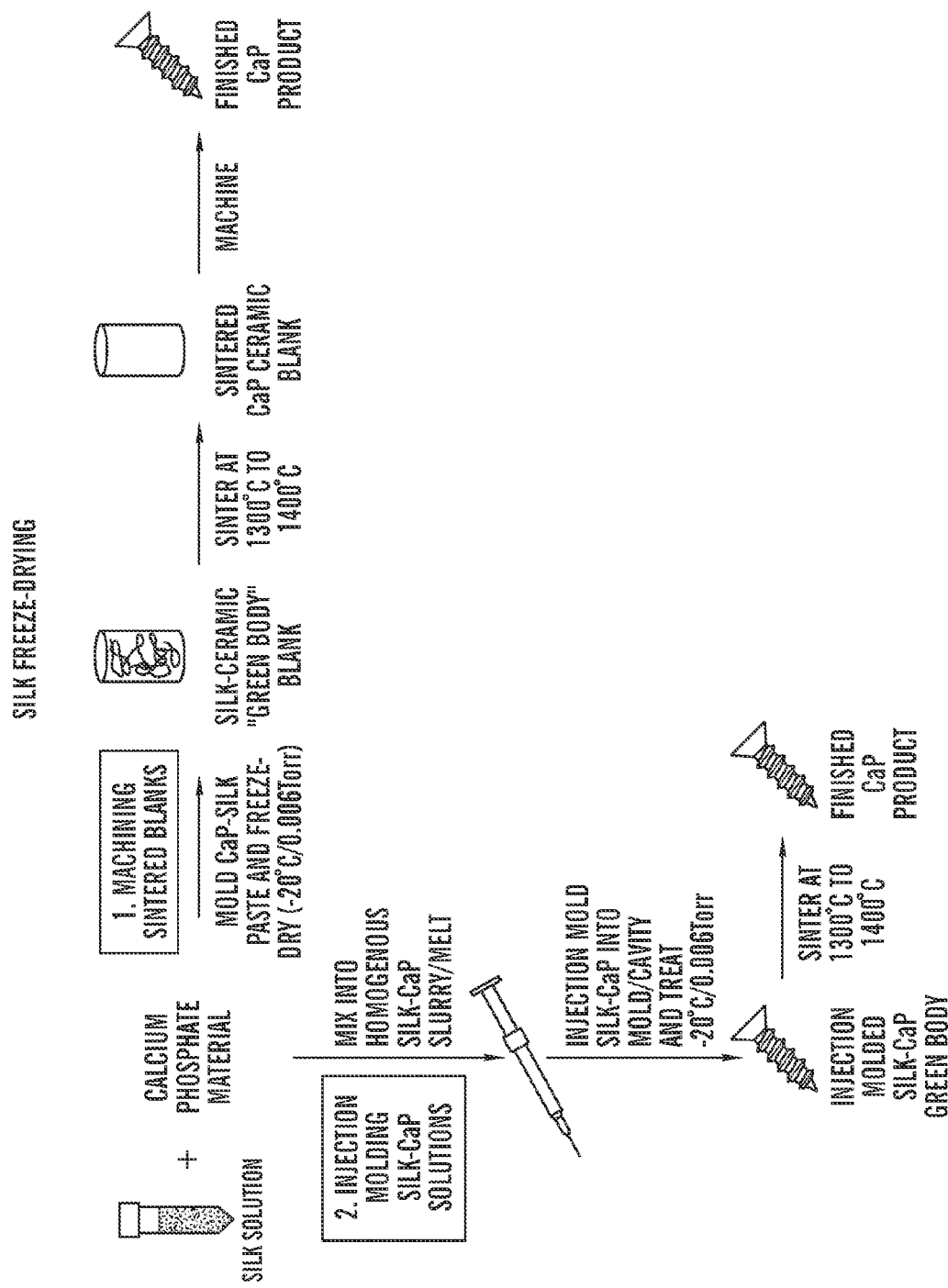
FIG. 3 is a schematic representation of the Silk Freeze-Drying Method (SFD), which is an exemplary embodiment of a method for preparing CaP ceramic scaffolds using silk via either machining of pre-formed sintered blanks, or injection molding of silk/CaP composites.

FIG. 3 shows a schematic representation of the silk freeze-drying method used to generate CaP ceramic scaffolds via both method 1 (machinable CaP blanks) or method 2 (injection molding of silk/CaP composites).

D. High Temperature Sintering of Calcium Phosphate Ceramic Green Bodies.

Green bodies prepared using any of the above-discussed methods were sintered using the following method.
1. Carefully position calcium phosphate ceramic green bodies on a mullite ceramic plate (dimensions: 6"×2"× 0.25" obtained from Ceramco, Inc.).
2. Slide the mullite ceramic plate to the center of the furnace tube (approximately 25 inches from the right side of the furnace tube end).
3. Sinter the ceramic green bodies at 1300° C.-1400° C. in a Lindberg Blue-M Tube Furnace for 3 hours with a linear ramp heating rate of 8° C./minute.
4. After sintering is complete allow the ceramic parts to cool at room temperature before removing them from the furnace.

Alternative CaP processing methods were tried prior to using the three silk processing methods outlined above. These included: (1) Freeze-drying mixtures of CaP powder with water and (2) Freeze-drying mixtures of CaP powder with 5% polyvinyl alcohol (PVA). The protocols for these are discussed below.

Freeze-Drying Mixtures of CaP Powder with Water Protocol:
1. Obtain a calcium phosphate powder.
2. For a CaP mass to water mass ratio of 70/30, mix 7 grams of CaP powder with 3 mL (3 grams) of distilled water
3. Mix well until a high viscosity paste consistency is achieved is achieved for casting machinable blanks, or a low viscosity slurry consistency for injection molding of silk/CaP solutions.
4. For method 1 (machinable CaP blanks), pack the ceramic paste into pre-formed silicone molds by hand (fabricated according to part (B) above).
5. For method 2 (injectable silk/CaP solutions), inject the silk/CaP composite into the mold to fill the cavity voids, ensuring that no air bubbles get trapped within the mold.
6. For both methods, freeze the ceramic-packed molds at −20° C. for 24 hours.
7. For both methods, after 24 hours, transfer the molds to the lyophilizer and freeze-dry the ceramics at 0.006-100 Torr for 24-48 hours.
8. After 24-48 hours, carefully remove the ceramic green bodies from the molds and store at room temperature until sintering.

Freeze-Drying Mixtures of CaP Powder with 5% Polyvinyl Alcohol Protocol:
1. Obtain a calcium phosphate powder, and polyvinyl alcohol (PVA) (Fisher Scientific) powder.
2. Slowly mix PVA into distilled water over gentle heat to create a 5% w/v solution of PVA.
3. For a CaP mass to 5% PVA solution volume ratio of 70/30, mix 7 grams of CaP with 3 mL (2 grams) of 5% PVA solution.
4. Mix well until a high viscosity paste consistency is achieved is achieved for casting machinable blanks, or a low viscosity slurry consistency for injection molding of silk/CaP solutions.
5. For method 1 (machinable CaP blanks), pack the ceramic paste into pre-formed silicone molds (fabricated according to part (B) above).
6. For method 2 (injectable silk/CaP solutions), inject the silk/CaP composite into the mold to fill the cavity voids, ensuring that no air bubbles get trapped within the mold.
7. For both methods, freeze the ceramic-packed molds at −20° C. for 24 hours.
8. For both methods, after 24 hours, transfer the molds to the lyophilizer and freeze-dry the ceramics at 0.006-100 Torr for 24-48 hours.
9. After 24-48 hours, carefully remove the ceramic green bodies from the molds and store at room temperature until sintering.

Due to the low solubility of CaP powder in the 5% PVA solution workable CaP/water ratios that could be created were limited with the PVA solution. Any ratio higher than 70/30 was impossible to fabricate due to the high viscosity and low dissolving ability of the 5% PVA solution. In contrast, silk was successful in stabilizing freeze-dried green bodies.

It is important to note that in these initial studies of using silk as a binding agent for making CaP ceramic scaffolds involved using CaP mass to silk volume ratios instead of CaP mass to silk mass ratios. CaP mass to silk volume ratios can introduce an inaccurate degree of total porosity in the finished scaffold because the water the makes up a majority of the volume of silk added to the CaP evaporates in the oven or during freeze-drying leaving behind only the silk to act as a porogen during sintering. For example, for a CaP mass to silk volume ratio of 70/30, 7 grams of CaP powder were mixed with 3 mL (3 grams) of 6% silk solution to generate a ceramic paste. However, after incubation at 60° C., the water in the 3 grams of silk solution burned off leaving behind only 0.18 grams of silk (0.06 g/mL*3 mL). Thus, the final CaP mass to silk mass ratio in the green body prior to sintering is approximately 97/3. This results in a sintered ceramic that has a much lower total porosity than expected. This should be accounted for during processing. Using mass ratios of CaP to silk, as seen in the silk powder method, can be a much easier and more reproducible method for producing ceramics of varying degrees of porosity. In the silk powder method, the same volume of water can be added to the final CaP-silk dry mixture to create a slurry, thus avoiding the problem that arises in the silk solvent method of having different volumes of silk solution added to the dry CaP.

Exemplary Specific Protocols According to Embodiments of the

Protocol 1: Silk Solvent

I. Preparation of Concentrated Silk Solution
 a. Cut 5 grams of *B. mori* cocoons into small pieces
 b. Boil the cocoon pieces in 2 L of 2M NaCO3 solution for 20 minutes only
 c. Remove the degummed silk fibroin and rinse 3 times for 15-20 minutes in distilled water
 d. Separate fibers and dry at ambient conditions for 24-48 hours
 e. Mass the dried fibroin
 f. Calculate grams of LiBr needed to create 9.3M solution to dissolve fibroin:
  i. (mass of fibroin)×4=total mL of 9.3M LiBr solution
  ii. 86.85 g/mol×9.3 mol/L×(volume from part i)×($\frac{1}{1000}$)=g LiBr
  iii. 0.8×(volume from part i)=mL of water to add to grams from part ii
 g. Dissolve silk in 9.3M LiBr for 4-6 hours at 600 C
 h. Dialyze dissolved silk solution against distilled water for 2-3 days until LiBr has been removed
 i. Concentrate resulting silk solution to 15% w/v by dialyzing against 10% PEG or dehydrating the silk in a dialysis cassette at ambient conditions for 10-15 hours.
 j. NOTE: Concentrated 15% w/v 20-minute boil silk solution can be safely stored in refrigerator for approximately 2 weeks. Ensure there are no bubbles in the tube to minimize the potential of gelation.

II. Preparation of Silk-Calcium Phosphate Green Body Ceramics
 a. Obtain hydroxyapatite (of two different particle sizes—called "HA1" and "HA2") from Fisher Scientific (AC37126-0010 Acros Organic No.: 371260010)
 b. NOTE: water volumes provided in Table 2 below have been optimized specifically for the ceramic powders listed in part a. Other types of calcium phosphate powders, or other CaP powders obtained elsewhere may have different solubility values.
 c. One "batch" of ceramic material is considered 20 grams total material
 d. NOTE: Batch size can be adjusted depending on how much material is required to form the green body or bodies, and water volumes will be adjusted proportionately. For example, a batch of 10 grams total material would only require half the volume of water listed in Table 2.
 e. For a 90% CaP/10% silk by mass green body ceramic:
 i. Mass out 18.0 g of CaP
 ii. Calculate volume of silk solution required for 2.0 g of silk (for a 15% w/v silk solution, this is exactly 13.34 mL)
 iii. If the CaP is hydroxyapatite 1 add 12.0 mL of water to the 13.34 mL of 15% w/v silk solution in a falcon tube (see Table 2)
 iv. If the CaP is hydroxyapatite 2, add 8.0 mL of water to the 13.34 mL of 15% w/v silk solution in a falcon tube (see Table 2)
 v. Mix the liquid and powder components together vigorously until a homogeneous paste consistency is achieved (should be the consistency of clay or play dough)
 vi. NOTE: water volumes in Table 2 have been optimized to achieve a moldable paste consistency with an error of +/−2 mL of water. If the indicated volume in Table 2 inadequately solubilizes all of the dry CaP powder add an additional 1-2 mL of water in increments of 0.5 mL with continued mixing. If the indicated volume in Table 2 is too much (meaning the paste is too sticky or not viscous enough to mold) then leave the paste at ambient conditions for 15-20 minutes with periodic mixing to allow some of the water to evaporate until a thicker paste is achieved. DO NOT DEHYDRATE THE PASTE IN AN OVEN OR EXPOSE TO ELEVATED TEMPERATURES.
 vii. NOTE: Lower ratios of CaP/silk (containing more silk by mass) will produce much stickier pastes that are harder to mold. Dehydrating the paste slightly at room temperature will help to reduce the stickiness.
 viii. After mixing the liquid and powder components into homogeneous, moldable paste, green bodies can be created by either hand molding the paste into the desired shape or by packing the paste into a silicone mold.
 ix. To stabilize the green body, immediately incubate the molded parts at 600 C for at least 24 hours (larger parts will require more time to dry and harden).
 x. After incubation, green bodies can be removed from 60° C. and stored at dry ambient conditions until sintering.
 f. Sinter green body ceramics in air at 1300-1400° C. for at least 3 hours.
 g. NOTE: Green bodies with shrink approximately 60% in each dimension upon sintering. Shrink factor must be calculated into green body dimensions.

TABLE 2

Water volumes for creating moldable CaP-
silk pastes using Silk Solvent Method.

| CaP-Silk Mass Ratio | Hydroxyapatite 1 (HA1) | Hydroxyapatite 2 (HA2) |
|---|---|---|
| 99/1 | 24.0 mL | 16.0 mL |
| 90/10 | 12.0 mL | 8.0 mL |
| 80/20 | 0 mL | 0 mL |

* Batch size = 20 grams total dry material; ambient conditions (appx. 20° C.)
Note:
Water is mixed with 15% w/v silk solution prior to mixing with dry calcium phosphate.

Protocol 2: Silk Powder
I. Preparation of Dissolvable Silk Powder
  a. Cut 5 grams of *B. mori* cocoons into small pieces
  b. Boil the cocoon pieces in 2 L of 2M NaCO3 solution for 60 minutes only
  c. Remove the degummed silk fibroin and rinse 3 times for 15-20 minutes in distilled water
  d. Separate fibers and dry at ambient conditions for 24-48 hours
  e. Mass the dried fibroin
  f. Calculate grams of LiBr needed to create 9.3M solution to dissolve fibroin:
    i. (mass of fibroin)×4=total mL of 9.3M LiBr solution
    ii. 86.85 g/mol×9.3 mol/L×(volume from part i)×(1/1000)=g LiBr
    iii. 0.8×(volume from part i)=mL of water to add to grams from part ii
  g. Dissolve silk in 9.3M LiBr for 4-6 hours at 60° C.
  h. Dialyze the dissolved silk solution against distilled water for 2-3 days until the LiBr has been removed
  i. Adjust the concentration of the resulting silk solution to 6% w/v by diluting if the raw solution is above 6% or dialyzing against 10% PEG or dehydrating the silk in a dialysis cassette at ambient conditions if the concentration is below 6%. NOTE: the concentration of the raw solution that you obtain after removing from dialysis is usually around 5-7% w/v.
  j. Pour the 6% w/v 60-minute boil silk solution into six-well tissue culture plates and freeze at −20° C. for 24 hours.
  k. After 24 hours at −20° C., lyophilize the frozen silk at a pressure between 0.006-100 Torr for 24-48 hours.
  l. After lyophilizing, carefully remove the silk foams from the six-well plate with forceps and blend in a conventional kitchen blender on high for 1-2 minutes.
  m. NOTE: After lyophilizing, DO NOT expose silk foams to water or alcohol solutions, or to high humidity conditions. DO NOT expose silk foams to heat conditions. Silk foams can be stored at dry ambient conditions for several months before blending.
  n. NOTE: Do not blend for longer than 2 minutes since heat generation from the blades will induce beta-sheet formation in the silk and affect solubility of the powder. Do not use a ball mill or other grinding equipment to turn the foams into powder as this will also create too much heat due to friction.
  o. After blending, silk powder can be stored at dry ambient conditions for several months before use.
II. Preparation of Silk-Calcium Phosphate Green Body Ceramics
  a. Obtain hydroxyapatite (of two different particle sizes—called "HA1" and "HA2") from Fisher Scientific (AC37126-0010 Acros Organic No.: 371260010)
  b. NOTE: water volumes provided in Table 3 below have been optimized specifically for the ceramic powders listed in part a. Other types of calcium phosphate powders, or other CaP powders obtained elsewhere may have different solubility values.
  c. One "batch" of ceramic material is considered 20 grams total material
  d. NOTE: Batch size can be adjusted depending on how much material is required to form the green body or bodies, and water volumes will be adjusted proportionately. For example, a batch of 10 grams total material would only require half the volume of water listed in Table 3.
  e. For a 90% CaP/10% silk by mass green body ceramic:
    i. Mix 18.0 g of calcium phosphate and 2.0 g dry silk powder together either by hand or using a conventional blender, ensuring homogeneity in the mixture.
    ii. If the CaP is hydroxyapatite 1, add 21.0 mL of water to the CaP-silk powder mixture (see Table 3).
    iii. If the CaP is hydroxyapatite 2, add 14.0 mL of water to the CaP-silk powder mixture (see Table 3).
    iv. Mix the liquid and powder components together vigorously until a homogeneous paste consistency is achieved (should be the consistency of clay or play dough)
    v. NOTE: water volumes in Table 3 have been optimized to achieve a moldable paste consistency with an error of +/−2 mL of water. If the indicated volume in Table 3 inadequately solubilizes all of the dry CaP powder add an additional 1-2 mL of water in increments of 0.5 mL with continued mixing. If the indicated volume in Table 3 is too much (meaning the paste is too sticky or not viscous enough to mold) then leave the paste at ambient conditions for 15-20 minutes with periodic mixing to allow some of the water to evaporate until a thicker paste is achieved. DO NOT DEHYDRATE THE PASTE IN AN OVEN OR AT ELEVATED TEMPERATURES.
    vi. NOTE: Lower ratios of CaP/silk (containing more silk by mass) will produce much stickier pastes that are harder to mold. Dehydrating the paste slightly at room temperature will help to reduce the stickiness.
    vii. After mixing the liquid and powder components into homogeneous, moldable paste, green bodies can be created by either hand molding the paste into the desired shape or by packing the paste into a silicone mold.
    viii. To stabilize the green body, immediately incubate the molded parts at 60° C. for at least 24 hours (larger parts will require more time to dry and harden).
    ix. After incubation, green bodies can be removed from 60° C. and stored at dry ambient conditions until sintering.
  f. Sinter green body ceramics in air at 1300-1400° C. for at least 3 hours.
  g. NOTE: Green bodies with shrink approximately 60% in each dimension upon sintering. Shrink factor must be calculated into green body dimensions.

TABLE 3

Water volumes for creating moldable CaP-
silk pastes using Silk Powder Method.

| CaP-Silk Mass Ratio | Hydroxyapatite 1 (HA1) | Hydroxyapatite 2 (HA2) |
|---|---|---|
| 99/1 | 24.0 mL | 16.0 mL |
| 90/10 | 21.0 mL | 14.0 mL |
| 80/20 | 18.0 mL | 12.0 mL |

\* Batch size = 20 grams total dry material; ambient conditions (appx. 20° C.)
Note:
CaP and silk powders are mixed in dry state prior to adding liquid component.

Protocol 3: Silk Freeze-Drying
I. Preparation of Concentrated Silk Solution
   a. Cut 5 grams of *B. mori* cocoons into small pieces
   b. Boil the cocoon pieces in 2 L of 2M NaCO3 solution for 20 minutes only
   c. Remove the degummed silk fibroin and rinse 3 times for 15-20 minutes in distilled water
   d. Separate fibers and dry at ambient conditions for 24-48 hours
   e. Mass the dried fibroin
   f. Calculate grams of LiBr needed to create 9.3M solution to dissolve fibroin:
      i. (mass of fibroin)×4=total mL of 9.3M LiBr solution
      ii. 86.85 g/mol×9.3 mol/L×(volume from part i)×(1/1000)=g LiBr
      iii. 0.8×(volume from part i)=mL of water to add to grams from part ii
   g. Dissolve silk in 9.3M LiBr for 4-6 hours at 60° C.
   h. Dialyze dissolved silk solution against distilled water for 2-3 days until LiBr has been removed
   i. Concentrate resulting silk solution to 15% w/v by dialyzing against 10% PEG or dehydrating the silk in a dialysis cassette at ambient conditions for 10-15 hours.
   j. NOTE: Concentrated 15% w/v 20-minute boil silk solution can be safely stored in refrigerator for approximately 2 weeks. Ensure there are no bubbles in the tube to minimize the potential of gelation.
II. Preparation of Silk-Calcium Phosphate Green Body Ceramics
   a. Obtain hydroxyapatite (of two different particle sizes—called "HA1" and "HA2") from Fisher Scientific (AC37126-0010 Acros Organic No.: 371260010)
   b. NOTE: water volumes provided in Table 4 below have been optimized specifically for the ceramic powders listed in part a. Other types of calcium phosphate powders, or other CaP powders obtained elsewhere may have different solubility values.
   c. One "batch" of ceramic material is considered 20 grams total material
   d. NOTE: Batch size can be adjusted depending on how much material is required to form the green body or bodies, and water volumes will be adjusted proportionately. For example, a batch of 10 grams total material would only require half the volume of water listed in Table 4.
   e. For a 90% CaP/10% silk by mass green body ceramic:
      i. Mass out 18.0 g of CaP
      ii. Calculate volume of silk solution required for 2.0 g of silk (for a 15% w/v silk solution, this is exactly 13.34 mL)
      iii. If the CaP is hydroxyapatite 1, add 12.0 mL of water to the 13.34 mL of 15% w/v silk solution in a falcon tube (see Table 4)
      iv. If the CaP is hydroxyapatite 2, add 8.0 mL of water to the 13.34 mL of 15% w/v silk solution in a falcon tube (see Table 4)
      v. Mix the liquid and powder components together vigorously until a homogeneous paste consistency is achieved (should be the consistency of clay or play dough)
      vi. NOTE: water volumes in Table 2 have been optimized to achieve a moldable paste consistency with an error of +/−2 mL of water. If the indicated volume in Table 4 inadequately solubilizes all of the dry CaP powder add an additional 1-2 mL of water in increments of 0.5 mL with continued mixing. If the indicated volume in Table 4 is too much (meaning the paste is too sticky or not viscous enough to mold) then leave the paste at ambient conditions for 15-20 minutes with periodic mixing to allow some of the water to evaporate until a thicker paste is achieved. DO NOT DEHYDRATE THE PASTE IN AN OVEN OR AT ELEVATED TEMPERATURES.
      vii. NOTE: Lower ratios of CaP/silk (containing more silk by mass) will produce much stickier pastes that are harder to mold. Dehydrating the paste slightly at room temperature will help to reduce the stickiness.
      viii. After mixing the liquid and powder components into homogeneous, moldable paste, green bodies can be created by either hand molding the paste into the desired shape or by packing the paste into a silicone mold.
      ix. To stabilize the green body, immediately freeze the molded parts at −20° C. for 24-48 hours (larger parts will require more time to freeze).
      x. After freezing, carefully remove the parts from the silicone mold (without significant thawing) and lyophilize the parts at a pressure between 0.006-100 Torr for 24-48 hours.
      xi. After lyophilizing, green bodies can be removed from 60° C. and stored at dry ambient conditions until sintering.
      xii. NOTE: The freeze-dried ceramic green bodies are not as structurally stable as those in the silk solvent and silk powder methods that are stabilized via oven heating, and should be handled more carefully.
   f. Sinter green body ceramics in air at 1300-1400° C. for at least 3 hours.
   g. NOTE: Green bodies with shrink approximately 60% in each dimension upon sintering. Shrink factor must be calculated into green body dimensions.

TABLE 4

Water volumes for creating moldable CaP-
silk pastes using Silk Freeze-Drying.

| CaP-Silk Mass Ratio | Hydroxyapatite 1 (HA1) | Hydroxyapatite 2 (HA2) |
|---|---|---|
| 99/1 | 24.0 mL | 16.0 mL |
| 90/10 | 12.0 mL | 8.0 mL |
| 80/20 | 0 mL | 0 mL |

\* Batch size = 20 grams total dry material; ambient conditions (appx. 20° C.)
Note:
Water is mixed with 15% w/v silk solution prior to mixing with dry calcium phosphate.

Protocol 4: CaP-Silk Dry Pressing
I. Preparation of Dissolvable Silk Powder
   a. Cut 5 grams of *B. mori* cocoons into small pieces
   b. Boil the cocoon pieces in 2 L of 2M NaCO3 solution for 60 minutes only
   c. Remove the degummed silk fibroin and rinse 3 times for 15-20 minutes in distilled water
   d. Separate fibers and dry at ambient conditions for 24-48 hours
   e. Mass the dried fibroin
   f. Calculate grams of LiBr needed to create 9.3M solution to dissolve fibroin:
      i. (mass of fibroin)×4=total mL of 9.3M LiBr solution
      ii. 86.85 g/mol×9.3 mol/L×(volume from part i)×(1/1000)=g LiBr
      iii. 0.8×(volume from part i)=mL of water to add to grams from part ii
   g. Dissolve silk in 9.3M LiBr for 4-6 hours at 60° C.
   h. Dialyze the dissolved silk solution against distilled water for 2-3 days until the LiBr has been removed
   i. Adjust the concentration of the resulting silk solution to 6% w/v by diluting if the raw solution is above 6% or dialyzing against 10% PEG or dehydrating the silk in a dialysis cassette at ambient conditions if the concentration is below 6%. NOTE: the concentration of the raw solution that you obtain after removing from dialysis is usually around 5-7% w/v.
   j. Pour the 6% w/v 60-minute boil silk solution into six-well tissue culture plates and freeze at −20° C. for 24 hours.
   k. After 24 hours at −20° C., lyophilize the frozen silk at a pressure between 0.006-100 Torr for 24-48 hours.
   l. After lyophilizing, carefully remove the silk foams from the six-well plate with forceps and blend in a conventional kitchen blender on high for 1-2 minutes.
   m. NOTE: After lyophilizing, DO NOT expose silk foams to water or alcohol solutions, or to high humidity conditions. DO NOT expose silk foams to heat conditions. Silk foams can be stored at dry ambient conditions for several months before blending.
   n. NOTE: Do not blend for longer than 2 minutes since heat generation from the blades will induce beta-sheet formation in the silk and affect solubility of the powder. Do not use a ball mill or other grinding equipment to turn the foams into powder as this will also create too much heat due to friction.
   o. After blending, silk powder can be stored at dry ambient conditions for several months before use.
II. Preparation of Silk-Calcium Phosphate Green Body Ceramics
   a. Obtain hydroxyapatite (of two different particle sizes—"HA1" and "HA2") from Fisher Scientific (AC37126-0010 Acros Organic No.: 371260010)
   b. For a 90% CaP/10% silk by mass green body ceramics:
      i. Mix 18.0 g of calcium phosphate and 2.0 g dry silk powder together either by hand or using a conventional blender, ensuring homogeneity in the mixture.
      ii. Assemble a three-part steel mold to use for powder pressing
      iii. NOTE: Three-part molds (two halves held together with screws and a piston) make it easier to remove the part after pressing. Do not completely tighten the screws before pressing since the mold will expand during pressing and prevent the screws from releasing. It is also important to use steel since the pressures used in this technique will exceed the yield strength of aluminum.
      iv. Fill the mold with the dry CaP/silk mixture and pack it down by hand with the steel piston. Repeat until no more powder can be hand packed into the mold.
      v. Insert the piston in place and apply 10,000-20,000 psi for at least 30 seconds before releasing.
      vi. Release the press and pull the piston out, and repeat steps iv and v until a large enough part has been pressed.
      vii. Dissemble the mold and carefully remove the pressed part.
      viii. Pressed green body blanks can be machined into three-dimensional shapes with lathe and milling equipment.
      ix. After machining, the green part can be sintered at 1300-1400° C. for at least 3 hours to obtain a finished product. It does not need to be sintered, however, due to its inherently high density after pressing.
      x. NOTE: Parts pressed at 10,000 psi will shrink approximately 20% in each dimension. Parts pressed at 20,000 psi will shrink approximately 10% in each dimension.

Materials and Methods

Rheology:

Rheology tests were carried out on an ARES rheometer with a cone (25 mm, 0.1 rad) and plate (50 mm) set-up. Three different silk-CaP composites were tested (99% CaP/1% silk, 90% CaP/10% silk, 80% CaP/20% silk) and a control (100% CaP/0% silk). For each of these groups, three powder-to-liquid ratios were tested (P/L 0.5, 0.6, 0.7). A sample size of N=3 was tested for each group. Steady rate sweep (0-100 $s^{-1}$ shear rate) and dynamic frequency sweep (0.1-100 $s^{-1}$ shear rate) testing was performed on the samples.

Particle Size Analysis:

Mean particle size and particle size distribution was assessed using light scattering analysis. A Horiba LA-300 Laser Diffraction Particle Size Distribution Analyzer was used to assess the mean particle size and size distribution using 70% isopropanol medium. Several different silk powders (made from 20 to 90 minute-boil silk fibroin) were analyzed, along with hydroxyapatite powder. Shown above is 20 minute-boil, 60 minute-boil, and 90 minute-boil silk powder at 6% w/v initial solution concentration. The 60 minute-boil powder was chosen for the Silk Powder Method due to its excellent solubility and ease of production.

Shrink Analysis:

Cylindrical silk-ceramic green bodies (N=10) were measured and massed prior to sintering. They were then sintered at either 1300° C. or 1400° C. with a linear heating rate of 8° C./minute and at max temperature for 3 hours. After sintering, samples were again measured and massed to determine the loss of mass and decrease in volume associated with the sintering process.

Scanning Electron Microscopy:

Sintered CaP scaffolds (N=3) were prepared by first drying the scaffolds completely for 24 hours at 60° C. They were then fractured into pieces. The inner portions of the scaffolds were coated with a thin layer of gold using a sputter coater prior to imaging.

Compression Testing:

Sintered CaP scaffolds were machined into symmetric cylindrical samples for mechanical testing using a two-axis lathe with carbide-tipped tool bit. Samples were then subject to compression testing using an Instron mechanical tester with a 10 kN load cell. The crosshead speed was set to 2 mm/minute and the load was applied until the sample was crushed completely. Note that some samples did not break under 10,000N of force, at which point the machine shut off automatically to protect the load cell.

Pore Size Analysis:

Morphological analysis and pore size determination was performed using scanning electron microscopy. Scaffolds (N=3) were prepared as previously described. Three images for each scaffold were processed using ImageJ software to measure the pore diameter of five randomly selected pores in each image.

Porosity Analysis:

Liquid displacement was used to determine the total porosity of the sintered CaP ceramics. Specifically, pure ethanol (100%) was selected as the liquid for these measurements since sintered calcium phosphate material does not absorb or swell in 100% ethanol. Scaffolds (N=6) were first massed to obtain the dry weight ($W_d$). Scaffolds were then immersed in a known volume ($V_1$) of ethanol. The scaffolds were then placed under vacuum for 30 minutes to force the ethanol into the pores of the scaffold until air bubbles no longer emerged from the scaffolds. The total volume of the ethanol and the scaffold was recorded as $V_2$. The volume difference ($V_2-V_1$) was taken as the volume of the scaffold skeleton. The scaffolds were then removed from the ethanol and the residual volume of ethanol was measured as $V_3$. The total volume of each scaffold could therefore be calculated as $V=V_2-V_3$ and the porosity of the open pores in the scaffold, P was calculated as $P=(V_1-V_3)/(V_2-V_3)$.

Micro-CT:

Micro-computed tomography imaging (N=1) was conducted at the Center for Nanoscale Systems at Harvard University. The sintered CaP samples were scanned using a voltage of 75 kV and a current of 135 uA at one-second exposure and 25× magnification.

Xray Diffraction:

Sample phases were identified using x-ray diffraction testing. Samples (N=1) were scanned in a Scintag XDS-2000 diffractometer using CuKα radiation operated at 40 kV and 100 mA at a 2θ range of 25-55° with a step size of 0.02° Different phases were identified in the material depending on sintering temperature and location within the sample. As shown in the data, most of the samples contained a mixture of hydroxyapatite and alpha-tricalcium phosphate after sintering and are therefore considered "biphasic" materials post-sintering.

Alamar Blue Assay:

Human bone marrow stem cells were seeded on sintered CaP scaffolds at a density of 150,000 cells per scaffold and cultured in Dulbecco's Modified Eagle Medium (DMEM) with high glucose and GlutaMax containing 10% fetal bovine serum and 1% antibiotic-antimycotic. Cells were maintained at 37° C. in a 5% $CO_2$ incubator. Cell proliferation rates on CaP scaffolds were analyzed by Alamar blue (Life Technologies) at days 1, 4, 8, and 12 according to the manufacturer's protocol. Cell number at each time point was normalized to seeding day 0. On day 14, the seeded scaffolds were incubated in Live/Dead stain (Invitrogen) according to the manufacturer's protocol. Confocal microscopy was carried out on the stained samples using 488 nm and 543 nm laser excitation to assess cell morphology, distribution, and proliferation of cells within and on the surfaces of the scaffolds.

Silk Macroporogen Production:

Large non-soluble silk macroporogens (SMPs) are fabricated in a similar way to the soluble silk powder for the Silk Powder Method. The main difference is that the SMPs are stabilized via methanol annealing once they have been blended in particles to prevent them from dissolving in water. They can then be added to ANY of the methods described in FIGS. 1-3 in order to create a higher porosity ceramics. Once the SMPs have been made, they can be separated based on size (using molecular sieves) to collect fractions of different size particles for pore size control.

Results and Discussion

Table 5 provides exemplary minimum water volumes needed for preparing the Silk/CaP compositions for use in the methods disclosed herein. As can be seen, the amount of water (or other aqueous medium) needed to dissolve the calcium phosphate and silk into a homogenous mixture is dependent on the type of calcium phosphate as well as the particle size (as noted with differences between HA1 and HA2). Further, the amount of water also differs for different % CaP-% silk compositions. HA1 and HA2 (two different hydroxyapatite powders) have different particle size which affects the amount of water needed to dissolve them into solution. It also in turn affects their rheological properties.

TABLE 5

Exemplary Minimum Water Volumes for Scaffold Casting*

| CaP/Silk Mass Ratio | Silk Solvent Method (SSM) | Silk Powder Method (SPM) | Silk Freeze-Dry Method (SFD) |
|---|---|---|---|
| HA1[+] 99/1 | 24.0 mL | 24.0 mL | 24.0 mL |
| HA1[+] 90/10 | 12.0 mL | 21.0 mL | 12.0 mL |
| HA1[+] 80/20 | 0 mL | 18.0 mL | 0 mL |
| HA2[++] 99/1 | 16.0 mL | 16.0 mL | 16.0 mL |
| HA2[++] 90/10 | 8.0 mL | 14.0 mL | 8.0 mL |
| HA2[++] 80/20 | 0 mL | 12.0 mL | 0 mL |

Figure 4:
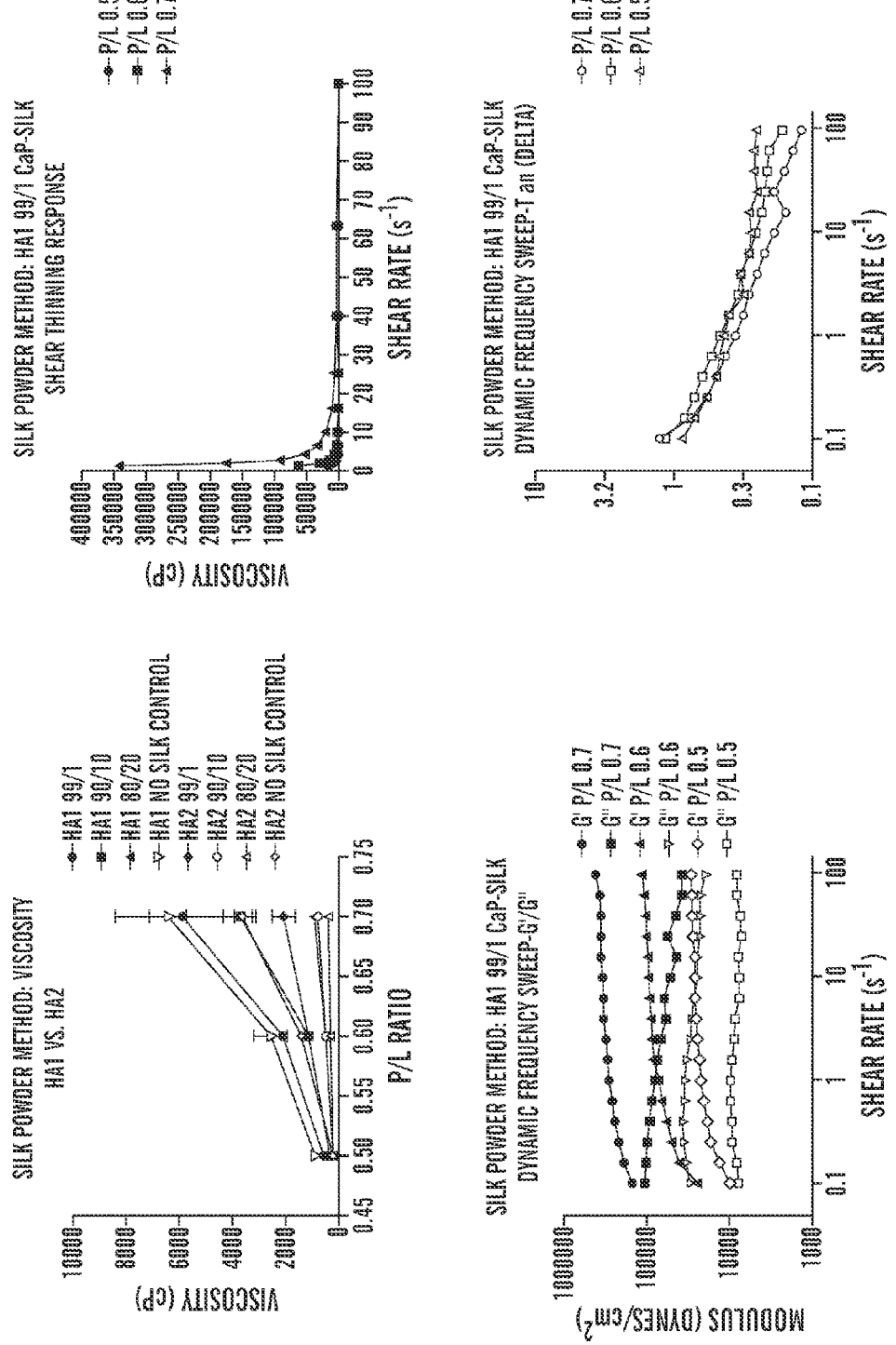
FIG. 4 shows rheological characterization of aqueous based silk-CaP composites prepared according to embodiments of the Silk Powder Method.
Figure 5:
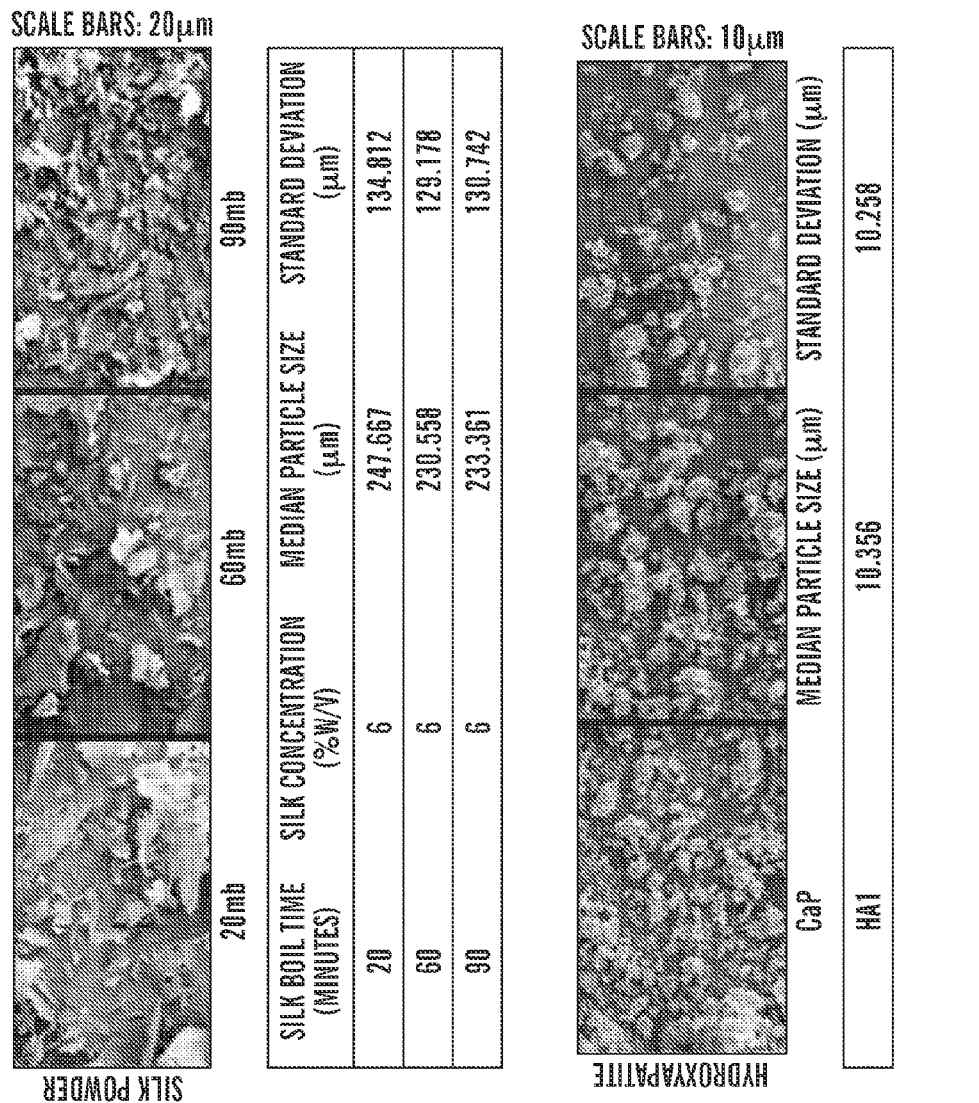
FIG. 5 shows SEM images of silk (top) and CaP (bottom) powders, and average particle size.

*Batch size = 20 g total dry material; ambient conditions (appx. 20° C.)
[+]HA1 = Fisher Scientific Hydroxyapatite CAS 1306-06-5 $HCa_5O_{13}P_3$
[++]HA2 = Fisher Scientific Calcium Phosphate Hydrate CAS 7758-87-4 $HCa_5O_{13}P_3$ Further, lower CaP/Silk mass ratios (e.g., for the Silk Powder Method) produce CaP-Silk solutions that tended to have lower viscosities (FIG. 4 and data not shown). Without wishing to be bound by a theory, this is because the silk solution can have a much lower viscosity than the CaP material if the silk has low molecular weight. One can tailor this to a given application by using silk of different boil times. CaP-Silk solution composites of a higher powder to liquid ratio tended to have higher bulk and storage moduli (FIG. 4 and data not shown). However, regardless of the CaP/silk mass ratio, all Silk-CaP solution composites that were tested demonstrated shear thinning behavior under a steadily increasing shear rate (FIG. 4 and data not shown).

Figure 6:
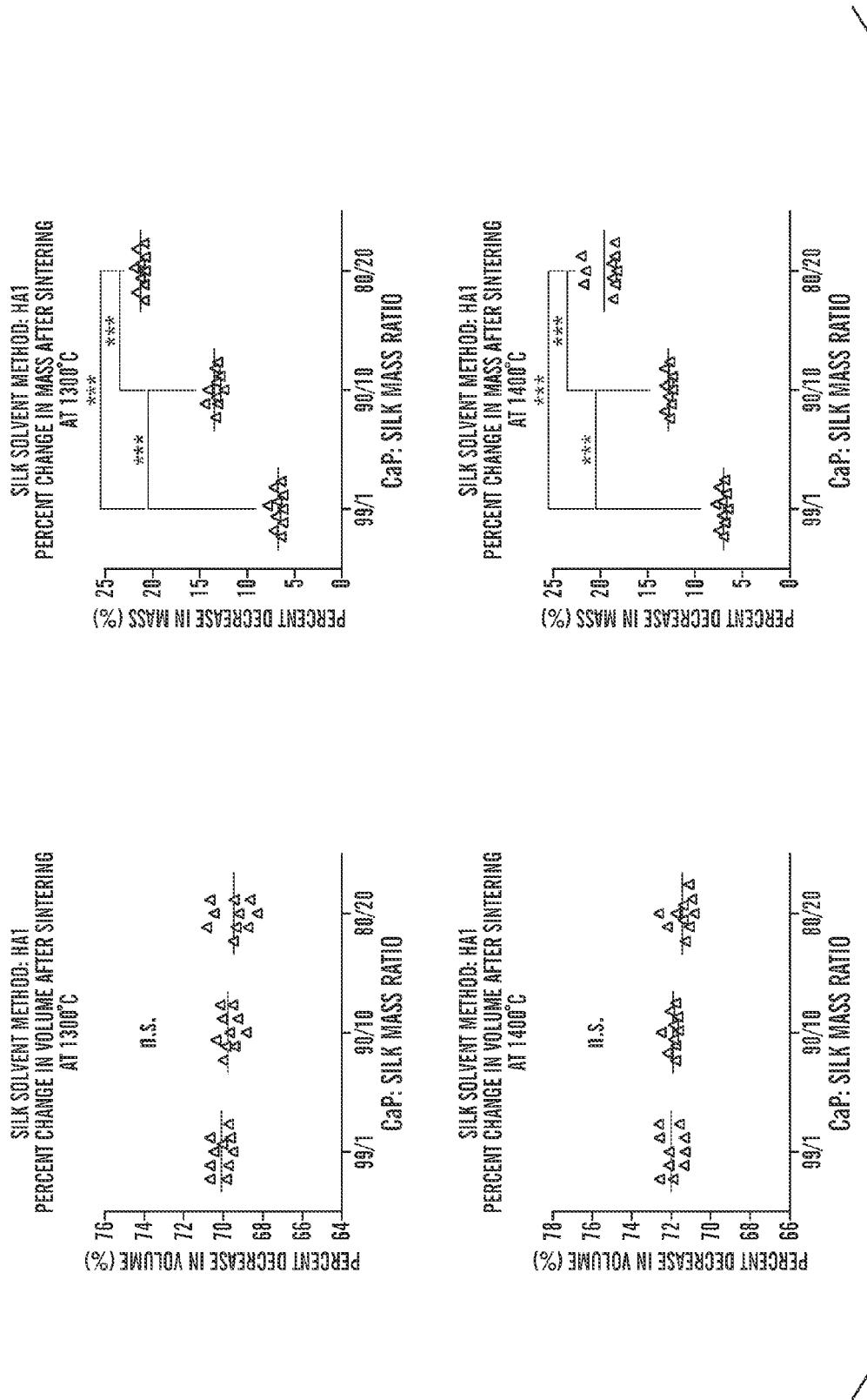
FIG. 6 shows shrink analysis of silk-CaP green bodies prepared according to embodiments of the Silk Solvent Method during sintering.
Figure 7:
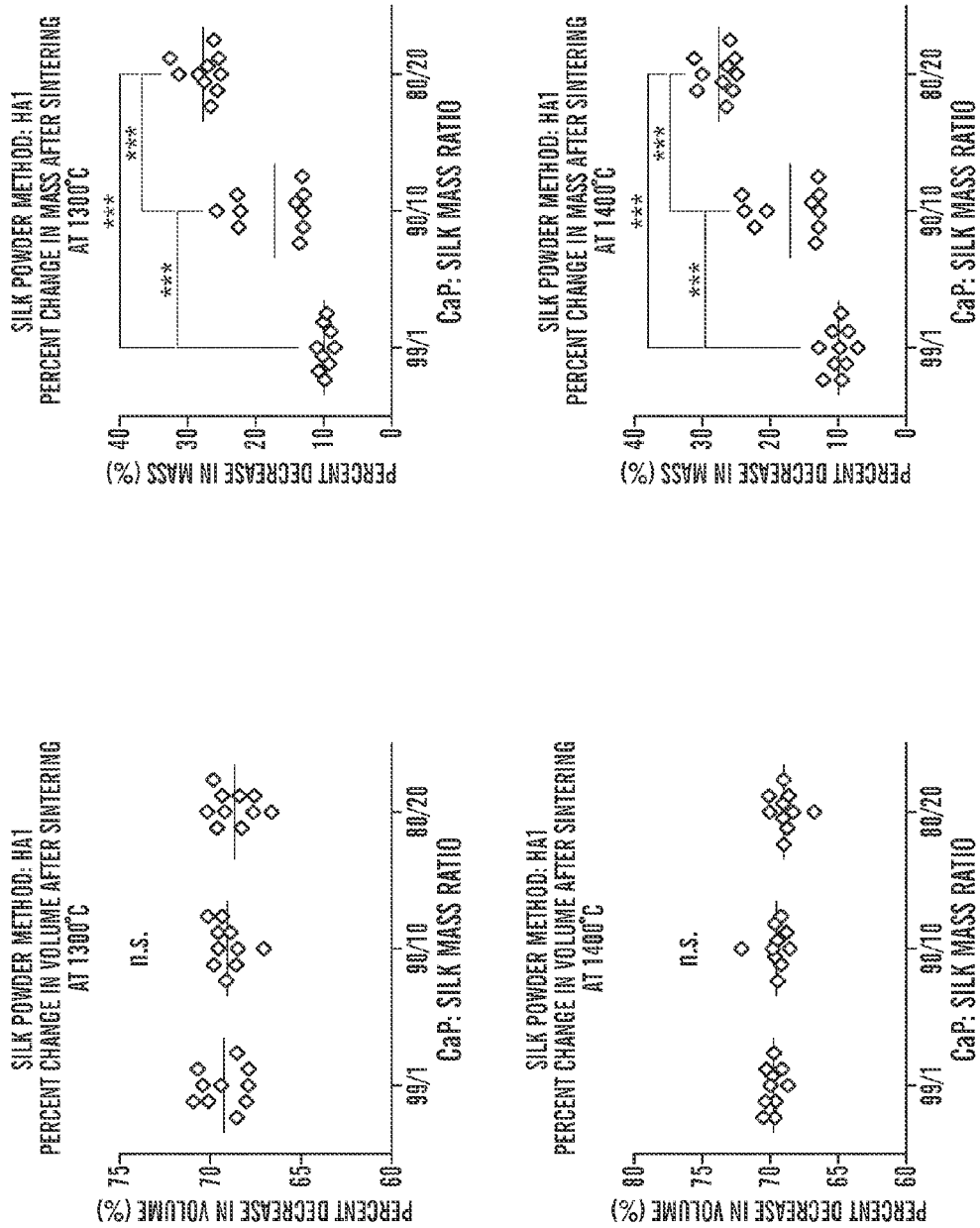
FIG. 7 shows shrink analysis of silk-CaP green bodies prepared according to embodiments of the Silk Powder Method during sintering.
Figure 8:
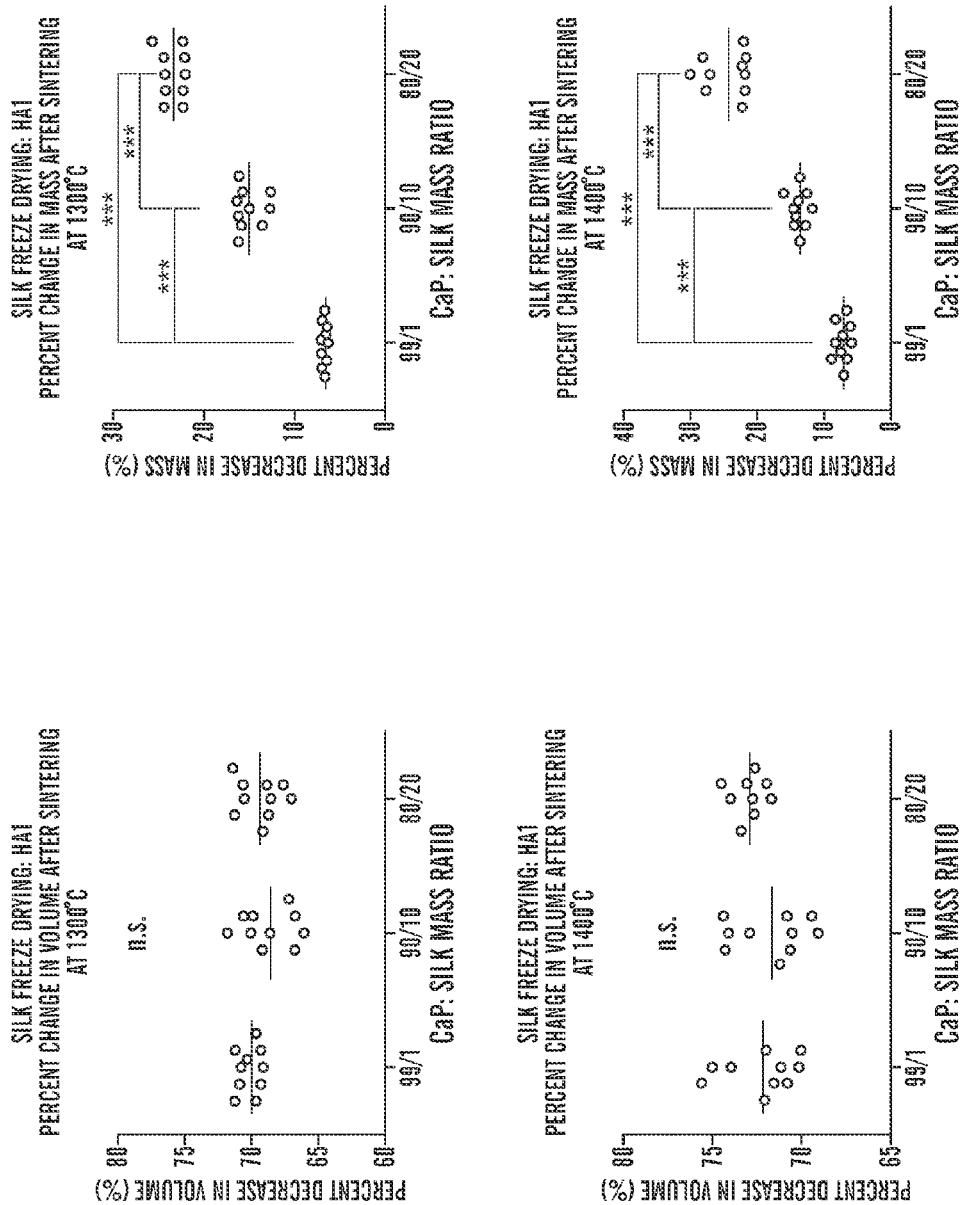
FIG. 8 shows shrink analysis of silk-CaP green bodies prepared according to embodiments of the Silk Freeze-Drying Method during sintering.
Figure 9:
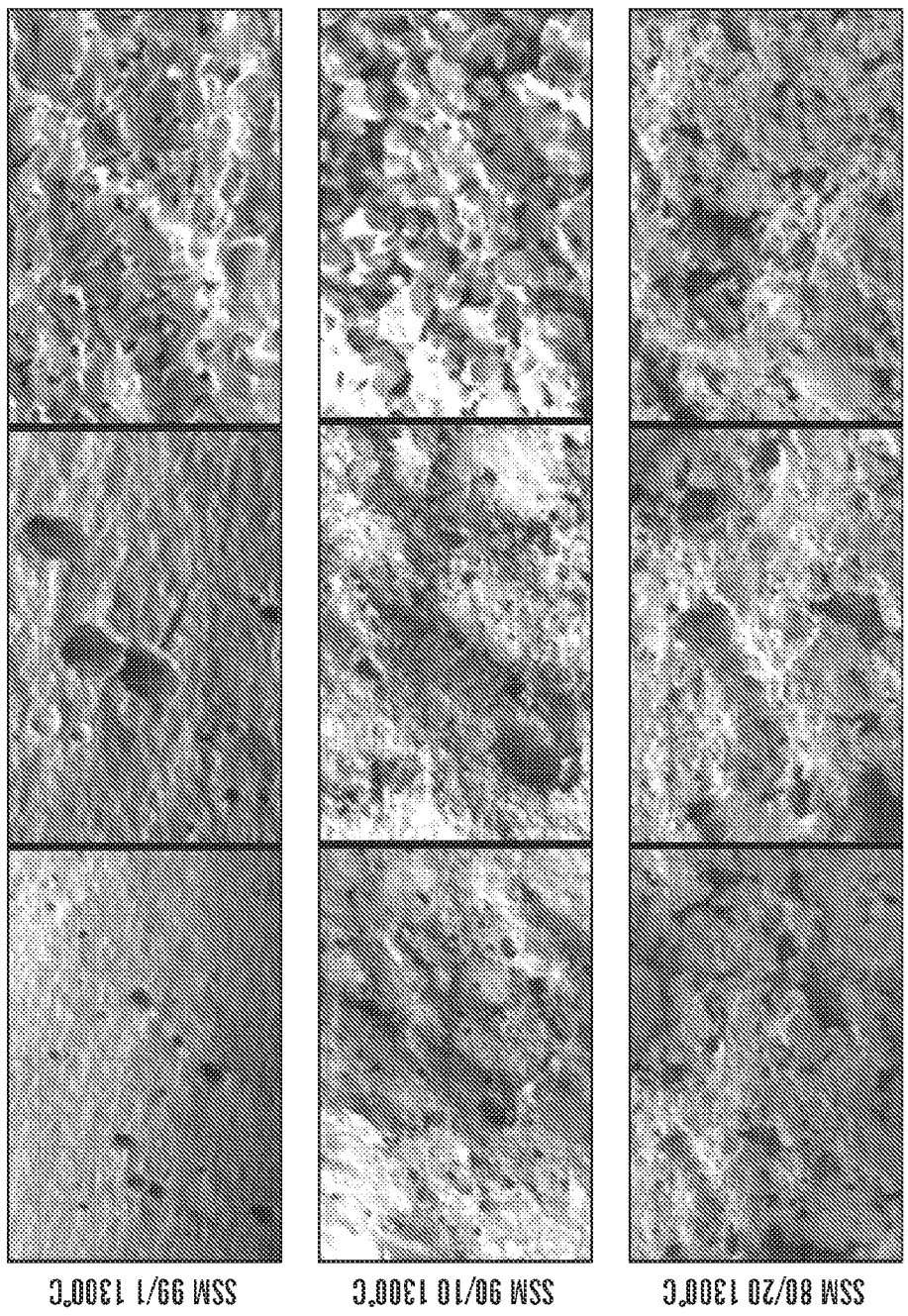
FIG. 9 shows SEM images of sintered CaP scaffolds prepared according to embodiments of the Silk Solvent Method sintered at 1300° C. (ratios are % CaP/% silk in the green body).
Figure 10:
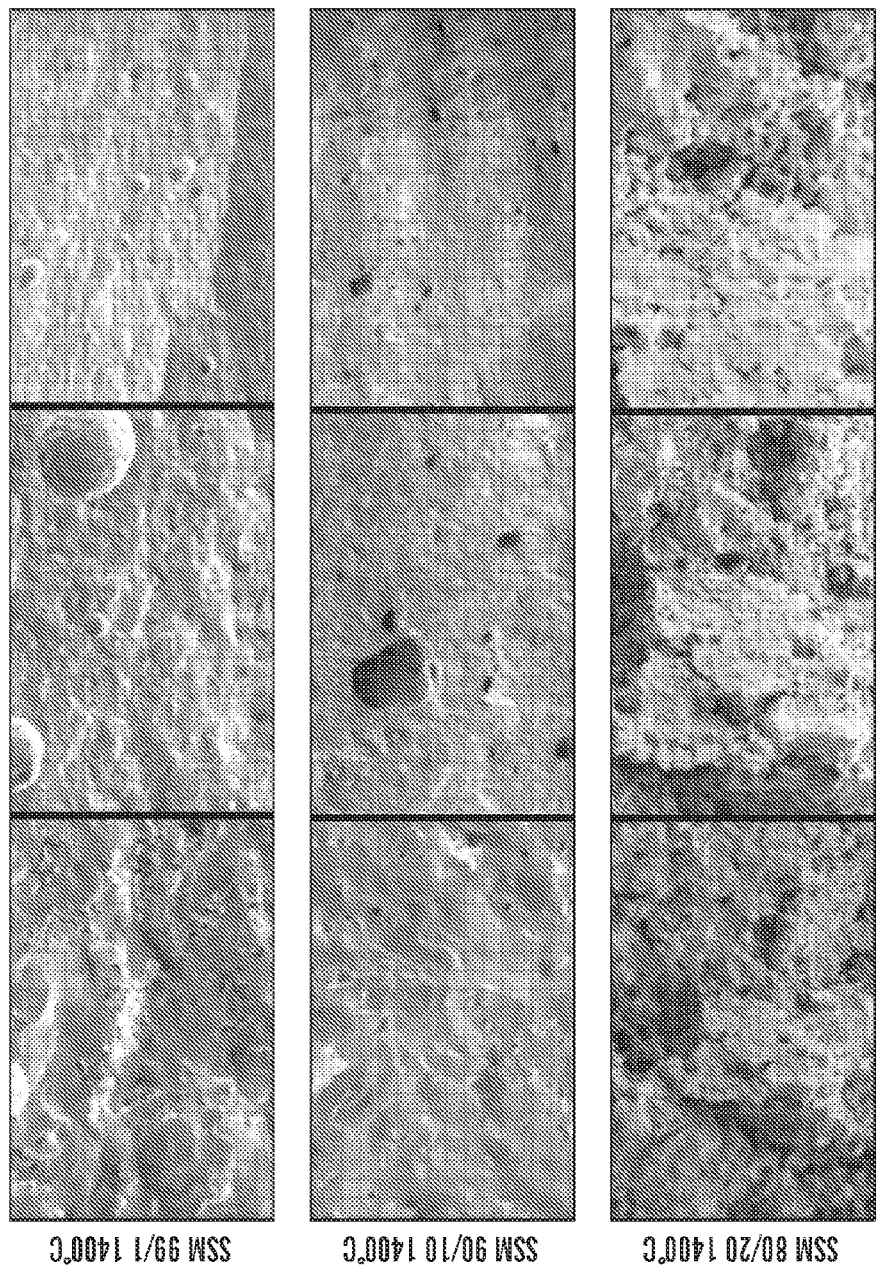
FIG. 10 shows SEM images of sintered CaP scaffolds prepared according to embodiments of the Silk Solvent Method sintered at 1400° C. (ratios are % CaP/% silk in the green body).
Figure 11:
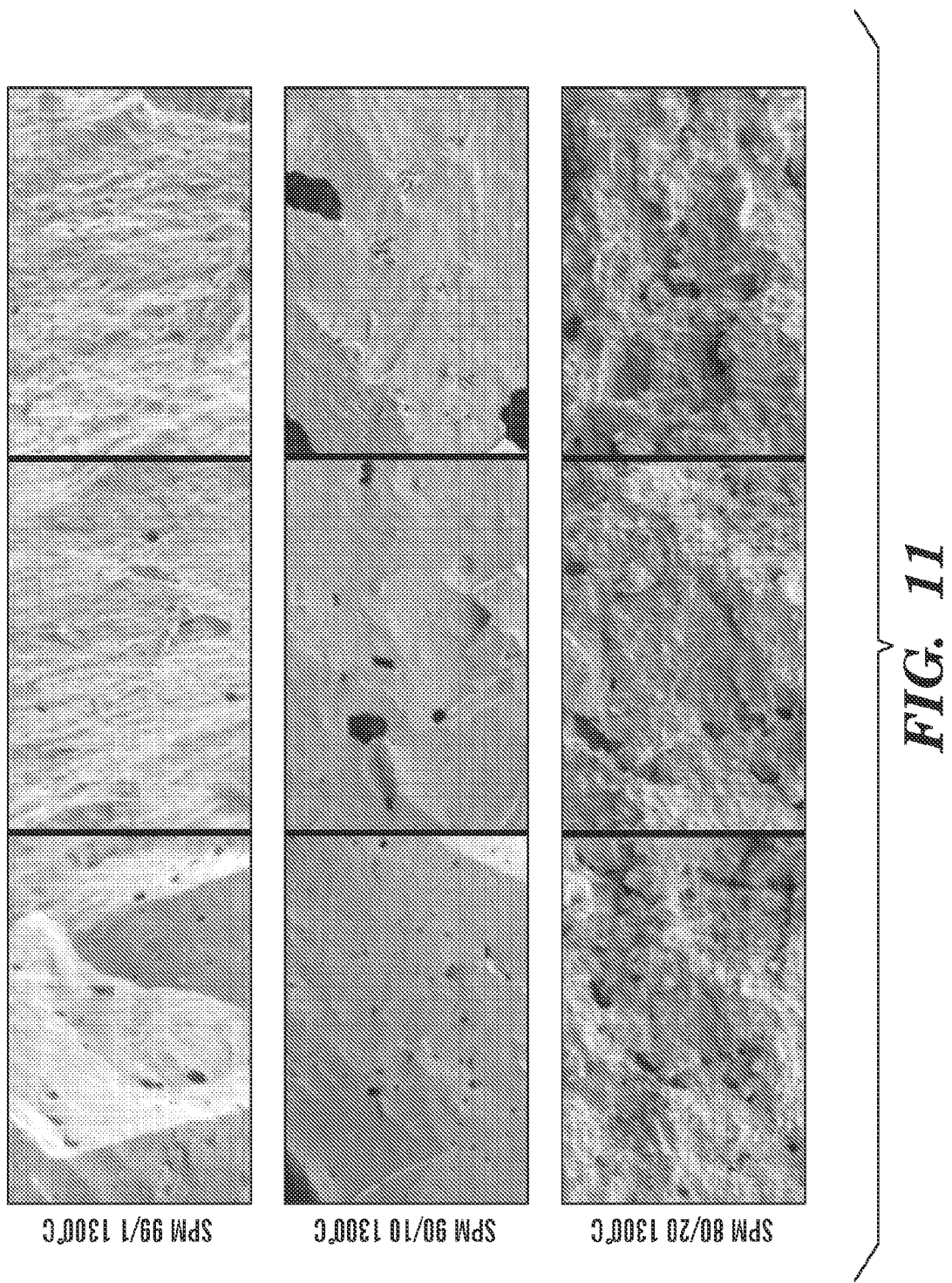
FIG. 11 shows SEM images of sintered CaP scaffolds prepared according to embodiments of the Silk Powder Method sintered at 1300° C. (ratios are % CaP/% silk in the green body).
Figure 12:
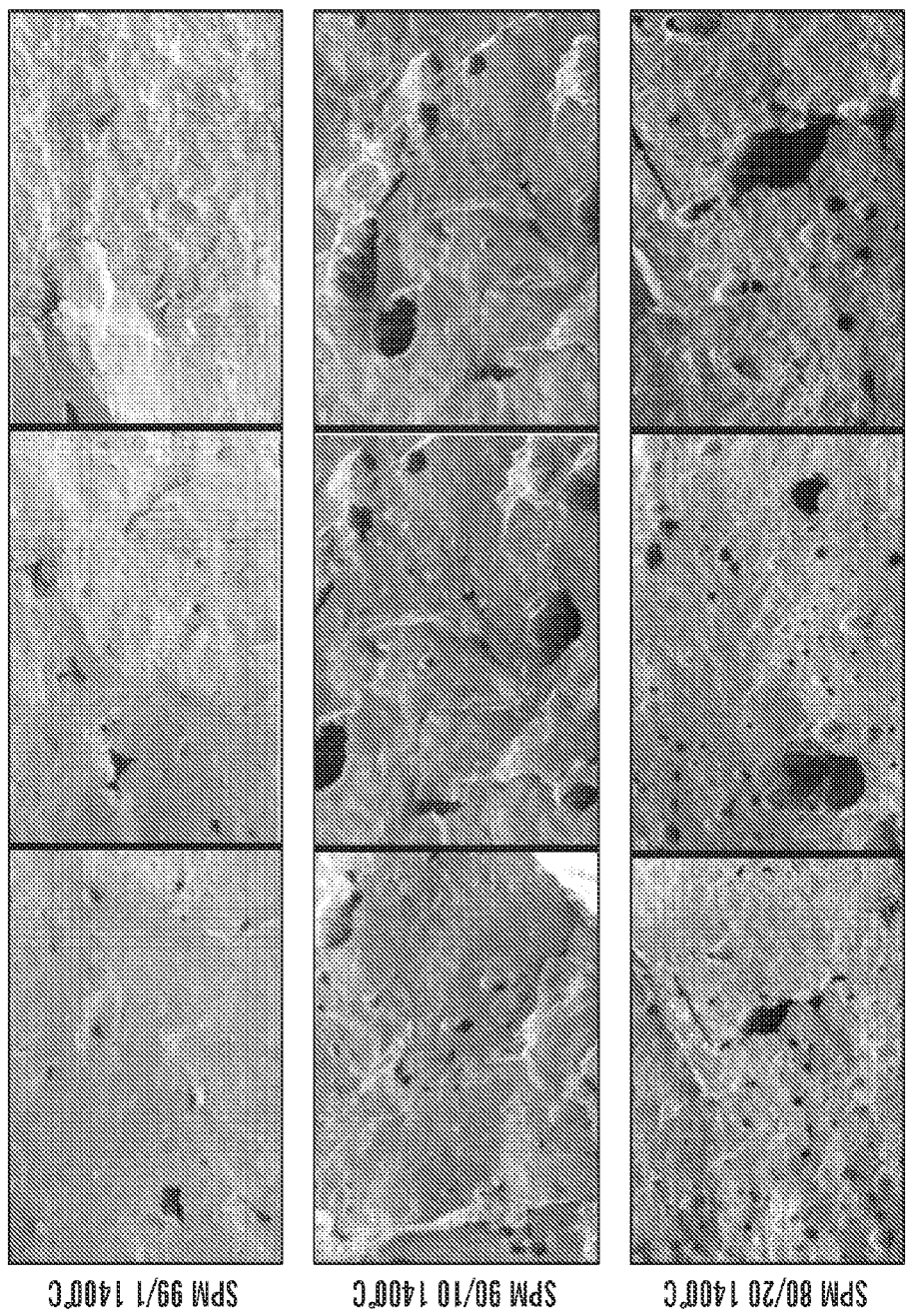
FIG. 12 shows SEM images of sintered CaP scaffolds prepared according to embodiments of the Silk Powder Method sintered at 1400° C. (ratios are % CaP/% silk in the green body).
Figure 13:
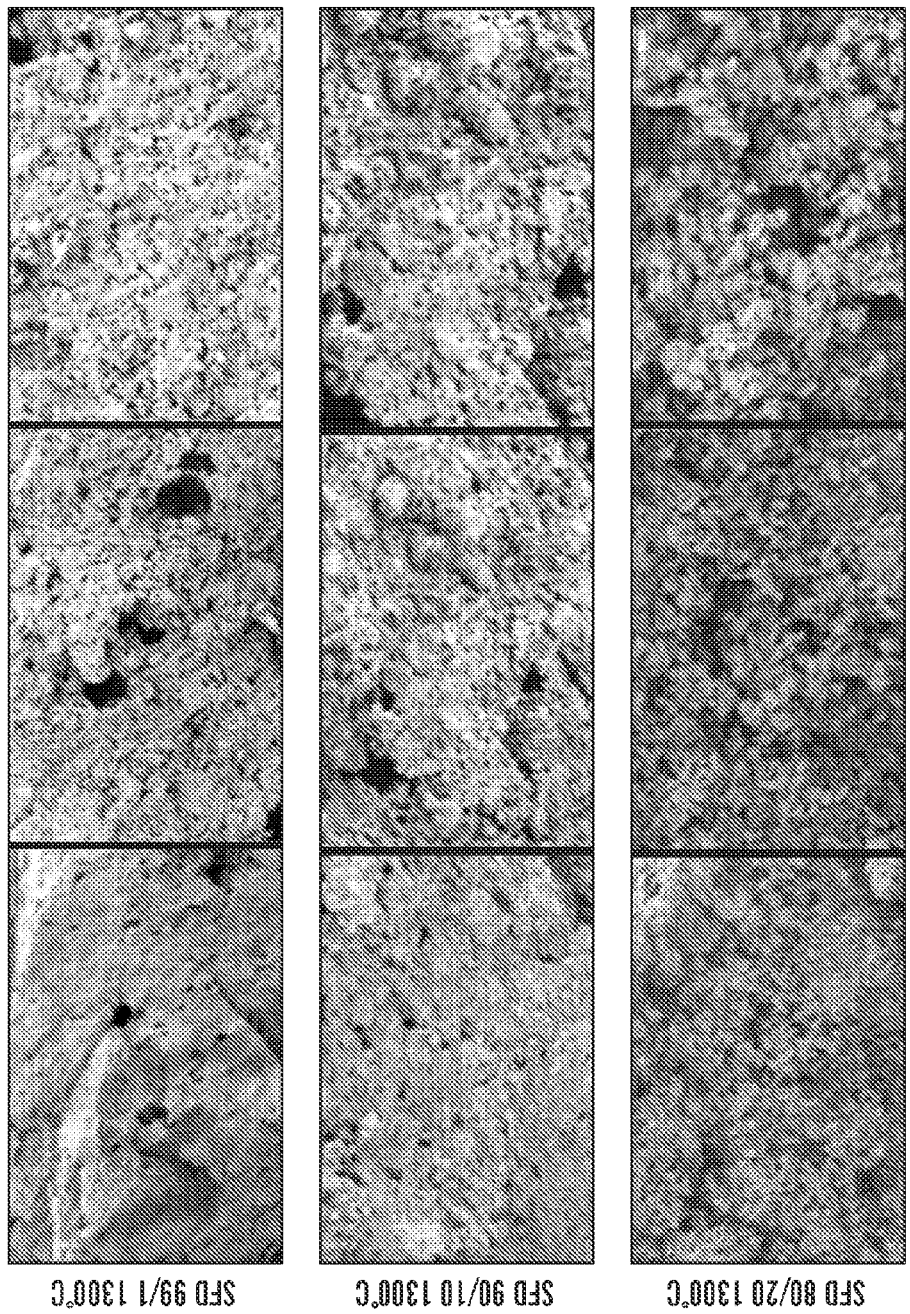
FIG. 13 shows SEM images of sintered CaP scaffolds prepared according to embodiments of the Silk Freeze-Drying Method sintered at 1300° C. (ratios are % CaP/% silk in the green body).
Figure 14:
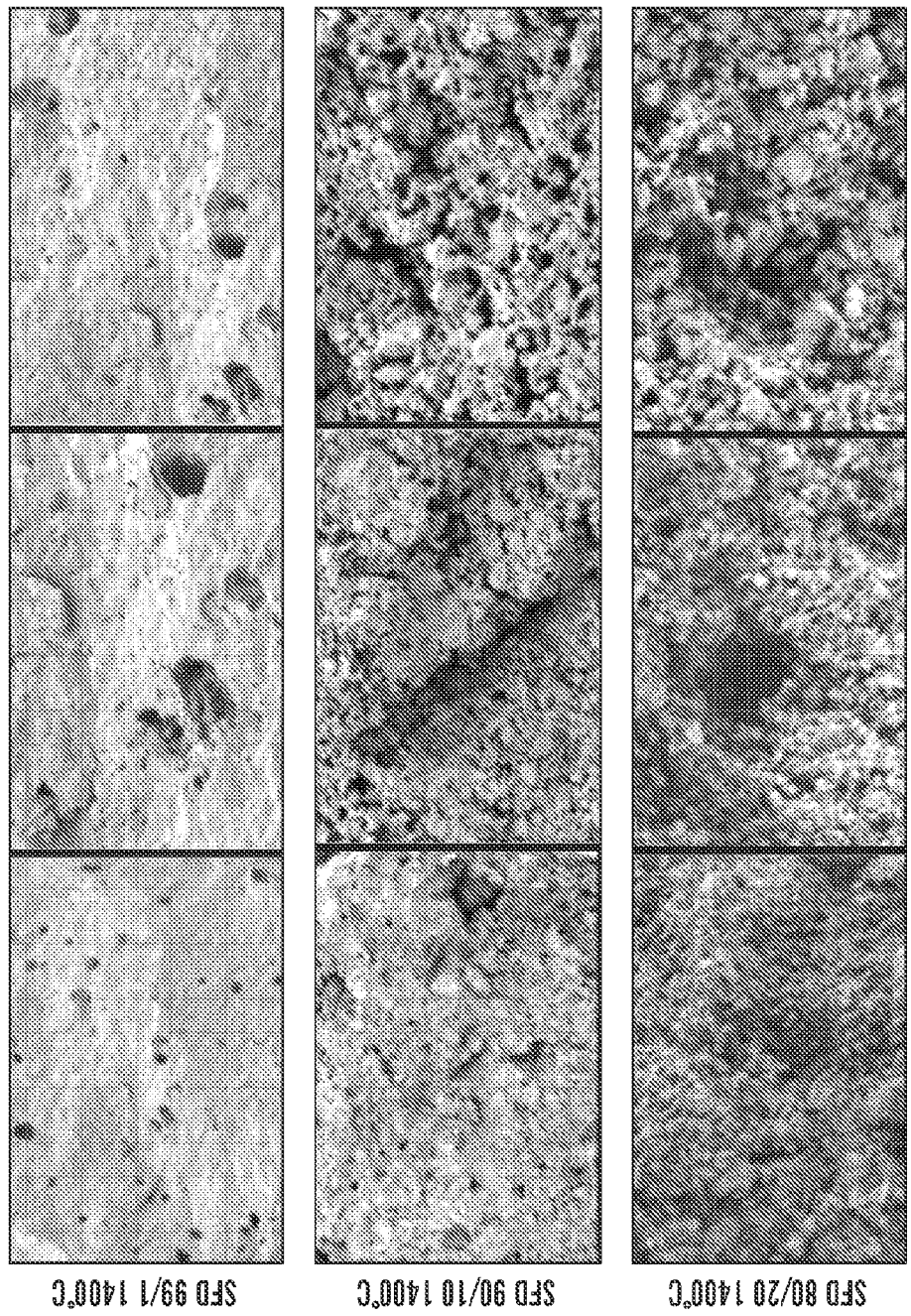
FIG. 14 shows SEM images of sintered CaP scaffolds prepared according to embodiments of the Silk Freeze-Drying Method sintered at 1400° C. (ratios are % CaP/% silk in the green body).

As seen from FIGS. 6-8, across all groups of % CaP-% silk green bodies, the amount that the volume of the scaffolds decreased stayed constant. However, the decrease in mass was generally larger for green bodies that contained more silk prior to sintering. This shows that the higher the % silk in the green body, the more porosity formed after sintering. Thus, porosity can be modulated by varying the amount of silk in the green body before sintering.

The SEM pictures in FIG. 9-14 show that scaffolds made via the Silk Freeze-Drying have higher pore interconnectivity and pore morphology whereas those made via the Silk Powder Method have lower pore interconnectivity. Lower % CaP-% silk ratios (green bodies with more silk in them) produce sintered ceramics with larger pores and more interconnected pores. Further, Silk Freeze-Dried scaffolds showed significantly lower densities than Silk Solvent Method or Silk Powder Method scaffolds, likely due to higher levels of porosity (data not shown)

Figure 15:
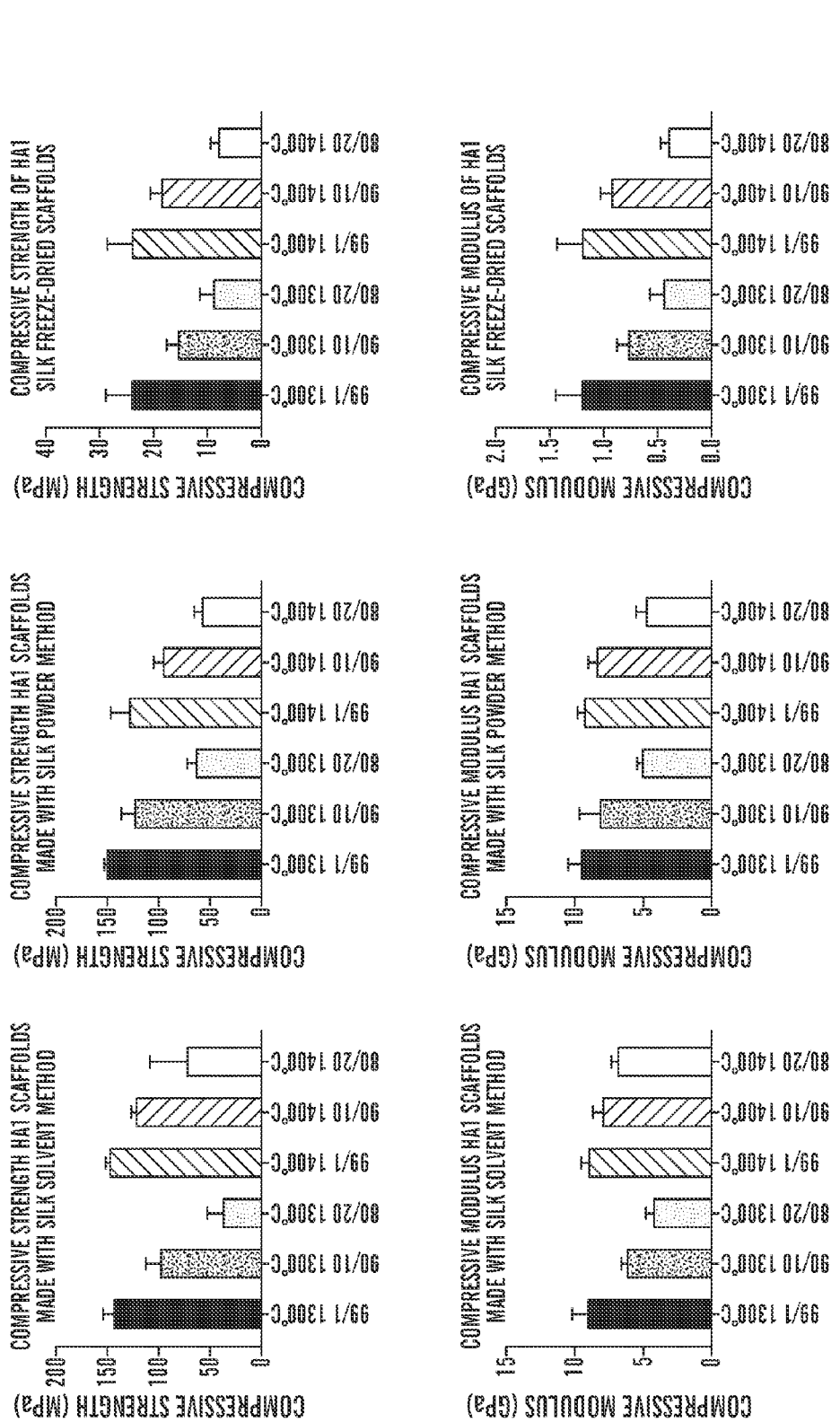
FIG. 15 shows compressive strength (in MPa) and compressive modulus (in GPa) of CaP scaffolds prepared according to embodiments of the Silk Solvent Method (left), Silk Powder Method (middle), and Silk Freeze-Drying Method (right).

The mechanical properties of the Silk Freeze-Dried scaffolds (under compression) showed that compressive strengths range from approximately 5-35 MPa and compressive moduli range from approximately 0.3-1.8 GPa. (FIG. 15, right). Further, higher % CaP-% silk ratios (less silk in the green body prior to sintering) produce ceramics that have higher compressive strengths and compressive moduli. (FIG. 15, right). The mechanical properties of scaffolds made via the Silk Powder Method showed that compressive strengths that range from approximately 55-165 MPa and compressive moduli that range from approximately 3-11 GPa. (FIG. 15, middle). The mechanical properties of scaffolds made via the Silk Solvent Method showed that compressive strengths range from approximately 45-155 MPa and compressive moduli range from approximately 4-10 GPa. (FIG. 15, left).

Figure 16:
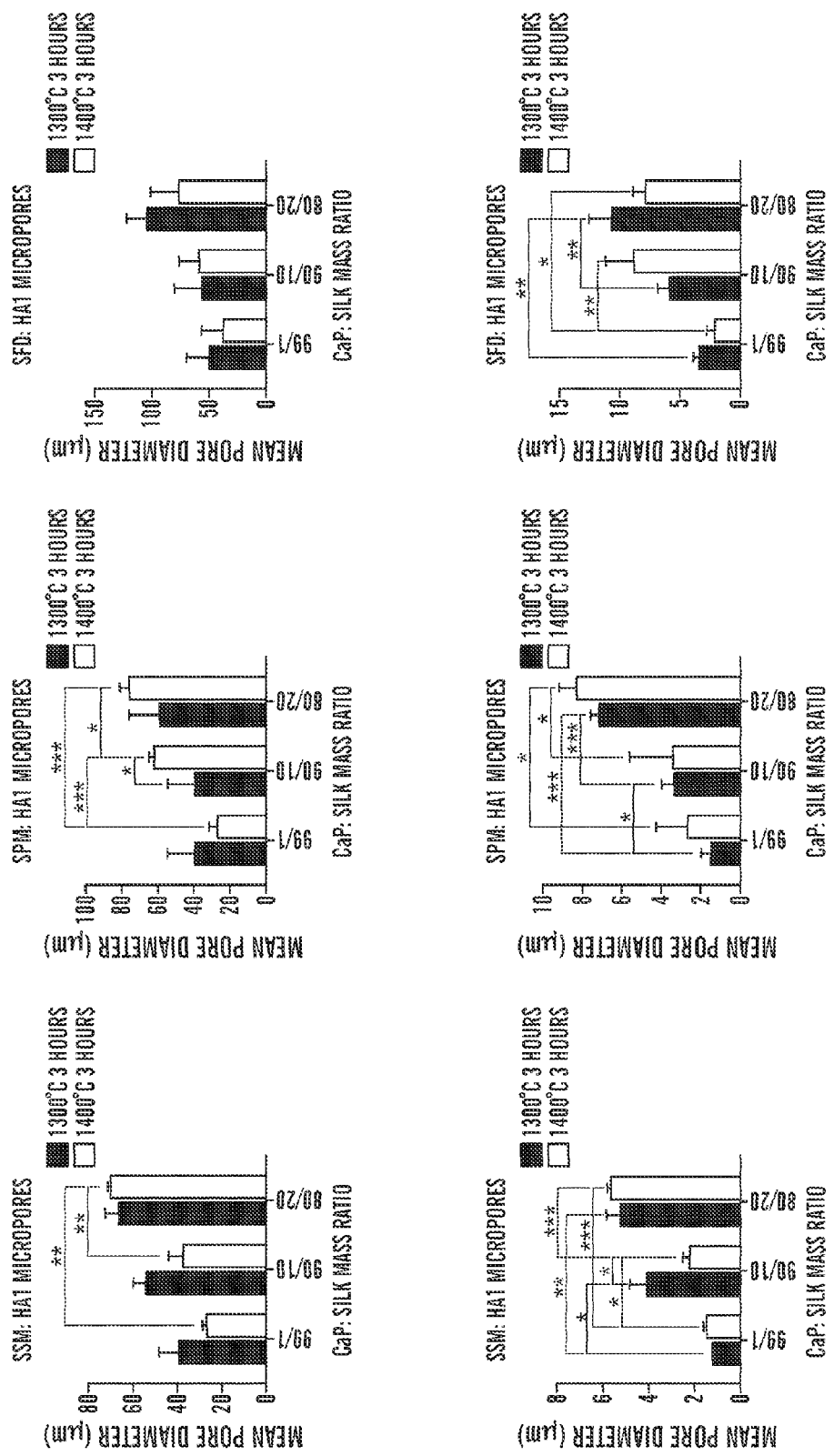
FIG. 16 shows mean pore size in sintered CaP scaffolds prepared according to embodiments of the Silk Solvent Method (left), Silk Powder Method (middle), and Silk Freeze-Drying Method (right).
Figure 17:
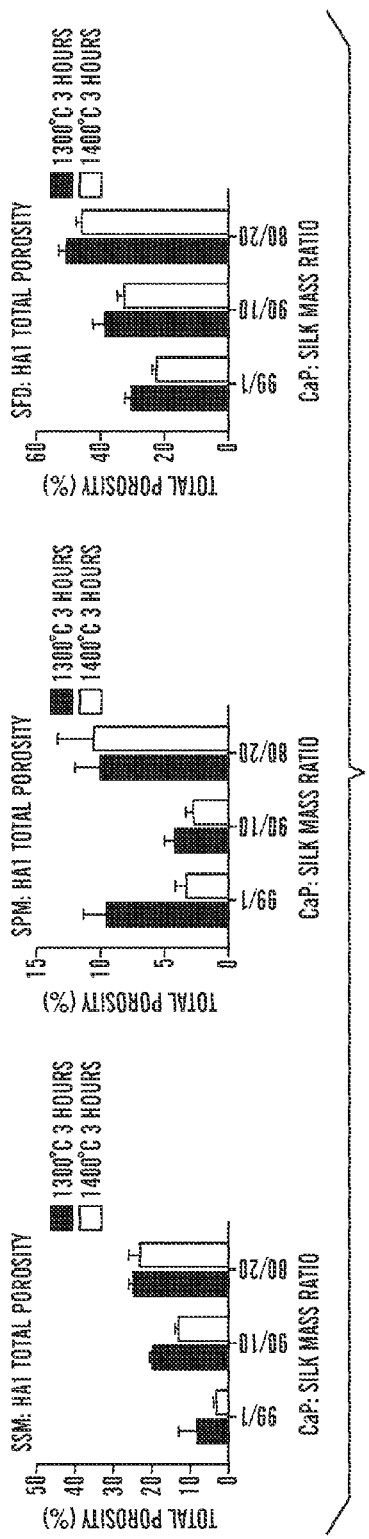
FIG. 17 shows the total porosity of sintered CaP scaffolds prepared according to embodiments of the Silk Solvent Method (top left), Silk Powder Method (top right), and Silk Freeze-Drying Method (bottom).

As seen from FIG. 16, pore size increased with increasing % silk in the CaP-Silk green body, and pore sizes generally were larger for Silk Freeze-Dried scaffolds than Silk Solvent or Silk Powder Scaffolds. Further, as seen from FIG. 17, total porosity was higher for lower % CaP-% silk ratios (more silk in the initial green body). The general trend for degree of porosity among the three methods was as follows: Silk Freeze-Drying>Silk Solvent Method>Silk Powder Method.

Figure 18:
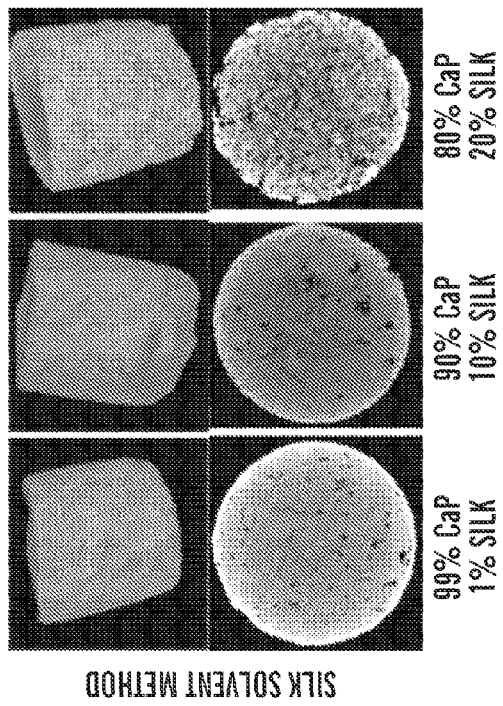
FIG. 18 shows micro-computed tomography imaging (top: surface images, bottom: sectional images) of sintered CaP scaffolds prepared according to embodiments of the Silk Solvent Method (ratios are % CaP/% silk in the green body).
Figure 19:
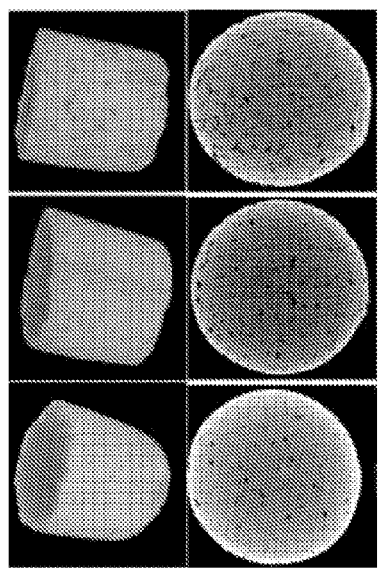
FIG. 19 shows micro-computed tomography imaging (top: surface images, bottom: sectional images) of sintered CaP scaffolds prepared according to embodiments of the Silk Powder Method (ratios are % CaP/% silk in the green body).
Figure 20:
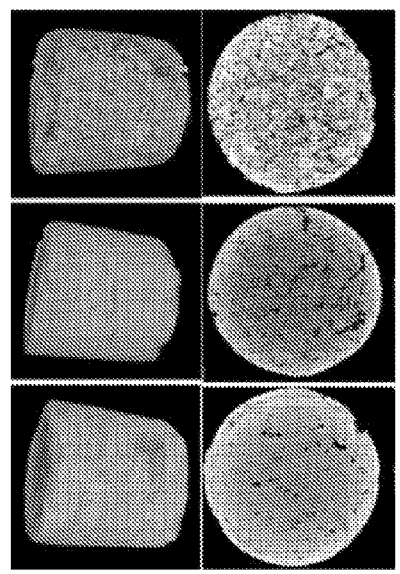
FIG. 20 shows micro-computed tomography imaging (top: surface images, bottom: sectional images) of sintered CaP scaffolds prepared according to embodiments of the Silk Freeze-Drying (ratios are % CaP/% silk in the green body).
Figure 25:
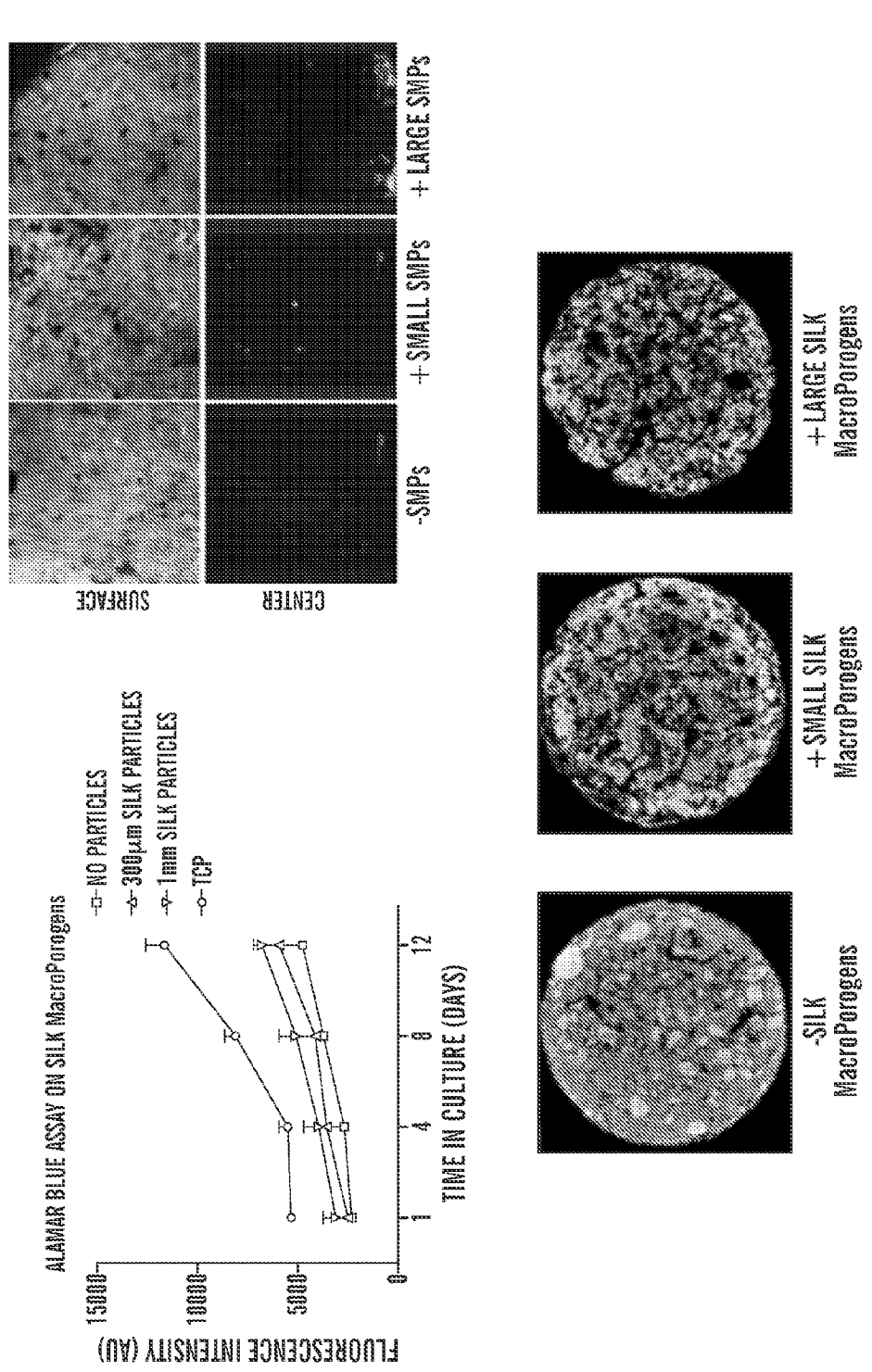
FIG. 25 shows Alamar blue proliferation assay on sintered CaP scaffolds prepared according to embodiments of the Silk Solvent Method with added silk macroporogens, and seeded with human bone marrow Mesenchymal stem cells (top left). Confocal imaging of Live/Dead stained scaffold surfaces after 14 days in culture (top right). Micro-computed tomography imaging of these scaffolds (bottom).
Figure 26:
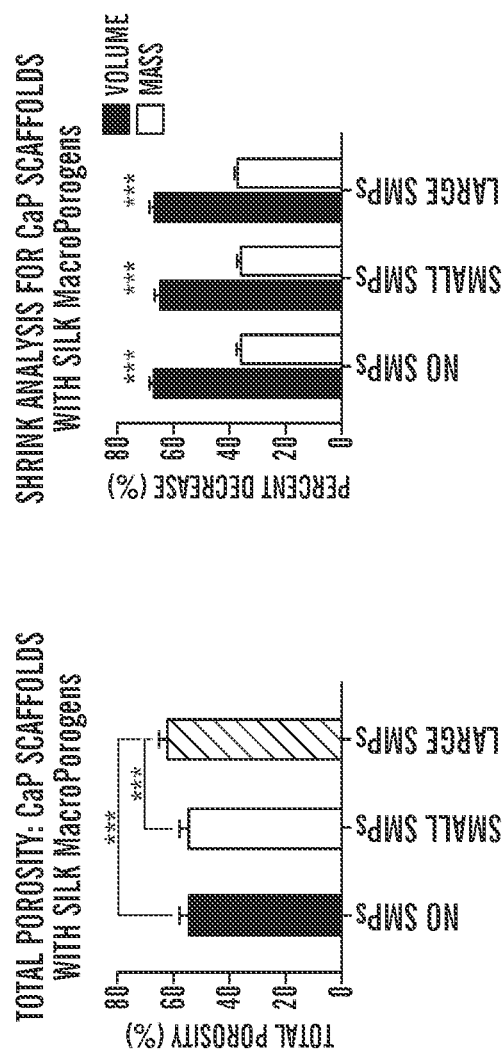
FIG. 26 shows the total porosity of sintered CaP scaffolds prepared according to embodiments of the Silk Solvent Method with added silk macroporogens (left), and shrink analysis of these scaffolds during sintering (right).
Figure 27A:
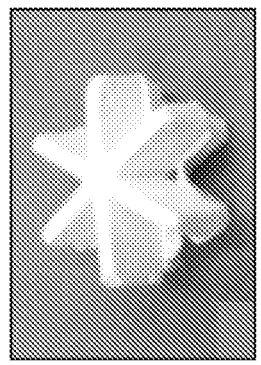
FIG. 27 shows images of stable, complex geometry shapes created via the addition of silk to CaP prior to sintering. Top left: Silk Freeze-Dried green bodies next to the sintered scaffolds. Top right: Star-shape model. Bottom left: CaP-silk "teeth" green bodies (80% CaP/20% silk). Bottom right: "Bolt"-shaped green body (80% CaP/20% silk).
Figure 27B:
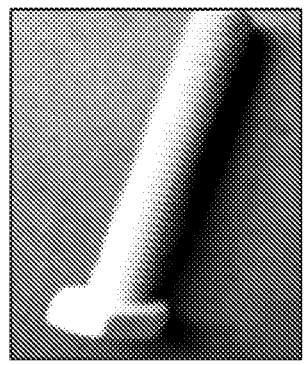
Figure 27C:
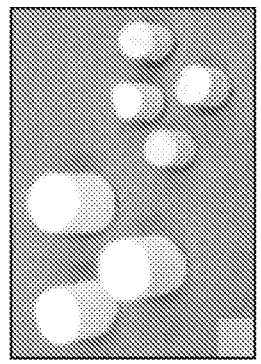
Figure 27D:
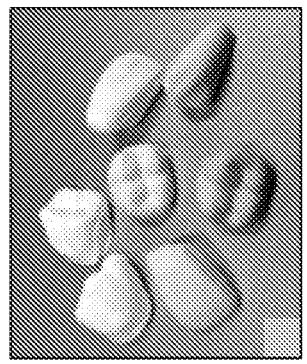

The micro-CT analysis in FIGS. 18-20 shows that there can be defects or air pockets that form in the material. Further, the pores in all scaffolds were evenly distributed, although pore size varied greatly. Comparing 99/1 scaffolds to 80/20 scaffolds, it is seen that there was a higher level of porosity and a very different scaffolds morphology between these groups for the Silk Solvent Method and Silk Freeze-Drying, however, there was not as much of a noticeable different between the 99/1 and 80/20 groups for the Silk Powder Method (indicating a more constant porosity). Further, Silk Freeze-Drying had different morphology and higher porosity than SSM and SPM. This shows that the method used for the production of the ceramic can lead to different physical properties of the ceramic material. Moreover, addition of silk macroporogens (SMPs) significantly increased the porosity and pore size within the sintered CaP scaffolds as compared to the no SMP control (there was also a noticeable difference between the small versus large macroporogens). (FIG. 25).

Figure 21:
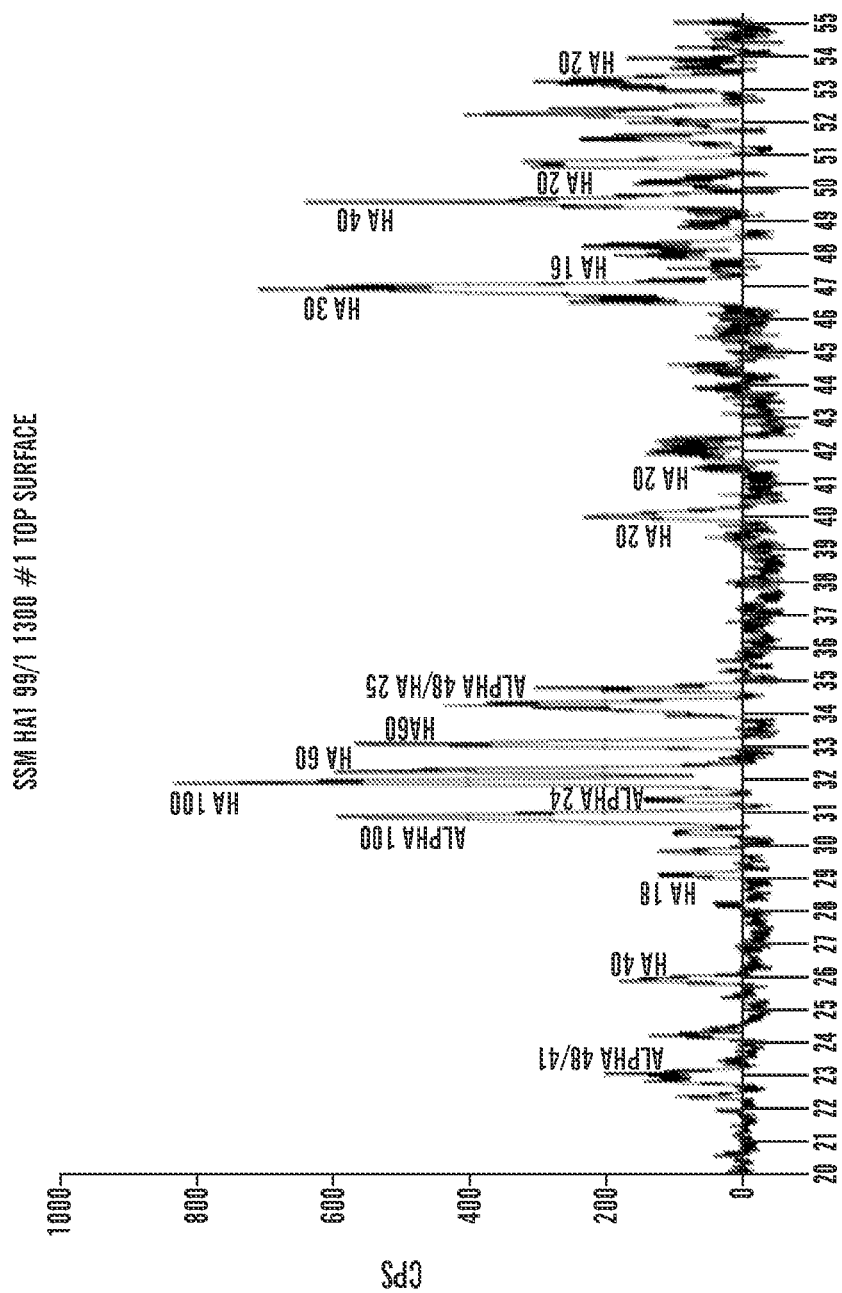
FIG. 21 shows X-ray diffraction pattern for the top surface of a sintered CaP scaffold prepared according to embodiments of the Silk Solvent Method (99% CaP/1% silk).

X-ray diffraction on the sintered scaffolds showed that there was a conversion of the hydroxyapatite material into a tricalcium phosphate (mostly alpha form) during sintering (FIG. 21 and data not shown). There was some dependence of this conversion on sintering temperature. It is also possible that there is some dependence of material conversion on material porosity (indirect correlation to the amount of silk present in the material prior to sintering). This is because a higher porosity sample would demonstrate better mass transport to allow for the conversion of HA to TCP.

Figure 22:
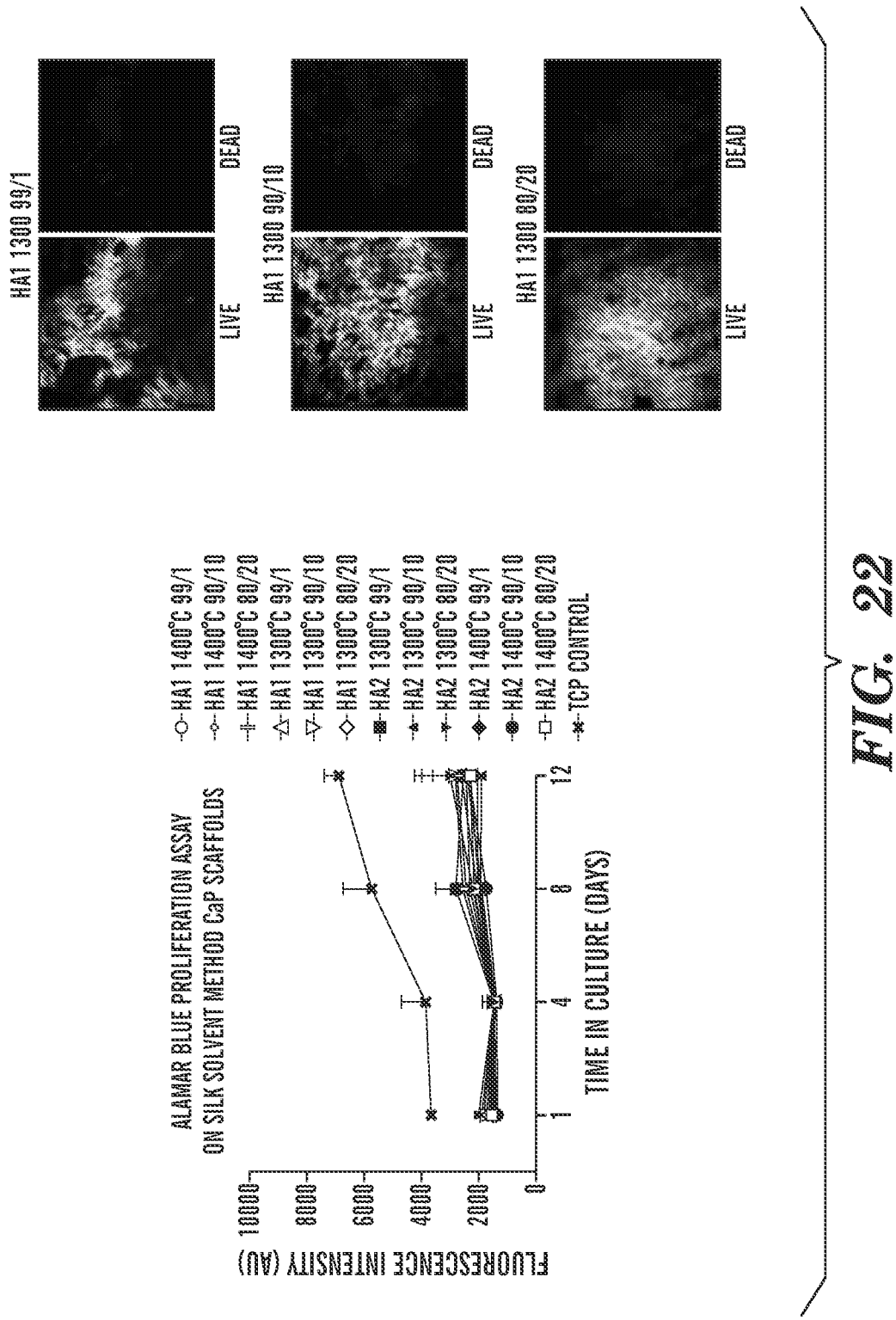
FIG. 22 shows Alamar blue proliferation assay on sintered CaP scaffolds prepared according to embodiments of the Silk Solvent Method and seeded with human bone marrow Mesenchymal stem cells (left). Confocal imaging of Live/Dead stained scaffold surfaces after 14 days in culture (right).
Figure 23:
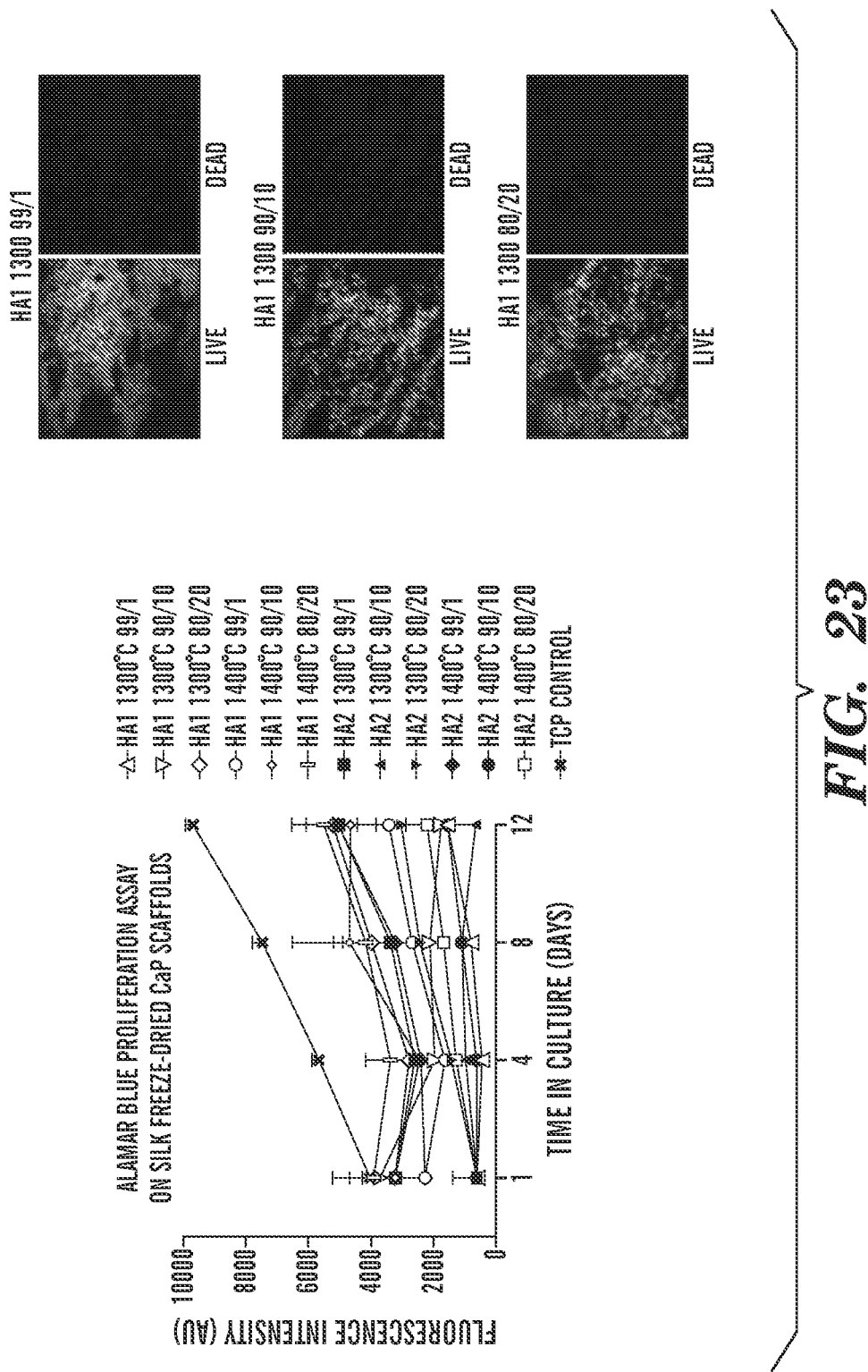
FIG. 23 shows Alamar blue proliferation assay on sintered CaP scaffolds prepared according to embodiments of the Silk Freeze-Drying and seeded with human bone marrow Mesenchymal stem cells (left). Confocal imaging of Live/Dead stained scaffold surfaces after 14 days in culture (right).

As seen from FIGS. 22 and 23, Alamar blue proliferation assayed showed that the CaP scaffolds demonstrate excellent biocompatibility with no cytotoxic response. Cell proliferation was also higher on Silk Freeze-Dried scaffolds as opposed to Silk Solvent Method scaffolds (likely due to increased porosity in the SFD scaffolds). Further, confocal imaging showed healthy monolayers of human mesenchymal stem cells forming on the surfaces of the CaP scaffolds.

Adding silk macroporogens (SMPs) increased the porosity of the scaffolds and aids in cell migration into the center of the scaffolds. (FIG. 25). A significant increase in cell proliferation rates was also observed. The size of the SMPs can be varied, the data is using small SMPs (<300 microns) and large SMPs (between 300 and 1000 microns).

Tables 6-11 show the hydration response of the silk foam scaffold in terms of the swelling ratio of the silk foam with deionized water. As can be seen, the sintered CaP material does not absorb water (no change in volume of the scaffolds before and after soaking), but the scaffolds do take up water into their interconnected pores (via capillary action), which explains the change in mass of the dry versus hydrated scaffolds.

TABLE 6

Hydration Response of CaP Scaffolds Formed by Silk Solvent Method

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA1 | 1300 | 5.50 | 5.50 | n.s. | 6.62 | 6.62 | n.s. | n.s. | 2.6% |
| 99/1 | 1400 | 5.38 | 5.38 | n.s. | 6.05 | 6.05 | n.s. | n.s. | 1.1% |
| HA1 | 1300 | 5.63 | 5.63 | n.s. | 6.43 | 6.43 | n.s. | n.s. | 5.9% |
| 90/10 | 1400 | 5.73 | 5.73 | n.s. | 6.25 | 6.25 | n.s. | n.s. | 3.7% |
| HA1 | 1300 | 5.50 | 5.50 | n.s. | 6.28 | 6.28 | n.s. | n.s. | 8.0% |
| 80/20 | 1400 | 5.52 | 5.52 | n.s. | 6.20 | 6.20 | n.s. | n.s. | 6.9% |

*Volume Swelling ratio = (Vs − Vd)/Vd
**Water uptake (%) = [(Ws − Wd)/Ws] × 100
*** Accuracy of calipers: ±0.01 mm
n = 6

TABLE 7

Hydration Response of CaP Scaffolds Formed by Silk Solvent Method

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA2 | 1300 | 5.95 | 5.95 | n.s. | 6.96 | 6.96 | n.s. | n.s. | 0.9% |
| 99/1 | 1400 | 5.93 | 5.93 | n.s. | 6.23 | 6.23 | n.s. | n.s. | 1.3% |
| HA2 | 1300 | 5.55 | 5.55 | n.s. | 6.75 | 6.75 | n.s. | n.s. | 5.3% |
| 90/10 | 1400 | 5.97 | 5.97 | n.s. | 6.42 | 6.42 | n.s. | n.s. | 3.9% |

TABLE 7-continued

Hydration Response of CaP Scaffolds Formed by Silk Solvent Method

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA2 | 1300 | 5.57 | 5.57 | n.s. | 6.73 | 6.73 | n.s. | n.s. | 8.7% |
| 80/20 | 1400 | 5.83 | 5.83 | n.s. | 6.38 | 6.38 | n.s. | n.s. | 14.6% |

*Volume Swelling ratio = (Vs − Vd)/Vd
**Water uptake (%) = [(Ws − Wd)/Ws] × 100
*** Accuracy of calipers: ±0.01 mm
n = 6

TABLE 8

Hydration Response of CaP Scaffolds Formed by Silk Powder Method

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA1 | 1300 | 5.88 | 5.88 | n.s. | 6.15 | 6.15 | n.s. | n.s. | 3.3% |
| 99/1 | 1400 | 5.67 | 5.67 | n.s. | 6.07 | 6.07 | n.s. | n.s. | 1.0% |
| HA1 | 1300 | 5.55 | 5.55 | n.s. | 5.95 | 5.95 | n.s. | n.s. | 2.0% |
| 90/10 | 1400 | 5.50 | 5.50 | n.s. | 5.85 | 5.85 | n.s. | n.s. | 1.2% |
| HA1 | 1300 | 5.53 | 5.53 | n.s. | 5.65 | 5.65 | n.s. | n.s. | 2.0% |
| 80/20 | 1400 | 5.75 | 5.75 | n.s. | 5.72 | 5.72 | n.s. | n.s. | 2.0% |

*Volume Swelling ratio = (Vs − Vd)/Vd
**Water uptake (%) = [(Ws − Wd)/Ws] × 100
*** Accuracy of calipers: ±0.01 mm
n = 6

TABLE 9

Hydration Response of CaP Scaffolds Formed by Silk Powder Method

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA2 | 1300 | 6.00 | 6.00 | n.s. | 6.50 | 6.50 | n.s. | n.s. | 1.3% |
| 99/1 | 1400 | 5.95 | 5.95 | n.s. | 6.73 | 6.73 | n.s. | n.s. | 0.7% |
| HA2 | 1300 | 5.67 | 5.67 | n.s. | 6.62 | 6.62 | n.s. | n.s. | 0.8% |
| 90/10 | 1400 | 6.08 | 6.08 | n.s. | 6.67 | 6.67 | n.s. | n.s. | 0.7% |
| HA2 | 1300 | 5.98 | 5.98 | n.s. | 6.43 | 6.43 | n.s. | n.s. | 1.4% |
| 80/20 | 1400 | 6.05 | 6.05 | n.s. | 6.38 | 6.38 | n.s. | n.s. | 1.1% |

*Volume Swelling ratio = (Vs − Vd)/Vd
**Water uptake (%) = [(Ws − Wd)/Ws] × 100
*** Accuracy of calipers: ±0.01 mm
n = 6

TABLE 10

Hydration Response of CaP Scaffolds Formed by Silk Freeze-Drying

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA1 | 1300 | 6.02 | 6.02 | n.s. | 6.23 | 6.23 | n.s. | n.s. | 11.1% |
| 99/1 | 1400 | 5.88 | 5.88 | n.s. | 6.05 | 6.05 | n.s. | n.s. | 7.3% |
| HA1 | 1300 | 5.93 | 5.93 | n.s. | 6.40 | 6.40 | n.s. | n.s. | 15.3% |
| 90/10 | 1400 | 5.97 | 5.97 | n.s. | 6.32 | 6.32 | n.s. | n.s. | 12.3% |
| HA1 | 1300 | 6.12 | 6.12 | n.s. | 6.63 | 6.63 | n.s. | n.s. | 22.5% |
| 80/20 | 1400 | 5.87 | 5.87 | n.s. | 6.48 | 6.48 | n.s. | n.s. | 19.4% |

*Volume Swelling ratio = (Vs − Vd)/Vd
**Water uptake (%) = [(Ws − Wd)/Ws] × 100
*** Accuracy of calipers: ±0.01 mm
n = 6

TABLE 11

Hydration Response of CaP Scaffolds Formed by Silk Freeze-Drying

| Method | Temp (° C.) | Dry height (mm) | Hydrated height (mm) | Increase in height (%) | Dry diam (mm) | Hydrated diam (mm) | Increase in diam (%) | Volume Swell ratio* | Water uptake (%)** |
|---|---|---|---|---|---|---|---|---|---|
| HA2 99/1 | 1300 | 6.28 | 6.28 | n.s. | 6.62 | 6.62 | n.s. | n.s. | 5.8% |
|  | 1400 | 6.13 | 6.13 | n.s. | 6.48 | 6.48 | n.s. | n.s. | 4.2% |
| HA2 90/10 | 1300 | 5.87 | 5.87 | n.s. | 6.80 | 6.80 | n.s. | n.s. | 9.1% |
|  | 1400 | 6.08 | 6.08 | n.s. | 6.73 | 6.73 | n.s. | n.s. | 7.3% |
| HA2 80/20 | 1300 | 6.25 | 6.25 | n.s. | 6.67 | 6.67 | n.s. | n.s. | 19.6% |
|  | 1400 | 6.25 | 6.25 | n.s. | 6.62 | 6.62 | n.s. | n.s. | 18.3% |

*Volume Swelling ratio = (Vs − Vd)/Vd
**Water uptake (%) = [(Ws − Wd)/Ws] × 100
*** Accuracy of calipers: ±0.01 mm
n = 6

The work presented herein shows that silk is an excellent binder that can hold together ceramic particles in simple or complex shapes prior to sintering. Accordingly, the methods and compositions disclosed herein provide that silk can be used as a binder that, when mixed with calcium phosphate (or other ceramic material), binds and consolidates the ceramics particles into a 'green body' of pre-defined geometry. Once the silk in the green body has been stabilized (via mild heat or freeze-drying) the silk will act to stabilize the green body and retain its shape, and will not dissolve upon contact with water. The silk in the green body can act as a sacrificial polymer (porogen) during sintering to achieve a desired degree of porosity in the finished sintered ceramic. Silk can be added to the ceramic in a variety of formats including but not limited to: solution (both aqueous and solvent based), powder or particles (including non-soluble macroporogens, fibers, gels, etc. . . . . Any type of calcium phosphate powder (or other ceramic powder can be used, including reactive CaP powders which would not require sintering. The silk-CaP mixtures can be hand-molded, sintered and then machined; or they could be injection molded and then sintered; or they could be pressed in dry form using uniaxial dry pressing techniques and then machined.

Inventors note that the ceramic materials produced using the method disclosed herein have much higher mechanical properties than most other ceramics produced by any other method. Further, sintering with silk as a porogen has never been disclosed in the prior art. This means that the finished scaffold does not contain any remnants of silk. In general, if silk has been added to ceramic it has not involved a type of densification/hardening process as disclosed herein. Silk macroporogens (or other forms like fibers) can be used as add porogens to create much larger interconnected pores that typically seen in other ceramic models. The uniaxial dry pressed materials are very different from any other ceramic made with silk and CaP because the pressed materials do not involve solvent and are very dense with a different consistency and do not need to be sintered (but could). Injection molding of a silk protein with a ceramic is novel and scaffods have never been made in this fashion before.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of preparing a porous ceramic material, the method comprising:
   (i) obtaining a mixture by combining a calcium phosphate material and silk fibroin at a ratio of at least 80:20, respectively;
   (ii) forming a green body from the mixture; and
   (iii) sintering the green body under conditions sufficient to form the porous ceramic material.

2. The method of claim 1, wherein said obtaining the mixture comprises adding the calcium phosphate material as a powder or plurality of particles to an aqueous silk solution comprising silk fibroin.

3. The method of claim 1, wherein said obtaining the mixture comprises:
   (i) preparing a mixture of the calcium phosphate material and silk fibroin powder or particles; and
   (ii) adding water to form the composition.

4. The method of claim 1, wherein said obtaining the mixture comprises adding silk fibroin powder or particles to a solution of the calcium phosphate material.

5. The method of claim 1, wherein the silk fibroin is in the form of silk fibroin powder or particles.

6. The method of claim 5, wherein the silk fibroin powder or particles is/are prepared by a method comprising:
   (i) freeze-drying a solution comprising silk fibroin to produce a silk material; and
   (ii) reducing the silk material from (i) into a powder or particulates.

7. The method of claim 5, wherein the silk fibroin powder or particles is/are prepared by a method comprising:
   (i) freezing a solution comprising silk fibroin at about −20° C. for about 24 hours;
   (ii) transferring the frozen solution to a temperature of about −80° C. for about 2-3 hours;

(iii) lyophilizing the frozen solution at a pressure of about 0.006-100 Torr for about 24-48 hours, or until the silk fibroin is completely lyophilized; and (iv) blending the lyophilized solution for 2-3 minutes to produce large particles, or ball milling the lyophilized solution at about 200-350 rpm for about 2-3 hours to produce a fine silk powder.

8. The method of claim 1, wherein said obtaining the mixture comprises mixing a solution comprising the calcium phosphate material with a solution comprising silk fibroin.

9. The method of claim 1, wherein the mixture comprises from about 0.1% (w/v) to about 15% (w/v) silk fibroin.

10. The method of claim 1, wherein the calcium phosphate material is selected from the group consisting of brushite, octacalcium phosphate, tricalcium phosphate, calcium hydrogen phosphate, calcium dihydrogen phosphate, apatite, hydroxyapatite, and any combinations thereof.

11. The method of claim 1, wherein the mixture has a viscosity from about 0.1 to about 250 Pa·s.

12. The method of claim 1, wherein the mixture has a viscosity from about 100 to about 500 Pa·s.

13. The method of claim 1, wherein said forming the green body comprises transferring at least a part of the composition to a mold or forming the composition into a desired shape.

14. The method of claim 1, wherein said forming the green body from the mixture comprises incubating the mixture at an elevated temperature.

15. The method of claim 14, wherein said elevated temperature is from about 30° C. to about 95° C.

16. The method of claim 14, wherein said incubating is for at least 6 hours.

17. The method of claim 1, wherein said forming the green body from the mixture comprises freeze-drying the mixture.

18. The method of claim 17, wherein freeze-drying comprises freezing the mixture at about −20° C. for about 24 hours and lyophilizing the frozen mixture at about 0.006-100 Torr for about 24-28 hours.

19. The method of claim 1, wherein said sintering comprises heating the green body to a temperature of about 1200° C.-1500° C.

20. The method of claim 19, wherein said sintering comprises a linear ramp heating rate of about 5° C./min to about 25° C./min.

21. The method of claim 1, wherein said sintering comprises heating the green body for a period of about 1 hour to about 12 hours.

22. The method of claim 1, wherein said sintering comprises heating the green body at a temperature of 1300° C.-1400° C. for 2-3 hours with a linear ramp heating rate of 8° C./minute.

23. The method of claim 1, further comprising processing the porous ceramic material of step (iii) to a desired shape.

24. The method of claim 23, wherein said processing is selected from the group consisting of machining, turning (lathe), rolling, thread rolling, drilling, milling, sanding, punching, die cutting, blanking, broaching, and any combinations thereof.

25. The method of claim 1, wherein the composition comprises calcium phosphate material and silk fibroin at a mass ratio of about 80:20, respectively.

26. The method of claim 1, wherein the composition comprises calcium phosphate material and silk fibroin at a mass ratio of about 90:10, respectively.

27. The method of claim 1, wherein the composition comprises calcium phosphate material and silk fibroin at a mass ratio of about 99:1, respectively.

* * * * *